(12) United States Patent
Ahituv et al.

(10) Patent No.: US 12,285,496 B2
(45) Date of Patent: Apr. 29, 2025

(54) GENE THERAPY FOR HAPLOINSUFFICIENCY

(71) Applicant: The Regents of the University of California, Oakland, CA (US)

(72) Inventors: Nadav Ahituv, San Francisco, CA (US); Navneet Matharu, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 142 days.

(21) Appl. No.: 17/963,901

(22) Filed: Oct. 11, 2022

(65) Prior Publication Data

US 2023/0293729 A1 Sep. 21, 2023

Related U.S. Application Data

(62) Division of application No. 16/479,177, filed as application No. PCT/US2018/017186 on Feb. 7, 2018, now Pat. No. 11,730,828.

(60) Provisional application No. 62/455,988, filed on Feb. 7, 2017.

(51) Int. Cl.
| | | |
|---|---|---|
| C07H 21/02 | (2006.01) | |
| A01K 67/0276 | (2024.01) | |
| A61K 48/00 | (2006.01) | |
| A61P 3/04 | (2006.01) | |
| C12N 9/22 | (2006.01) | |
| C12N 15/10 | (2006.01) | |
| C12N 15/113 | (2010.01) | |
| C12N 15/86 | (2006.01) | |

(52) U.S. Cl.
CPC ...... *A61K 48/0066* (2013.01); *A01K 67/0276* (2013.01); *A61K 48/0016* (2013.01); *A61P 3/04* (2018.01); *C12N 9/22* (2013.01); *C12N 15/102* (2013.01); *C12N 15/113* (2013.01); *C12N 15/86* (2013.01); *A01K 2217/077* (2013.01); *A01K 2227/105* (2013.01); *A01K 2267/0362* (2013.01); *C12N 2310/20* (2017.05)

(58) Field of Classification Search
CPC .......................... C12N 15/113; C12N 2310/20
See application file for complete search history.

(56) References Cited

U.S. PATENT DOCUMENTS

| | | | |
|---|---|---|---|
| 11,730,828 | B2 | 8/2023 | Ahituv et al. |
| 2016/0039893 | A1 | 2/2016 | Neutzner et al. |

| | | | |
|---|---|---|---|
| 2016/0324987 | A1 | 11/2016 | Wang et al. |
| 2016/0338327 | A1 | 11/2016 | Kurrasch et al. |
| 2016/0355797 | A1 | 12/2016 | Konermann et al. |

FOREIGN PATENT DOCUMENTS

| | | |
|---|---|---|
| CN | 105358568 A | 2/2016 |
| EP | 3045537 A1 | 7/2016 |
| EP | 3510152 A1 | 7/2019 |
| WO | 2014204723 A1 | 12/2014 |
| WO | 2014204729 A1 | 12/2014 |
| WO | 2015089486 A2 | 6/2015 |
| WO | 2016049163 A2 | 3/2016 |
| WO | 2016083360 A1 | 6/2016 |
| WO | 2016187717 A1 | 12/2016 |

OTHER PUBLICATIONS

Garcia-Bloj et al. (Oncotarget, 7, 37, 2016, 60535-60554).*
Senis et al. (Biotechnol. J. 2014, 9, 1402-1412).*
U.S. Appl. No. 16/479,177, Non-Final Office Action, Mailed on Jan. 25, 2022, 14 pages.
U.S. Appl. No. 16/479,177, "Notice of Allowability", Jul. 27, 2022, 5 pages.
U.S. Appl. No. 16/479,177, Notice of Allowance, Mailed on Jul. 7, 2022, 8 pages.
Application No. EP18750827.0, Extended European Search Report, Mailed on Nov. 20, 2020, 15 pages.
Jin et al., "Generation of Genetically Modified Mice Using CRISPR/Cas9 and Haploid Embryonic Stem Cell Systems", Zoological Research, vol. 37, No. 4, Jul. 18, 2016, pp. 205-213.
Application No. JP2019-542540, Office Action, Mailed on Oct. 12, 2022, 8 pages.
Li et al., "An Episomal Crispr/Cas9 System to Derive Vector-Free Gene Modified Mammalian Cells", Protein Cell, vol. 7, No. 9, Sep. 2016, pp. 689-691.
Matharu et al., "Crispr-Mediated Activation of a Promoter or Enhancer Rescues Obesity Caused by Haploin Sufficiency", Science, vol. 363, No. 6424, XP0557 48390, Dec. 13, 2018, pp. 1-30.
Application No. PCT/US2018/017186, International Preliminary Report on Patentability, Mailed on Aug. 22, 2019, 11 pages.
Application No. PCT/US2018/017186, International Search Report and Written Opinion, Mailed on Jun. 6, 2018, 16 pages.
PCT/US2018/017186, "Invitation to Pay Add'l Fees and Partial Search Report", Apr. 10, 2018, 3 pages.

\* cited by examiner

*Primary Examiner* — Amy Rose Hudson
(74) *Attorney, Agent, or Firm* — Kilpatrick Townsend & Stockton LLP

(57) ABSTRACT

Methods and compositions are provided for activating transcription in a mammalian cell.

6 Claims, 23 Drawing Sheets

Specification includes a Sequence Listing.

Female

Male

Sim1+/- Prm-CRISPa Wildtype

| 10cm | 9.5cm | 9cm | Length |
|---|---|---|---|
| 43gms | 31gms | 24gm | Weight |

Sim1+/- Enh-CRISPa Wildtype

| 11cm | 10cm | 10cm | Length |
|---|---|---|---|
| 41gm | 28ms | 25gmS | Weight |

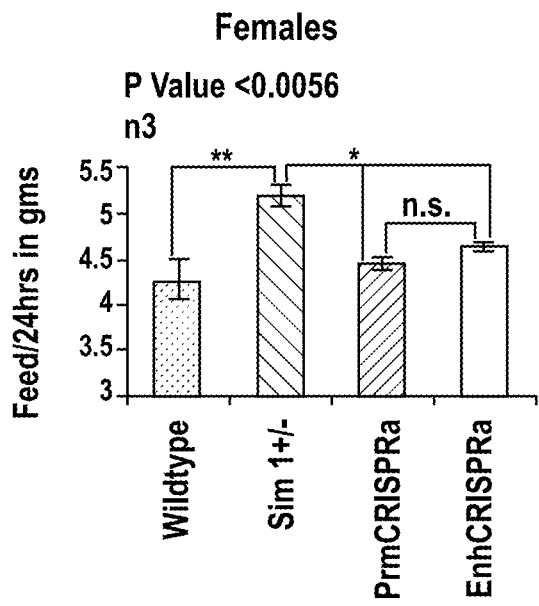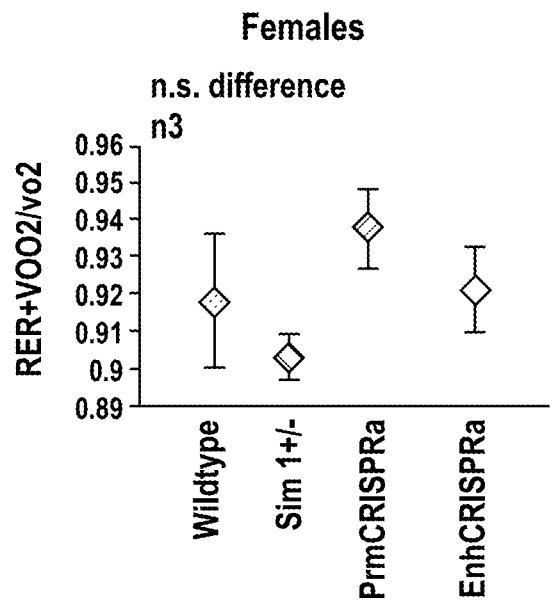
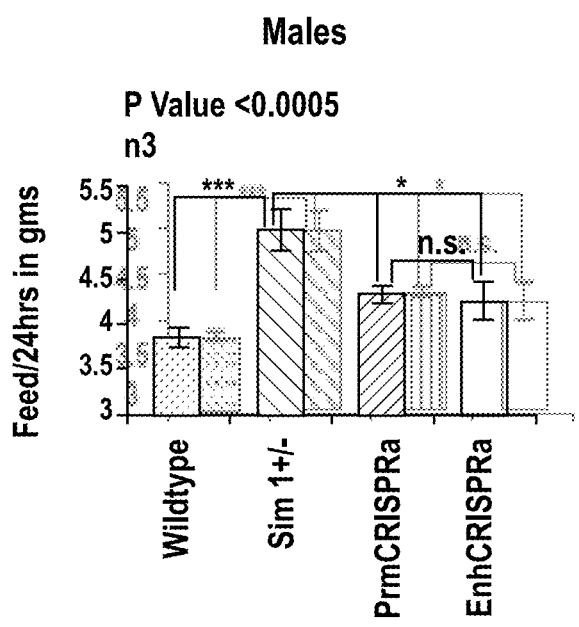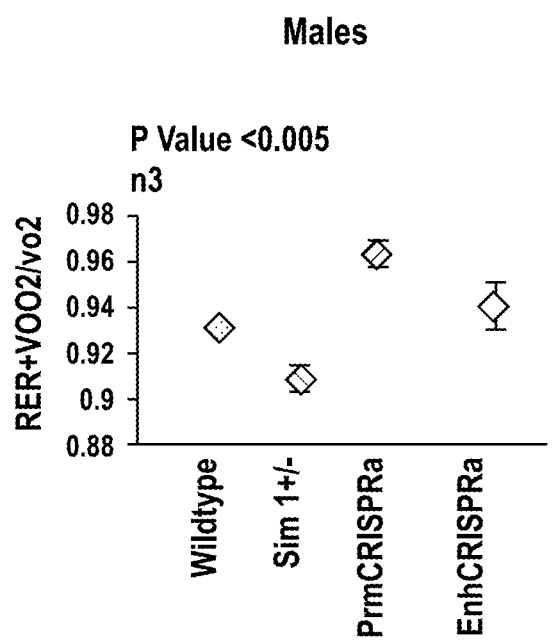
FIG. 2C  FIG. 2D

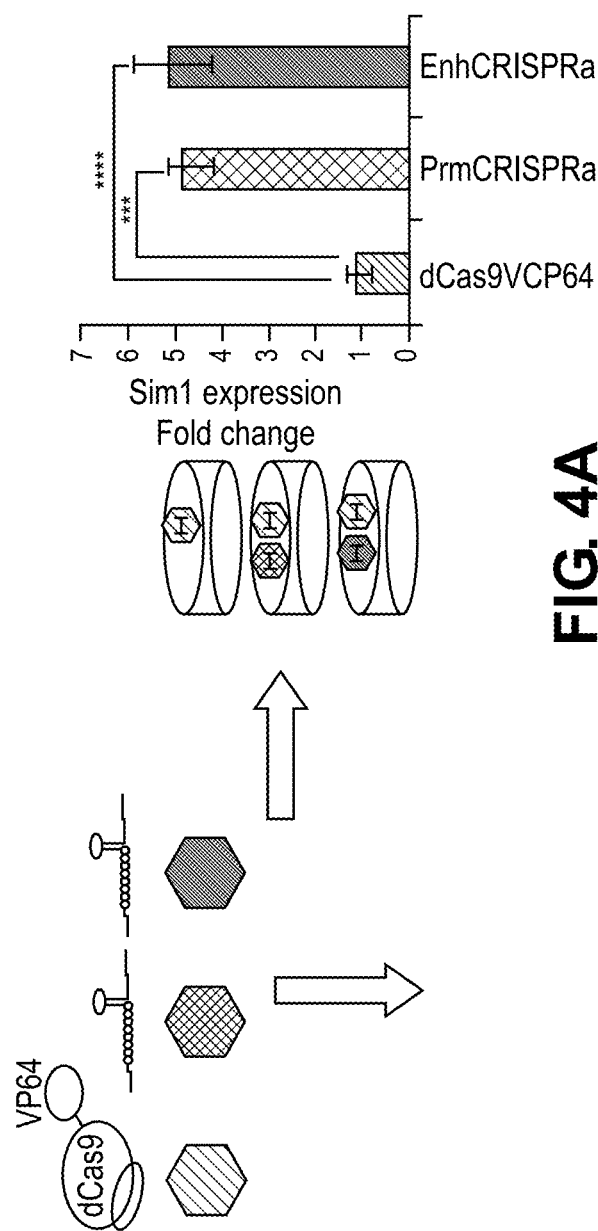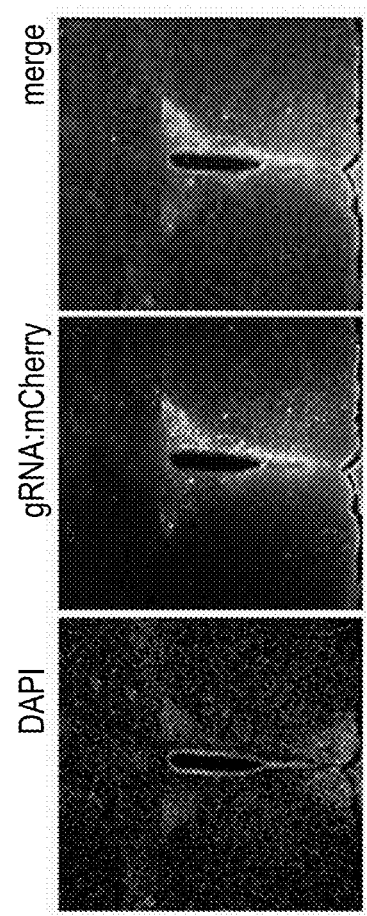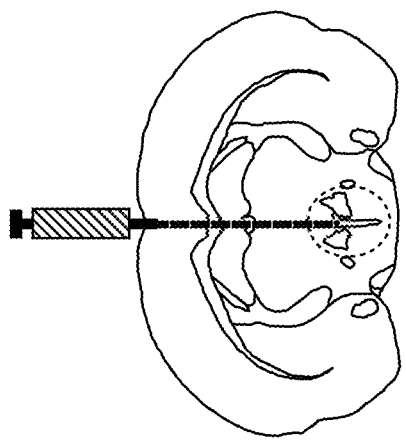
FIG. 4A
FIG. 4B
FIG. 4C

GENE THERAPY FOR HAPLOINSUFFICIENCY

CROSS-REFERENCE TO RELATED APPLICATIONS

This application is a divisional of U.S. patent application Ser. No. 16/479,177, filed Jul. 18, 2019; which is a 371 U.S. National Phase Application of PCT/US2018/017186, filed Feb. 7, 2018, which claims benefit of priority to U.S. Provisional Application No. 62/455,988, filed Feb. 7, 2017, the contents of which are hereby incorporated by reference in their entireties for all purposes.

STATEMENT AS TO RIGHTS TO INVENTIONS MADE UNDER FEDERALLY SPONSORED RESEARCH AND DEVELOPMENT

This invention was made with government support under grant No. R01 DK090382 awarded by The National Institutes of Health. The government has certain rights in the invention.

REFERENCE TO SUBMISSION OF A SEQUENCE LISTING

This application includes a Sequence Listing as an XML file named 081906-224420US-1353476_SL.xml created Apr. 28, 2023 and containing 102,820 bytes. The material contained in this XML file is incorporated by reference in its entirety for all purposes.

FIELD OF INVENTION

The present disclosure relates generally to methods and compositions for activating transcription in mammalian cells.

BACKGROUND OF THE INVENTION

Genomic alterations resulting in reduced transcription or activity of one or more genes or gene products are a causative factor in a myriad of mammalian diseases. One such genomic alteration is haploinsufficiency, in which there is only one functional copy of a gene and that single copy does not produce enough of the gene product to produce a wild-type phenotype. Other diseases are caused by genomic alterations in one or both copies of a gene that alter the gene product so that it exhibits a reduction, but not elimination, in activity. In still other diseases, genomic alterations reduce transcription or reduce transcript stability of one or both copies of a gene, such that there is insufficient gene product to produce a wild-type phenotype. Numerous approaches have been attempted to treat such diseases by augmenting the amount or activity of the one or more genes reduced in transcription or activity. Such approaches include delivery into the genome of a wild-type copy of the one or more genes. Recently, targeted introduction into a genome has been demonstrated using methods and compositions based on clustered regularly interspaced short palindromic repeats (CRISPR), Zinc Finger Nucleases (ZFNs) (see, Urnov et al., *Nat. Rev. Genet.*, 11:636-646 (2010) or transcription activator-like effector nucleases (TALENs) (see, Joung and Sander, *Nat. Rev. Mol. Cell Biol.*, 1:49-55 (2013). Other approaches for increasing transcription of one or more target genes include the use of antisense oligomers that promote constitutive splicing (see, US 2016/0298121). However, there remains a need for alternative methods and compositions for increasing the transcription of target genes to treat diseases caused by their reduced transcription, amount, or activity.

BRIEF SUMMARY OF THE INVENTION

The present invention is directed to methods and compositions for increasing transcription of target genes in a mammalian (e.g., human) subject. The inventors have discovered that such increased transcription can be achieved with a transcription-activating guide-RNA (gRNA) construct (e.g., as part of a dCAS9/gRNA complex) targeted to a promoter or enhancer region of a gene. Moreover, the inventors have discovered that transcriptional activation in amounts and for periods of time that are sufficient to treat a disease can be achieved with a non-integrating vector. In some cases, the methods and compositions for transcriptional activation do not covalently modify the genome of the host mammal by endonuclease cleavage, nicking, and/or repair. In some cases, the non-integrating vector is an episomal vector, such as an adeno associated viral vector.

In one aspect, the present invention provides a method of treating a haploinsufficiency disease in a mammalian subject, the method comprising contacting a cell of the subject with a composition comprising: i) a guide RNA, wherein the guide RNA comprises: a) a targeting region that, under conditions present in a nucleus of the cell, specifically hybridizes to a promoter region or an enhancer region operably linked to a wild-type copy of a haploinsufficient gene; and b) a CRISPR nuclease-binding region that specifically binds a CRISPR nuclease under conditions present in a nucleus of the cell or a region that specifically binds to the CRISPR nuclease-binding region; and ii) the CRISPR nuclease, —wherein the contacting forms a complex comprising the CRISPR nuclease bound to the guide RNA, wherein the targeting region of the guide RNA in the complex is hybridized to the promoter or enhancer; —wherein the complex comprises a catalytically inactive CRISPR nuclease and a transcriptional activation domain, and—wherein the complex activates transcription of the wild-type copy of the haploinsufficient gene in an amount and for a duration sufficient to treat the haploinsufficiency disease in the subject. In some embodiments, the mammalian subject is treated with a host cell obtained from the subject. In one embodiment, the mammalian subject is treated with a host cell obtained from a different (distinct) mammalian subject. In some embodiments, the host cell is an isolated mammalian host cell. In another embodiment, the host cell comprises an isolated mammalian host cell having one functional copy of a target gene.

In some embodiments, the contacting comprises contacting the cell with an episomal vector encoding the guide RNA or the CRISPR nuclease. In some embodiments, the contacting comprises contacting the cell with an episomal vector encoding the guide RNA and the CRISPR nuclease. In some embodiments, the contacting comprises contacting the cell with an episomal vector encoding the guide RNA and a second episomal vector encoding the CRISPR nuclease. In some embodiments, the episomal vector(s) are non-integrating. In some embodiments, the episomal vector(s) are non-replicating. In some embodiments, the episomal vector(s) are adeno-associated virus (AAV) vectors. In some embodiments, the episomal vector(s) independently comprise a first and a second end, wherein the first end and second end each independently comprise an AAV inverted terminal repeat.

In some embodiments, the CRISPR nuclease comprises (i) a nuclease domain that has been modified to eliminate nuclease and nicking activity and (ii) a transcriptional activation domain. In some embodiments, the CRISPR nuclease comprises a Cas9 or Cpf1 nuclease. In some embodiments, the modification comprises a mutation at positions corresponding to D10 and H840 of *S. pyogenes* Cas9. In some embodiments, the CRISPR nuclease comprises a D10A, H840A *S. pyogenes* dCas9. In some embodiments, the CRISPR nuclease comprises a *S. aureus* dCas9. In some embodiments the *S. aureus* dCas9 comprises one or more mutations in one of the following residues: E782, K929, N968, R1015. In some embodiments, the guide RNA comprises a dead guide sequence.

In some embodiments, the guide RNA comprises a transcriptional activation binding domain, wherein the transcriptional activation binding domain specifically binds a composition comprising one or more transcriptional activation domains. In some embodiments, the complex comprising the CRISPR nuclease bound to the guide RNA further comprises a transcriptional activation domain selected from the group consisting of HSF1, VP16, VP64, p65, MyoD1, RTA, SET7/9, VPR, histone acetyltransferase p300, an hydroxylase catalytic domain of a TET family protein (e.g., TET1 hydroxylase catalytic domain), LSD1, CIB1, AD2, CR3, EKLF1, GATA4, PRVIE, p53, SP1, MEF2C, TAX, and PPARγ. In some embodiments, the CRISPR nuclease is a CRISPR nuclease-VP64 fusion polypeptide.

In some embodiments, the guide RNA comprises a scaffold region. In some embodiments, the scaffold region comprises an ms2, f6, PP7, com, or L7a ligand sequence. In some embodiments, the scaffold region of the guide RNA in the complex is bound to a transcriptional activation domain fused to an MCP polypeptide, a COM polypeptide, a PCP polypeptide, or an L7a polypeptide. In some embodiments, the haploinsufficient gene is SIM1, Leptin, Leptin receptor, MC4R, SCN2A, SETD5, PAX6, PKD1, MC3R, POMC, STAT3, STAT5, SOCS3, GHR, NPY, NPY1R, NPY2R, NPY5R, PYY, AMPK (PRKAA1, PRKAA2, PRKAB1, PRKAB2, PRKAG1, PRKAG2, PRKAG3), OXT, JAK2, SHP2, NOS3, NROB2, BRS3, CARTPT, FABP4, HTR2C, IL6, NHLH2, NMU, NPB, NPBWRI, PNPLA2, UCP3, ADIPOQ, APOA5, ARNT2, ASIP, CIQTNF2, C3AR1, CCK, CPT1B, CSF2, DGAT1, DGAT2, GHRL, GHSR, HSD11B1, HTR7, INSIG1, INSIG2, LIPC, NMUR1, NMUR2, NPBWR2, NTS, PPARGC1A, PPY, RETN, SIRT1, TGFBR2, WDTC1, or FOXO1.

In some embodiments, the targeting region of the guide RNA is encoded by or specifically hybridizes to: SEQ ID NO:1 (GACACGGAATTCATTGCCAG), SEQ ID NO:2 (CTGCGGGTTAGGTCTACCGG), SEQ ID NO:3 (GTTGAGCGCTCAGTCCAGCG), SEQ ID NO:4 (TCCCGACGTCGTGCGCGACC), or SEQ ID NO:5 (GCTCTGAATCTTACTACCCG). In some embodiments, the targeting region of the guide RNA is encoded by or specifically hybridizes to: SEQ ID NO:6 (GCTGTTAACTAAAGACAGGG), SEQ ID NO:7 (GTGGTCTGGGTGATCTCATG), SEQ ID NO:8 (GACAAAGGAACATCTGAGAGG), SEQ ID NO:9 (GTGATCTCATGGGGAAGAGG), or SEQ ID NO:10 (GGCTTTGATCGTGGTCTGGG). In some embodiments, the targeting region of the guide RNA is encoded by or specifically hybridizes to: SEQ ID NO:11 (GCGAGCCCAGTCGCGTGGGG), or SEQ ID NO:12 (GCCAAGAATTGGCCAAAGGG), SEQ ID NO:34 (GTCAAAGGGGCATATGGAAGG), SEQ ID NO:35 (GGGAAGAAAGCCCCACTTGG), SEQ ID NO:36 (GCCCAGTCGCGTGGGGGGGG), or SEQ ID NO:37 (GGAGCGCGAGTGTCACTCGG). In another embodiment, the targeting region of the guide RNA is encoded by or specifically hybridizes to: SEQ ID NO:38 (GCTCACTGTAGGACCCGAGCC), SEQ ID NO:39 (GACGCGGCGCTCATTGGCCAA), SEQ ID NO:40 (CGAGCCGCGAGCCCAGTCGCG), SEQ ID NO:41 (TCCCCCCCCCCCCCCACGCGA), SEQ ID NO:42 (GTCACTCACCCCGATTGGCCA), or SEQ ID NO:43 (CGCGAGCCCAGTCGCGTGGGG). In some embodiments, the targeting region of the guide RNA is encoded by or specifically hybridizes to: SEQ ID NO:44 (GTTGGCTTATCCAAACATCTC), SEQ ID NO:45 (ATGTTAAGCAAGGGTAATAGA), SEQ ID NO:46 (CTGTGAAAGGAATACAATTCA), SEQ ID NO: 47 (GCCAATTCTTGGCAACCGAGC), SEQ ID NO:48 (GAATTGGCCAAAGGGAGGGGT), or SEQ ID NO:49 (AATTAGCAGACAGCTTGGTAC). In some embodiments, the targeting region of the guide RNA is encoded by or specifically hybridizes to: SEQ ID NO:50 (CTGGCTGATTCCCGAGGATTT), SEQ ID NO:51 (CACTGAATACGGATTGGTCAG), SEQ ID NO:52 (GATGTCTCAGAACCACTGAAT), SEQ ID NO:53 (AACCACTGAATACGGATTGGT), or SEQ ID NO:54 (ACCAATCCGTATTCAGTGGTT). In some embodiments, the targeting region of the guide RNA is encoded by or specifically hybridizes to: SEQ ID NO:55 (GGCGCGGGGCGGACGGGGCGA), SEQ ID NO:56 (GCGCCCGGGAACGCGTGGGG), SEQ ID NO:57 (CGCCCCGCGCCGCGCGGGGAG), SEQ ID NO:58 (TCCGCCCCGCGCCGCGCGGGG), SEQ ID NO:59 (GGAACGCGTGGGGCGGAGCTT), SEQ ID NO:60 (GCCCCGCGCCGCGCGGGGAGG), SEQ ID NO:61 (TGCGCCCCGGGAACGCGTGGG), SEQ ID NO:62 (GAACGCGTGGGGCGGAGCTTC), SEQ ID NO:63 (GCGGCGCGGGGCGGACGGGGC), or SEQ ID NO:64 (CCCGTCCGCCCCGCGCCGCGC). In some embodiments, the targeting region of the guide RNA is encoded by or specifically hybridizes to: SEQ ID NO:65 (GGCCCACTCGCCGCCAATCAG), SEQ ID NO:66 (GGAAGCCGCCGGGGCCGCCTA), SEQ ID NO:67 (TGATTGGCGGCGAGTGGGCCA), SEQ ID NO:68: (GCCGCCAATCAGCGGAAGCCG), SEQ ID NO:69: (GGCGGCTTCCGCTGATTGGCG), SEQ ID NO:70: (CCGCCAATCAGCGGAAGCCGC), SEQ ID NO:71: (AGCCGCCGGGGCCGCCTAGAG), SEQ ID NO:72: (GCTTCCGCTGATTGGCGGCGA), SEQ ID NO:73: (CGGCGAGTGGGCCAATGGGTG), or SEQ ID NO:74: (CCAATGGGTGCGGGCGGTGG). In some embodiments, the targeting region of the guide RNA is encoded by or specifically hybridizes to: SEQ ID NO:75 (GGCTGCCGGGGCCGCCTAAAG), SEQ ID NO:76 (GGAGGCTGCCGGGGCCGCCTA), SEQ ID NO:77 (GCCGCCAATCAGCGGAGGCTG), SEQ ID NO:78 (CCGCCAATCAGCGGAGGCTGC), SEQ ID NO:79 (TGGCCGGTGCGCCGCCAATCA), SEQ ID NO:80 (GGCCGGTGCGCCGCCAATCAG), SEQ ID NO:81 (CGGCGCACCGGCCAATAAGTG), SEQ ID NO:82 (ATAAGTGTGGGGCGGTGGGCG), SEQ ID NO:83 (CCAATAAGTGTGGGGCGGTGG), or SEQ ID NO:84 (CAATAAGTGTGGGGCGGTGGG). In some embodiments, the targeting region of the guide RNA is encoded by or specifically hybridizes to: SEQ ID NO:85 (CCTTTCTATGACCTAGTCGG), SEQ ID NO:86 (CAGAATCAGTAACGCACTGT), SEQ ID NO:87 (GAAACCAGGAGAGATAACCC), SEQ ID NO:88 (GGACCCCAGATATTCTGGAA), SEQ ID NO:89 (TTAT- TGTTGACTTAACGAAG), SEQ ID NO:90 (AAAAAGAAGCAAATAGCTAA), or SEQ ID NO:91 (AGAATCAGTAACGCACTGTA). In some embodiments, the targeting region of the guide RNA is encoded by or specifically hybridizes to: SEQ ID NO:92 (TGTTGGTTT-ATTGGACCCCAGATATTC), SEQ ID NO:93 (TGTTG-GAGAAAATTAACTTAGTGCATA), or SEQ ID NO:94 (TGTTGGTATAACTGCCACTAGAGGGCT). In some embodiments, the targeting region of the guide RNA is encoded by or specifically hybridizes to SEQ ID NO:95 (AGGAGCCGGGACCCACCGG).

In some embodiments, the cell is a non-dividing cell. In some embodiments, the cell is a neuron. In some embodiments, the cell is a hypothalamus cell. In some embodiments, the contacting comprises injection of nucleic acid encoding the guide RNA and/or the CRISPR nuclease into a region of a brain containing a hypothalamus. In some embodiments, the contacting comprises injection of an adeno-associated viral vector comprising nucleic acid encoding the guide RNA and/or the CRISPR nuclease into a region of a brain containing a hypothalamus. In some embodiments, the haploinsufficiency disease is selected from Table 1. In some embodiments, the haploinsufficiency disease is selected from obesity, autism, epilepsy, intellectual disability, aniridia, and polycystic kidney disease. In some embodiments, the haploinsufficiency disease is obesity.

In another aspect, the present invention provides a mammalian host cell comprising: I.) a genome comprising at least one functional copy of a target gene, wherein the functional cop(y/ies) in the absence of transcriptional activation by a heterologous complex do not produce enough of a corresponding gene product to produce a wild-type phenotype in an organism; and II.) the heterologous complex, wherein the heterologous complex comprises: a) a guide RNA, wherein the guide RNA comprises: i.) a targeting region that specifically hybridizes to a promoter region or an enhancer region operably linked to the functional cop(y/ies) of the target gene under conditions present in a nucleus of the cell; and ii.) a CRISPR nuclease-binding region that specifically binds a CRISPR nuclease under conditions present in a nucleus of the cell; and b) the CRISPR nuclease, —wherein the guide RNA of the heterologous complex comprising the CRISPR nuclease bound to the guide RNA is hybridized to the promoter or enhancer; —wherein the CRISPR nuclease is catalytically inactive, and—wherein the complex activates transcription of the functional cop(y/ies) of the target gene in an amount and for a duration sufficient to produce a wild-type phenotype when the host cell is present in an organism.

In some embodiments, the genome comprises a single functional copy of the target gene. In some embodiments, the single functional copy of the target gene comprises a haploinsufficient gene. In some embodiments, the genome comprises less than two functional copies of the target gene.

BRIEF DESCRIPTION OF THE DRAWINGS

FIGS. 2A-2D Body composition and metabolic analyses of Sim1 CRISPRa transgenic mice. A, Estimated percent fat in wild-type littermates, Sim1$^{+/-}$, H11P$^{CAG-dCas9-VP64}$×ROSA26Sim1Pr-sgRNA (PrmCRISPRa) and H11P$^{CAG-dCas9-VP64}$×ROSA26$^{SCE2En-sgRNA}$ (EnhCRISPRa) as determined by Dual Energy X-ray Absorptiometry (DEXA) or Echo Magnetic Resonance Imaging (EchoMRI), with their corresponding body weight measurements. The mean values±s.d. were obtained from 3 females and 3 males. B, Metabolic chamber energy expenditure analyses for 3 males and 3 females for all four genotypes determined over a 4 day period. C, Food intake for all four genotypes determined over a 4 day period. Mean values±s.d. were obtained from 3 females and 3 males. *=p-value< 0.001; ***=p-value<0.0005; n.s=non-significant (ANOVA, Tukey test). D, Respiratory exchange ratio (RER; VCO2/VO2) for all four genotypes obtained from 3 females and 3 males and plotted as mean values±s.d.

FIGS. 4A-4E CRISPRa Sim1 overexpression in vitro and in vivo using AAV. A, AAV CRISPRa in Neuro-2A cells using virons containing: pCMV-dCas9-VP64 (dCas9-VP64), pCMV-dCas9-VP64 along with pSim1Pr-mCherry (PrmCRIPSRa) and pCMV-dCas9-VP64 along with pSCE2En-mCherry (EnhCRISPRa). Results are expressed as mRNA fold-increase normalized to beta-actin using the ΔΔCT method. The mean values±s.d. were obtained from 3 independent experiments. ***=p-value<0.0005 (ANOVA, Tukey test). B, Schema showing the PVN injected region. C, Immunohistochemistry of pSim1Pr-mCherry injected hypothalamus from 20 week old mice showing mCherry expression in the PVN. D-E, Cas9 (d) and Sim1 (e) mRNA expression from pCMV-dCas9-VP64 (dCas9-VP64), pCMV-dCas9-VP64+pSim1Pr-mCherry (PrmCRIPSRa, n=3) and pCMV-dCas9-VP64+pSCE2En-mCherry (EnhCRISPRa, n=4) from injected mice. The mean values±s.d were determined based on mRNA fold-increase compared to Sim1$^{+/-}$ mice and normalized to beta-actin using the ΔΔCT method.

FIG. 7A, shows an exemplary *S. aureus* CRISPRa system targeting the Sim1 promoter (Pr) by transfection of various sgRNA's (SEQ ID NOS:38-43) into Neuro-2A (N2A) cells. Results are expressed as mRNA fold-increase normalized to Sa-dCas9-VP64. The mean values±s.d. were obtained from 3 independent experiments. FIG. 7B, shows an exemplary *S. aureus* CRISPRa in N2A cells targeting the Sim1 promoter (Pr) after infection of AAV's containing select sgRNA's (SEQ ID NOS:38, 40, or 42) into N2A cells. Results are expressed as mRNA fold-increase normalized to VP64 alone. The mean values±s.d. were obtained from 3 independent experiments.

FIG. 8A, shows an exemplary *S. aureus* CRISPRa system targeting the Sim1 SCE2 enhancer (Enh) by transfection of various sgRNA's (SEQ ID NOS:44-49) into N2A cells. Results are expressed as mRNA fold-increase normalized to Sa-dCas9-VP64. The mean values±s.d. were obtained from 3 independent experiments. FIG. 8B, shows an exemplary *S. aureus* CRISPRa system targeting the Sim1 SCE2 enhancer (Enh) after infection of AAV's containing select sgRNA's (SEQ ID NOS:45, 46, or 47) into N2A cells. Results are expressed as mRNA fold-increase normalized to VP64 alone. The mean values±s.d. were obtained from 3 independent experiments.

FIG. 9A, shows an exemplary *S. aureus* CRISPRa system targeting the Mc4r promoter (Pr) by transfection of various sgRNA's (SEQ ID NOS:50-54) into N2A cells. Results are expressed as mRNA fold-increase normalized to VP64. The mean values±s.d. were obtained from 3 independent experiments. FIG. 9B, shows an exemplary *S. aureus* CRISPRa system targeting the Mc4r promoter (Pr) after infection of AAV's containing select sgRNA's (SEQ ID NOS:51, 52, or 54) into N2A cells. Results are expressed as mRNA fold-increase normalized to VP64. The mean values±s.d. were obtained from 3 independent experiments.

FIG. 11A, shows an exemplary *S. aureus* CRISPRa system targeting the SETD5 promoter (Pr) or THUMPD3 by transfection of human promoter sgRNA's (SEQ ID NOS:65-74) into human HEK293T cells. HS MIX refers to transfection of an equimolar concentration of each of HS01-HS10 into human HEK293T cells. Results are expressed as mRNA fold-increase normalized to VP64 alone. The mean values±s.d. were obtained from 3 independent experiments. FIG. 11B, shows an exemplary *S. aureus* CRISPRa system targeting the SETD5 promoter (Pr) or ROSA26 by transfection of mouse promoter sgRNA's (SEQ ID NOS:75-84) into mouse Neuro-2A cells. MS MIX refers to transfection of an equimolar concentration of each of MS01-MS10 into mouse Neuro-2A cells. Results are expressed as mRNA fold-increase normalized to VP64 alone. The mean values±s.d. were obtained from 3 independent experiments.

FIG. 12A, shows an exemplary *S. pyogenes* (Sp) Cas9 CRISPRa system targeting the Scn2a promoter (Pr) by transfection of various sgRNA's (SEQ ID NOS:85-91) into N2A cells. Results are expressed as mRNA fold-increase normalized to VP64 alone. The mean values±s.d. were obtained from 3 independent experiments. FIG. 12B, shows an exemplary *S. aureus* CRISPRa system targeting the Scn2a promoter (Pr) after infection of AAV's containing select sgRNA's (SEQ ID NOS:92-94) into N2A cells. Two different multiplicity of infection (MOI) were used: 5,000 and 1,250 viral genome (vg/ml). Results are expressed as mRNA fold-increase normalized to VP64 alone. The mean values±s.d. were obtained from 3 independent experiments.

DEFINITIONS

Figure 1A:
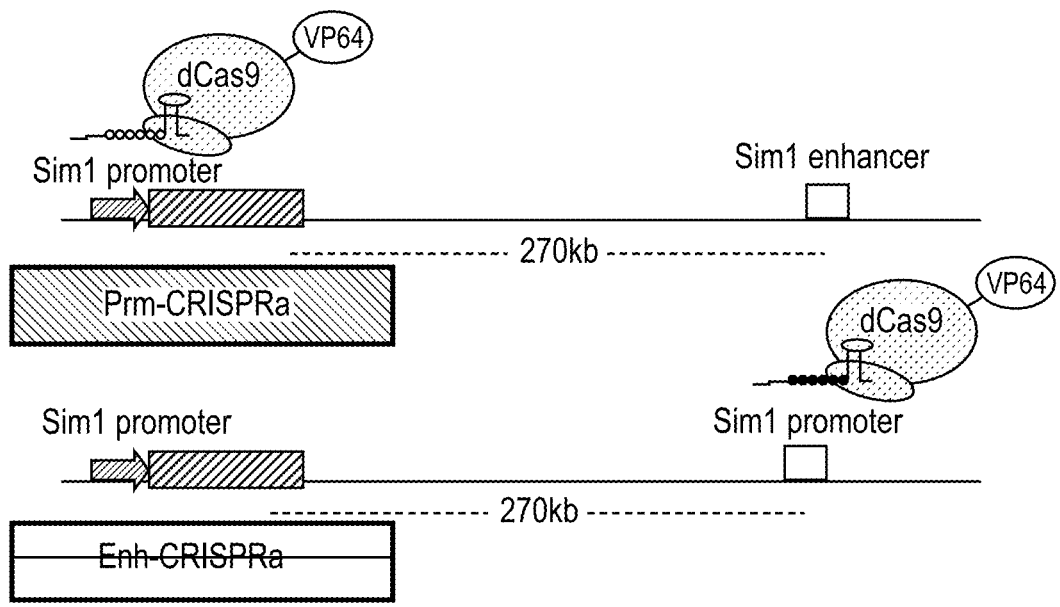
FIGS. 1A-IF: Transgenic CRISPRa Sim1 overexpression in vitro and in vivo. A, Schema of the mouse Sim1 genomic locus. B, CRISPRa in Neuro-2A cells targeting the Sim1 promoter (Pr) or enhancer (Enh). Results are expressed as mRNA fold-increase normalized to beta-actin using the ΔΔCT method. The mean values±s.d. were obtained from 3 independent experiments. *=p-value<0.001***=p-value<0.0005 (ANOVA, Tukey test). C, Schema showing the various mouse lines and mouse transgenic CRISPRa concept. D, Weekly weight measurements of wild-type littermates, Sim1$^{+/-}$, H11P$^{CAG-dCas9-VP64}$×ROSA26$^{Sim1Pr-sgRNA}$ and H11P$^{CAG-dCas9-VP64}$×ROSA26$^{SCE2En-sgRNA}$. At least 10 male and female mice were measured per genotype. Mean values±s.d are shown. E-F, Pictures showing 20 week old mice for each genotype: Sim1$^{+/-}$, H11P$^{CAG-dCas9-VP64}$×ROSA26$^{Sim1Pr-sgRNA}$ and wild-type littermate (E) and Sim1$^{+/-}$, H11P$^{CAG-dCas9-VP64}$×ROSA26$^{SCE2En-sgRNA}$ and wild-type littermate (F). Length and weight of each mice are depicted above and below respectively.

As used in this specification and the appended claims, the singular forms "a," "an," and "the" include plural reference unless the context clearly dictates otherwise.

"Treating" refers to any indicia of success in the treatment or amelioration or prevention of the disease, condition, or disorder, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with a disease, condition or disorder as described herein. The term "therapeutic effect" refers to the reduction, elimination, or prevention of the disease, symptoms of the disease, or side effects of the disease in the subject. "Treating" or "treatment" using the methods of the present invention includes preventing the onset of symptoms in a subject that can be at increased risk of a disease or disorder associated with a disease, condition or disorder as described herein, but does not yet experience or exhibit symptoms, inhibiting the symptoms of a disease or disorder (slowing or arresting its development), providing relief from the symptoms or side-effects of a disease (including palliative treatment), and relieving the symptoms of a disease (causing regression). Treatment can be prophylactic (to prevent or delay the onset of the disease, or to prevent the manifestation of clinical or subclinical symptoms thereof) or therapeutic suppression or alleviation of symptoms after the manifestation of the disease or condition. The term "treatment," as used herein, includes preventative (e.g., prophylactic), curative or palliative treatment.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologues, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al, Mol. Cell. Probes 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter.

A "reporter gene" encodes proteins that are readily detectable due to their biochemical characteristics, such as enzymatic activity or chemifluorescent features. One specific example of such a reporter is green fluorescent protein. Fluorescence generated from this protein can be detected with various commercially-available fluorescent detection systems. Other reporters can be detected by staining. The reporter can also be an enzyme that generates a detectable signal when contacted with an appropriate substrate. The reporter can be an enzyme that catalyzes the formation of a detectable product. Suitable enzymes include, but are not limited to, proteases, nucleases, lipases, phosphatases and hydrolases. The reporter can encode an enzyme whose substrates are substantially impermeable to eukaryotic plasma membranes, thus making it possible to tightly control signal formation. Specific examples of suitable reporter genes that encode enzymes include, but are not limited to, CAT (chloramphenicol acetyl transferase; Alton and Vapnek (1979) Nature 282: 864-869); luciferase (lux); 0-galactosidase; LacZ; β.-glucuronidase; and alkaline phosphatase (Toh, et al. (1980) Eur. J. Biochem. 182: 231-238; and Hall et al. (1983) J. Mol. Appl. Gen. 2: 101), each of which are incorporated by reference herein in its entirety. Other suitable reporters include those that encode for a particular epitope that can be detected with a labeled antibody that specifically recognizes the epitope.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups {e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

There are various known methods in the art that permit the incorporation of an unnatural amino acid derivative or analog into a polypeptide chain in a site-specific manner, see, e.g., WO 02/086075.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. In some cases, conservatively modified variants of a CRISPR nuclease such as Cas9 or a guide RNA such as a small guide RNA (sgRNA) can have an increased stability, assembly, or activity as described in WO 2016/011080, the contents of which are hereby incorporated by reference in the entirety for all purposes including, without limitation, the sgRNAs, sgRNA scaffolds, sgRNA libraries, and sgRNA binding regions described therein.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins, W. H. Freeman and Co., N. Y. (1984)).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In the present application, amino acid residues are numbered according to their relative positions from the left most residue, which is numbered 1, in an unmodified wild-type polypeptide sequence.

As used in herein, the terms "identical" or percent "identity," in the context of describing two or more polynucleotide or amino acid sequences, refer to two or more sequences or subsequences that are the same or have a specified percentage of amino acid residues or nucleotides that are the same. For example, a core small guide RNA (sgRNA) sequence responsible for assembly and activity of a sgRNA: nuclease complex has at least 80% identity, preferably 85%, 90%, 91%, 92%, 93, 94%, 95%, 96%, 97%, 98%, 99%, or 100%) identity, to a reference sequence, when compared and aligned for maximum correspondence over a comparison window, or designated region as measured using one of the following sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Current Protocols in Molecular Biology (Ausubel et al., eds. 1995 supplement)).

Examples of algorithms that are suitable for determining percent sequence identity and sequence similarity are the BLAST and BLAST 2.0 algorithms, which are described in Altschul et al, (1990) J. Mol. Biol. 215: 403-410 and Altschul et al. (1977) Nucleic Acids Res. 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, Proc. Natl. Acad. Sci. USA 89: 10915 (1989)).

The BLAST algorithm also performs a statistical analysis of the similarity between two sequences {see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence. Yet another indication that two polypeptides are substantially identical is that the two polypeptides retain identical or substantially similar activity.

A "translocation sequence" or "transduction sequence" refers to a peptide or protein (or active fragment or domain thereof) sequence that directs the movement of a protein from one cellular compartment to another, or from the extracellular space through the cell or plasma membrane into the cell. Translocation sequences that direct the movement of a protein from the extracellular space through the cell or plasma membrane into the cell are "cell penetration peptides." Translocation sequences that localize to the nucleus of a cell are termed "nuclear localization" sequences, signals, domains, peptides, or the like.

Examples of translocation sequences include, without limitation, the TAT transduction domain (see, e.g., S. Schwarze et al, Science 285 (Sep. 3, 1999); penetratins or penetratin peptides (D. Derossi et al, Trends in Cell Biol. 8, 84-87); Herpes simplex virus type 1 VP22 (A. Phelan et al., Nature Biotech. 16, 440-443 (1998), and polycationic (e.g., poly-arginine) peptides (Cell Mol. Life Sci. 62 (2005) 1839-1849). Further translocation sequences are known in the art. Translocation peptides can be fused (e.g. at the amino or carboxy terminus), conjugated, or coupled to a compound of the present invention, to, among other things, produce a conjugate compound that may easily pass into target cells, or through the blood brain barrier and into target cells.

As used herein, the term "CRISPR" refers to any one of the naturally occurring Clustered Regularly Interspaced Short Palindromic Repeat systems or loci, or a derivative thereof. CRISPR loci can be found in the genomes of many bacteria and archaea. There are four types of CRISPR systems (e.g., Type I, Type II, Type III, and Type U).

A CRISPR locus can comprise polynucleotide sequences encoding for CRISPR Associated Genes (Cas) genes. Cas genes can be involved in the biogenesis and/or the interference stages of crRNA function. Cas genes can be named according to the organism from which they are derived. For example, Cas genes in *Staphylococcus epidermidis* can be referred to as Csm-type, Cas genes in *Streptococcus thermophilus* can be referred to as Csn-type, and Cas genes in *Pyrococcus furiosus* can be referred to as Cmr-type.

As used herein, the term CRISPR nuclease refers to a polypeptide of, or derived from, a nuclease encoded in any one of the four types of CRISPR loci: Type I, Type II, Type III, and Type U, wherein the natural sequence of the polypeptide exhibits RNA-guided nuclease activity. A CRISPR nuclease can be catalytically inactive. Catalytically inactive CRISPR nucleases do not exhibit nuclease or nickase activity when in complex with an RNA-guide and bound to a nucleic acid target containing a target domain and, in certain embodiments, a PAM sequence. The catalytically inactive CRISPR nuclease can be catalytically inactive due to one or more mutations of the CRISPR nuclease polypeptide sequence, or due to forming a complex with a guide RNA that is sufficient to provide RNA-guided targeting, but insufficient to support catalytic activity (i.e., nuclease or nicking activity). For example, the CRISPR nuclease can be a wild-type CRISPR nuclease (e.g., a Cas9 or Cpf1 nuclease) in complex with a dead guide sequence. For example, Cpf1 is a Class II CRISPR-Cas system and is described in Zetsche et al., *Cell*, 163:759-771 (2015). Dead guide sequences and their use are further described in, e.g., WO 2016/094872, which is hereby incorporated by reference for all purposes, including dead guide sequences, complexes between CRISPR nucleases and dead guide sequences, and methods and compositions for making and using such dead guide sequences and complexes containing them.

In certain embodiments, a CRISPR nuclease meets one or both of the following criteria: it has at least 20, 30, 40, 50, 55, 60, 65, 70, 75, 80, 81, 82, 83, 84, 85, 86, 87, 88, 89, 90, 91, 92, 93, 94, 95, 96, 97, 98, 99, or 100% homology with, or it differs by no more than 1, 2, 3, 4, 5, 6, 7, 8, 9, 10, 11, 12, 13, 14, 15, 16, 17, 18, 19, 20, 25, 30, 35, 40, 35, 50, 55, 60, 65, 70, 75, 80, 85, 90, 95, 100, 150, 200, 250, 300, 350 or 400, amino acid residues from, the amino acid sequence of a reference sequences, e.g., a naturally occurring CRISPR nuclease. Additional CRISPR nucleases include, without limitation, one or more CRISPR nucleases described in WO 2016/154579.

In certain embodiments, a CRISPR nuclease contains (i.e., is covalently or non-covalently linked to) one or more additional polypeptides or nucleic acids. For example, the CRISPR nuclease can be fused at an amino or carboxy-terminus to one or more transcriptional activation domain polypeptides, one or more DNA-binding polypeptides, one or more affinity tags (e.g., in complex with one or more affinity tag ligands, such as affinity tag ligand-transcriptional activation domain fusion protein(s)), nuclear localization sequences, or a combination thereof.

Exemplary DNA-binding polypeptides include, but are not limited to, the programmable DNA binding domains described in Bolukbasi et al., Nature Methods 12, 1150-1156 (2015), the contents of which are hereby incorporated by reference in the entirety including, e.g., the programmable DNA-binding domains (pDBD), Cas9 variants, and Cas9-pDBD chimeras described therein. Exemplary transcriptional activation domain polypeptides include, but are not limited to, an activation domain of, or combinations of activation domains of, one or more of the following:

heat shock transcription factor 1 (HSF1), e.g.,
SEQ ID NO: 13
(EKCLSVACLDKNELSDHLDAMDSNLDNLQTMLSSHGFSVDTSALLDLFSPSVTV

PDMSLPDLDSSLASIQELLSPQEPPRPPEAENSSPDSGKQLVHYTAQPLFLLDPGS

VDTGSNDLPVLFELGEGSYFSEGDGFAEDPTISLLTGSEPPKAKDPTVS)

viral protein 16 (VP16), e.g.,
SEQ ID NO: 14
(DALDDFDLDML);

tetrameric VP16 (VP64), e.g.,
SEQ ID NO: 15
(DALDDFDLDMLGSDALDDFDLDMLGSDALDDFDLDMLGSDALDDFDLDML)

the p65 NF-KB transactivating subunit (p65), e.g.,
SEQ ID NO: 16
(SQYLPDTDDRHRIEEKRKRTYETFKSIMKKSPFSGPTDPRPPPRRIAVPSRSSASV

PKPAPQPYPFTSSLSTINYDEFPTMVFPSGQISQASALAPAPPQVLPQAPAPAPA

MVSALAQAPAPVPVLAPGPPQAVAPPAPKPTQAGEGTLSEALLQLQFDDEDLGA

LLGNSTDPAVFTDLASVDNSEFQQLLNQGIPVAPHTTEPMLMEYPEAITRLVTGA

QRPPDPAPAPLGAPGLPNGLLSGDEDFSSIADMDFSALL)

MyoD1, e.g.,
SEQ ID NO: 17
(MELLSPPLRDIDLTGPDGSLCSFETADDFYDDPCFDSPDLRFFEDLDPRLVHMGA

LLKPEEHAHFPTAVHPGPGAREDEHVRAPSGHHQAGRCLLWACKACKRKTTNA

DRRKAATMRERRRLSKVNEAFETLKRCTSSNPNQRLPKVEILRNAIRYIEGLQAL

LRDQDAAPPGAAAFYAPGPLPPGRGSEHYSGDSDASSPRSNCSDGMMDYSGPPS

GPRRQNGYDTAYYSEAARESRPGKSAAVSSLDCLSSIVERISTDSPAAPALLLAD

APPESPPGPPEGASLSDTEQGTQTPSPDAAPQCPAGSNPNAIYQVL)

RTA, e.g.,
SEQ ID NO: 18
(RDSREGMFLPKPEAGSAISDVFEGREVCQPKRIRPFHPPGSPWANRPLPASLAPTP

TGPVHEPVGSLTPAPVPQPLDPAPAVTPEASHLLEDPDEETSQAVKALREMADTV

IPQKEEAAICGQMDLSHPPPRGHLDELTTTLESMTEDLNLDSPLTPELNEILDTFLN

DECLLHAMHISTGLSIFDTSLF)

SET7, e.g.,
SEQ ID NO: 19
(MDSDDEMVEEAVEGHLDDDGLPHGFCTVTYSSTDRFEGNFVHGEKNGRGKFFF

FDGSTLEGYYVDDALQGQGVYTYEDGGVLQGTYVDGELNGPAQEYDTDGRLIF

KGQYKDNIRHGVCWIYYPDGGSLVGEVNEDGEMTGEKIAYVYPDERTALYGKFI

DGEMIEGKLATLMSTEEGRPHFELMPGNSVYHFDKSTSSCISTNALLPDPYESER

VYVAESLISSAGEGLFSKVAVGPNTVMSFYNGVRITHQEVDSRDWALNGNTLSL

DEETVIDVPEPYNHVSKYCASLGHKANHSFTPNCIYDMFVHPRFGPIKCIRTLRA

VEADEELTVAYGYDHSPPGKSGPEAPEWYQVELKAFQATQQK)

VPR, e.g.,
SEQ ID NO: 20
(EASGSGRADALDDFDLDMLGSDALDDFDLDMLGSDALDDFDLDMLGSDALDD

FDLDMLINSRSSGSPKKKRKVGSQYLPDTDDRHRIEEKRKRTYETFKSIMKKSPFS

GPTDPRPPPRRIAVPSRSSASVPKPAPQPYPFTSSLSTINYDEFPTMVFPSGQISQAS

ALAPAPPQVLPQAPAPAPAMVSALAQAPAPVPVLAPGPPQAVAPPAPKPTQA

GEGTLSEALLQLQFDDEDLGALLGNSTDPAVFTDLASVDNSEFQQLLNQGIPVAP

HTTEPMLMEYPEAITRLVTGAQRPPDPAPAPLGAPGLPNGLLSGDEDFSSIADMD

FSALLGSGSGSRDSREGMFLPKPEAGSAISDVFEGREVCQPKRIRPFHPPGSPWAN

RPLPASLAPTPTGPVHEPVGSLTPAPVPQPLDPAPAVTPEASHLLEDPDEETSQAV

KALREMADTVIPQKEEAAICGQMDLSHPPPRGHLDELTTTLESMTEDLNLDSPLT

PELNEILDTFLNDECLLHAMHISTGLSIFDTSLF)

histone acetyltransferase p300, e.g.,
SEQ ID NO: 21
(KFSAKRLPSTRLGTFLENRVNDFLRRQNHPESGEVTVRVVHASDKTVEVKPGM

KARFVDSGEMAESFPYRTKALFAFEEIDGVDLCFFGMHVQEYGSDCPPPNQRRV

YISYLDSVHFFRPKCLRTAVYHEILIGYLEYVKKLGYTTGHIWACPPSEGDDYIFH

CHPPDQKIPKPKRLQEWYKKMLDKAVSERIVHDYKDIFKQATEDRLTSAKELPY

FEGDFWPNVLEESIKELEQEEEERKREENTSNESTDVTKGDSKNAKKKNNKKTS

KNKSSLSRGNKKKPGMPNVSNDLSQKLYATMEKHKEVFFVIRLIAGPAANSLPPI

VDPDPLIPCDLMDGRDAFLTLARDKHLEFSSLRRAQWSTMCMLVELHTQSQ)

an hydroxylase catalytic domain of a TET family protein (e.g.,
TET1 hydroxylasecatalytic domain), e.g.,
SEQ ID NO: 22
(MSRSRHARPSRLVRKEDVNKKKKNSQLRKTTKGANKNVASVKTLSPGKLKQLI

QERDVKKKTEPKPPVPVRSLLTRAGAARMNLDRTEVLFQNPESLTCNGFTMALR

STSLSRRLSQPPLVVAKSKKVPLSKGLEKQHDCDYKILPALGVKHSENDSVPMQ

DTQVLPDIETLIGVQNPSLLKGKSQETTQFWSQRVEDSKINIPTHSGPAAEILPGPL

EGTRCGEGLFSEETLNDTSGSPKMFAQDTVCAPFPQRATPKVTSQGNPSIQLEEL

GSRVESLKLSDSYLDPIKSEHDCYPTSSLNKVIPDLNLRNCLALGGSTSPTSVIKFL

LAGSKQATLGAKPDHQEAFEATANQQEVSDTTSFLGQAFGAIPHQWELPGADPV

HGEALGETPDLPEIPGAIPVQGEVFGTILDQQETLGMSGSVVPDLPVFLPVPPNPIA

TFNAPSKWPEPQSTVSYGLAVQGAIQILPLGSGHTPQSSSNSEKNSLPPVMAISNV

ENEKQVHISFLPANTQGFPLAPERGLFHASLGIAQLSQAGPSKSDRGSSQVSVTST

VHVVNTTVVTMPVPMVSTSSSSYTTLLPTLEKKKRKRCGVCEPCQQKTNCGECT

YCKNRKNSHQICKKRKCEELKKKPSVVVPLEVIKENKRPQREKKPKVLKADFDN

KPVNGPKSESMDYSRCGHGEEQKLELNPHTVENVTKNEDSMTGIEVEKWTQNK

KSQLTDHVKGDFSANVPEAEKSKNSEVDKKRTKSPKLFVQTVRNGIKHVHCLPA

ETNVSFKKFNIEEFGKTLENNSYKFLKDTANHKNAMSSVATDMSCDHLKGRSNV

LVFQQPGFNCSSIPHSSHSIINHHASIHNEGDQPKTPENIPSKEPKDGSPVQPSLLSL

MKDRRLTLEQVVAIEALTQLSEAPSENSSPSKSEKDEESEQRTASLLNSCKAILYT

VRKDLQDPNLQGEPPKLNHCPSLEKQSSCNTVVFNGQTTTLSNSHINSATNQAST

KSHEYSKVTNSLSLFIPKSNSSKIDTNKSIAQGIITLDNCSNDLHQLPPRNNEVEYC

NQLLDSSKKLDSDDLSCQDATHTQIEEDVATQLTQLASIIKINYIKPEDKKVESTP

TSLVTCNVQQKYNQEKGTIQQKPPSSVHNNHGSSLTKQKNPTQKKTKSTPSRDR

RKKKPTVVSYQENDRQKWEKLSYMYGTICDIWIASKFQNFGQFCPHDFPTVFGK

ISSSTKIWKPLAQTRSIMQPKTVFPPLTQIKLQRYPESAEEKVKVEPLDSLSLFHLK

TESNGKAFTDKAYNSQVQLTVNANQKAHPLTQPSSPPNQCANVMAGDDQIRFQ

QVVKEQLMHQRLPTLPGISHETPLPESALTLRNVNVVCSGGITVVSTKSEEEVCSS

SFGTSEFSTVDSAQKNFNDYAMNFFTNPTKNLVSITKDSELPTCSCLDRVIQKDK

GPYYTHLGAGPSVAAVREIMENRYGQKGNAIRIEIVVYTGKEGKSSHGCPIAKW

-continued

VLRRSSDEEKVLCLVRQRTGHHCPTAVMVVLIMVWDGIPLPMADRLYTELTENL

KSYNGHPTDRRCTLNENRTCTCQGIDPETCGASFSFGCSWSMYFNGCKFGRSPSP

RRFRIDPSSPLHEKNLEDNLQSLATRLAPIYKQYAPVAYQNQVEYENVARECRLG

SKEGRPFSGVTACLDFCAHPHRDIHNMNNGSTVVCTLTREDNRSLGVIPQDEQL

HVLPLYKLSDTDEFGSKEGMEAKIKSGAIEVLAPRRKKRTCFTQPVPRSGKKRAA

MMTEVLAHKIRAVEKKPIPRIKRKNNSTTTNNSKPSSLPTLGSNTETVQPEVKSET

EPHFILKSSDNTKTYSLMPSAPHPVKEASPGFSWSPKTASATPAPLKNDATASCGF

SERSSTPHCTMPSGRLSGANAAAADGPGISQLGEVAPLPTLSAPVMEPLINSEPST

GVTEPLTPHQPNHQPSFLTSPQDLASSPMEEDEQHSEADEPPSDEPLSDDPLSPAE

EKLPHIDEYWSDSEHIFLDANIGGVAIAPAHGSVLIECARRELHATTPVEHPNRNH

PTRLSLVFYQHKNLNKPQHGFELNKIKFEAKEAKNKKMKASEQKDQAANEGPE

QSSEVNELNQIPSHKALTLTHDNVVTVSPYALTHVAGPYNHWV)

LSD1, e.g.,
SEQ ID NO: 23
(GMDVTLLEARDRVGGRVATFRKGNYVADLGAMVVTGLGGNPMAVVSKQVN

MELAKIKQKCPLYEANGQAVPKEKDEMVEQEFNRLLEATSYLSHQLDFNVLNN

KPVSLGQALEVVIQLQEKHVKDEQIEHWKKIVKTQEELKELLNKMVNLKEKIKE

LHQQYKEASEVKPPRDITAEFLVKSKHRDLTALCKEYDELAETQGKLEEKLQELE

ANPPSDVYLSSRDRQILDWHFANLEFANATPLSTLSLKHWDQDDDFEFTGSHLT

VRNGYSCVPVALAEGLDIKLNTAVRQVRYTASGCEVIAVNTRSTSQTFIYKCDA

VLCTLPLGVLKQQPPAVQFVPPLPEWKTSAVQRMGFGNLNKVVLCFDRVFWDP

SVNLFGHVGSTTASRGELFLFWNLYKAPILLALVAGEAAGIMENISDDVIVGRCL

AILKGIFGSSAVPQPKETVVSRWRADPWARGSYSYVAAGSSGNDYDLMAQPITP

GPSIPGAPQPIPRLFFAGEHTIRNYPATVHGALLSGLREAGRIADQFLGAMYTLPR

QATPGVPAQQSPSM)

CIB1, e.g.,
SEQ ID NO: 24
(MGGSGSRLSKELLAEYQDLTFLTKQEILLAHRRFCELLPQEQRSVESSLRAQVPF

EQILSLPELKANPFKERICRVFSTSPAKDSLSFEDFLDLLSVFSDTATPDIKSHYAFR

IFDFDDDGTLNREDLSRLVNCLTGEGEDTRLSASEMKQLIDNILEESDIDRDGTIN

LSEFQHVISRSPDFASSFKIVL)

AD2, e.g.,
SEQ ID NO: 25
(MNQPQRMAPVGTDKELSDLLDFSMMFPLPVTNGKGRPASLAGAQFGGSGLED

RPSSGSWGSGDQSSSSFDPSRTFSEGTHFTESHSSLSSSTFLGPGLGGKSGERGAY

ASFGRDAGVGGLTQAGFLSGELALNSPGPLSPSGMKGTSQYYPSYSGSSRRRAA

DGSLDTQPKKVRKVPPGLPSSVYPPSSGEDYGRDATAYPSAKTPSSTYPAPFYVA

DGSLHPSAELWSPPGQAGFGPMLGGGSSPLPLPPGSGPVGSSGSSSTFGGLHQHE

RMGYQLHGAEVNGGLPSASSFSSAPGATYGGVSSHTPPVSGADSLLGSRGTTAG

SSGDALGKALASIYSPDHSSNNFSSSPSTPVGSPQGLAGTSQWPRAGAPGALSPSY

DGGLHGLQSKIEDHLDEAIHVLRSHAVGTAGDMHTLLPGHGALASGFTGPMSLG

GRHAGLVGGSHPEDGLAGSTSLMHNHAALPSQPGTLPDLSRPPDSYSGLGRAGA

TAAASEIKREEKEDEENTSAADHSEEEKKELKAPRARTSPDEDEDDLLPPEQKAE

-continued

REKERRVANNARERLRVRDINEAFKELGRMCQLHLNSEKPQTKLLILHQAVSVIL

NLEQQVRERNLNPKAACLKRREEEKVSGVVGDPQMVLSAPHPGLSEAHNPAGH

M)

CR3, e.g., SEQ ID NO: 26
(MGPTSGPSLLLLLLTHLPLALGSPMYSIITPNILRLESEETMVLEAHDAQGDVPVT

VTVHDFPGKKLVLSSEKTVLTPATNHMGNVTFTIPANREFKSEKGRNKFVTVQA

TFGTQVVEKVVLVSLQSGYLFIQTDKTIYTPGSTVLYRIFTVNHKLLPVGRTVMV

NIENPEGIPVKQDSLSSQNQLGVLPLSWDIPELVNMGQWKIRAYYENSPQQVFST

EFEVKEYVLPSFEVIVEPTEKFYYIYNEKGLEVTITARFLYGKKVEGTAFVIFGIQD

GEQRISLPESLKRIPIEDGSGEVVLSRKVLLDGVQNPRAEDLVGKSLYVSATVILH

SGSDMVQAERSGIPIVTSPYQIHFTKTPKYFKPGMPFDLMVFVTNPDGSPAYRVP

VAVQGEDTVQSLTQGDGVAKLSINTHPSQKPLSITVRTKKQELSEAEQATRTMQ

ALPYSTVGNSNNYLHLSVLRTELRPGETLNVNFLLRMDRAHEAKIRYYTYLIMN

KGRLLKAGRQVREPGQDLVVLPLSITTDFIPSFRLVAYYTLIGASGQREVVADSV

WVDVKDSCVGSLVVKSGQSEDRQPVPGQQMTLKIEGDHGARVVLVAVDKGVF

VLNKKNKLTQSKIWDVVEKADIGCTPGSGKDYAGVFSDAGLTFTSSSGQQTAQR

AELQCPQPAARRRRSVQLTEKRMDKVGKYPKELRKCCEDGMRENPMRFSCQRR

TRFISLGEACKKVELDCCNYITELRRQHARASHLGLARSNLDEDIIAEENIVSRSEF

PESWLWNVEDLKEPPKNGISTKLMNIFLKDSITTWEILAVSMSDKKGICVADPFE

VTVMQDFFIDLRLPYSVVRNEQVEIRAVLYNYRQNQELKVRVELLHNPAFCSLA

TTKRRHQQTVTIPPKSSLSVPYVIVPLKTGLQEVEVKAAVYHHFISDGVRKSLKV

VPEGIRMNKTVAVRTLDPERLGREGVQKEDIPPADLSDQVPDTESETRILLQGTP

VAQMTEDAVDAERLKHLIVTPSGCGEQNMIGMTPTVIAVHYLDETEQWEKFGLE

KRQGALELIKKGYTQQLAFRQPSSAFAAFVKRAPSTWLTAYVVKVFSLAVNLIAI

DSQVLCGAVKWLILEKQKPDGVFQEDAPVIHQEMIGGLRNNNEKDMALTAFVLI

SLQEAKDICEEQVNSLPGSITKAGDFLEANYMNLQRSYTVAIAGYALAQMGRLK

GPLLNKFLTTAKDKNRWEDPGKQLYNVEATSYALLALLQLKDFDFVPPVVRWL

NEQRYYGGGYGSTQATFMVFQALAQYQKDAPDHQELNLDVSLQLPSRSSKITH

RIHWESASLLRSEETKENEGFTVTAEGKGQGTLSVVTMYHAKAKDQLTCNKFDL

KVTIKPAPETEKRPQDAKNTMILEICTRYRGDQDATMSILDISMMTGFAPDTDDL

KQLANGVDRYISKYELDKAFSDRNTLIIYLDKVSHSEDDCLAFKVHQYFNVELIQ

PGAVKVYAYYNLEESCTRFYHPEKEDGKLNKLCRDELCRCAEENCFIQKSDDKV

TLEERLDKACEPGVDYVYKTRLVKVQLSNDFDEYIMAIEQTIKSGSDEVQVGQQ

RTFISPIKCREALKLEEKKHYLMWGLSSDFWGEKPNLSYIIGKDTWVEHWPEEDE

CQDEENQKQCQDLGAFTESMVVFGCPN)

GATA4, e.g., SEQ ID NO: 27
(MYQSLAMAANHGPPPGAYEAGGPGAFMHGAGAASSPVYVPTPRVPSSVLGLS

YLQGGGAGSASGGASGGSSGGAASGAGPGTQQGSPGWSQAGADGAAYTPPPVS

PRFSFPGTTGSLAAAAAAAAAREAAAYSSGGGAAGAGLAGREQYGRAGFAGSY

SSPYPAYMADVGASWAAAAAASAGPFDSPVLHSLPGRANPAARHPNLDMFDDF

SEGRECVNCGAMSTPLWRRDGTGHYLCNACGLYHKMNGINRPLIKPQRRLSAS

-continued

RRVGLSCANCQTTTTTLWRRNAEGEPVCNACGLYMKLHGVPRPLAMRKEGIQT

RKRKPKNLNKSKTPAAPSGSESLPPASGASSNSSNATTSSSEEMRPIKTEPGLSSH

YGHSSSVSQTFSVSAMSGHGPSIHPVLSALKLSPQGYASPVSQSPQTSSKQDSWN

SLVLADSHGDIITA)

p53, e.g., SEQ ID NO: 28
(MEEPQSDPSVEPPLSQETFSDLWKLLPENNVLSPLPSQAMDDLMLSPDDIEQWF

TEDPGPDEAPRMPEAAPPVAPAPAAPTPAAPAPAPSWPLSSSVPSQKTYQGSYGF

RLGFLHSGTAKSVTCTYSPALNKMFCQLAKTCPVQLWVDSTPPPGTRVRAMAIY

KQSQHMTEVVRRCPHHERCSDSDGLAPPQHLIRVEGNLRVEYLDDRNTFRHSVV

VPYEPPEVGSDCTTIHYNYMCNSSCMGGMNRRPILTIITLEDSSGNLLGRNSFEVR

VCACPGRDRRTEEENLRKKGEPHHELPPGSTKRALPNNTSSSPQPKKKPLDGEYF

TLQIRGRERFEMFRELNEALELKDAQAGKEPGGSRAHSSHLKSKKGQSTSRHKK

LMFKTEGPDSD)

SP1, e.g., SEQ ID NO: 29
(MSDQDHSMDEMTAVVKIEKGVGGNNGGNGNGGGAFSQARSSSTGSSSSTGGG

GQESQPSPLALLAATCSRIESPNENSNNSQGPSQSGGTGELDLTATQLSQGANGW

QIISSSSGATPTSKEQSGSSTNGSNGSESSKNRTVSGGQYVVAAAPNLQNQQVLT

GLPGVMPNIQYQVIPQFQTVDGQQLQFAATGAQVQQDGSGQIQIIPGANQQIITN

RGSGGNIIAAMPNLLQQAVPLQGLANNVLSGQTQYVTNVPVALNGNITLLPVNS

VSAATLTPSSQAVTISSSGSQESGSQPVTSGTTISSASLVSSQASSSSFFTNANSYST

TTTTSNMGIMNFTTSGSSGTNSQGQTPQRVSGLQGSDALNIQQNQTSGGSLQAG

QQKEGEQNQQTQQQQILIQPQLVQGGQALQALQAAPLSGQTFTTQAISQETLQN

LQLQAVPNSGPIIIRTPTVGPNGQVSWQTLQLQNLQVQNPQAQTITLAPMQGVSL

GQTSSSNTTLTPIASAASIPAGTVTVNAAQLSSMPGLQTINLSALGTSGIQVHPIQG

LPLAIANAPGDHGAQLGLHGAGGDGIHDDTAGGEEGENSPDAQPQAGRRTRRE

ACTCPYCKDSEGRGSGDPGKKKQHICHIQGCGKVYGKTSHLRAHLRWHTGERP

FMCTWSYCGKRFTRSDELQRHKRTHTGEKKFACPECPKRFMRSDHLSKHIKTHQ

NKKGGPGVALSVGTLPLDSGAGSEGSGTATPSALITTNMVAMEAICPEGIARLAN

SGINVMQVADLQSINISGNGF)

MEF2C, e.g., SEQ ID NO: 30
(MGRKKIQITRIMDERNRQVTFTKRKFGLMKKAYELSVLCDCEIALIIFNSTNKLF

QYASTDMDKVLLKYTEYNEPHESRTNSDIVETLRKKGLNGCDSPDPDADDSVGH

SPESEDKYRKINEDIDLMISRQRLCAVPPPNFEMPVSIPVSSHNSLVYSNPVSSLGN

PNLLPLAHPSLQRNSMSPGVTHRPPSAGNTGGLMGGDLTSGAGTSAGNGYGNPR

NSPGLLVSPGNLNKNMQAKSPPPMNLGMNNRKPDLRVLIPPGSKNTMPSVSEDV

DLLLNQRINNSQSAQSLATPVVSVATPTLPGQGMGGYPSAISTTYGTEYSLSSAD

LSSLSGFNTASALHLGSVTGWQQQHLHNMPPSALSQLGACTSTHLSQSSNLSLPS

TQSLNIKSEPVSPPRDRTTTPSRYPQHTRHEAGRSPVDSLSSCSSSYDGSDREDHR

NEFHSPIGLTRPSPDERESPSVKRMRLSEGWAT)

```
TAX, e.g.,
                                                  SEQ ID NO: 31
(MAHFPGFGQSLLFGYPVYVFGDCVQGDWCPISGGLCSARLHRHALLATCPEHQI

TWDPIDGRVIGSALQFLIPRLPSFPTQRTSKTLKVLTPPITHTTPNIPPSFLQAMRKY

SPFRNGYMEPTLGQHLPTLSFPDPGLRPQNLYTLWGGSVVCMYLYQLSPPITWPL

LPHVIFCHPGQLGAFLTNVPYKRIEELLYKISLTTGALIILPEDCLPTTLFQPARAPV

TLTAWQNGLLPFHSTLTTPGLIWTFTDGTPMISGPCPKDGQPSLVLQSSSFIFHKF

QTKAYHPSFLLSHGLIQYSSFHSLHLLFEEYTNIPISLLFNEKEADDNDHEPQISPG

GLEPPSEKHFRETEV)

PPARγ, e.g.,
                                                  SEQ ID NO: 32
(MGETLGDSPIDPESDSFTDTLSANISQEMTMVDTEMPFWPTNFGISSVDLSVMED

HSHSFDIKPFTTVDFSSISTPHYEDIPFTRTDPVVADYKYDLKLQEYQSAIKVEPAS

PPYYSEKTQLYNKPHEEPSNSLMAIECRVCGDKASGFHYGVHACEGCKGFFRRTI

RLKLIYDRCDLNCRIHKKSRNKCQYCRFQKCLAVGMSHNAIRFGRMPQAEKEKL

LAEISSDIDQLNPESADLRALAKHLYDSYIKSFPLTKAKARAILTGKTTDKSPFVIY

DMNSLMMGEDKIKFKHITPLQEQSKEVAIRIFQGCQFRSVEAVQEITEYAKSIPGF

VNLDLNDQVTLLKYGVHEIIYTMLASLMNKDGVLISEGQGFMTREFLKSLRKPF

GDFMEPKFEFAVKFNALELDDSDLAIFIAVIILSGDRPGLLNVKPIEDIQDNLLQAL

ELQLKLNHPESSQLFAKLLQKMTDLRQIVTEHVQLLQVIKKTETDMSLHPLLQEI

YKDLY)
or

SET9, e.g.,
                                                  SEQ ID NO: 33
(MDSDDEMVEEAVEGHLDDDGLPHGFCTVTYSSTDRFEGNFVHGEKNGRGKFFF

FDGSTLEGYYVDDALQGQGVYTYEDGGVLQGTYVDGELNGPAQEYDTDGRLIF

KGQYKDNIRHGVCWIYYPDGGSLVGEVNEDGEMTGEKIAYVYPDERTALYGKFI

DGEMIEGKLATLMSTEEGRPHFELMPGNSVYHFDKSTSSCISTNALLPDPYESER

VYVAESLISSAGEGLFSKVAVGPNTVMSFYNGVRITHQEVDSRDWALNGNTLSL

DEETVIDVPEPYNHVSKYCASLGHKANHSFTPNCIYDMFVHPRFGPIKCIRTLRA

VEADEELTVAYGYDHSPPGKSGPEAPEWYQVELKAFQATQQK),
or
``` one or more of the transcriptional activation domains described in Chavez et al., Nat Methods. 2015 April; 12(4): 326-328, which is hereby incorporated by reference in the entirety for any and all purposes including but not limited to activation domain polypeptides and encoding polynucleotides, Cas9 (e.g., dCas9) polypeptides and encoding polynucleotides, and fusion proteins, and complexes (e.g., with sgRNA) thereof.

In some cases, the CRISPR nuclease is fused to one or more affinity tags. For example, the CRISPR nuclease may be a component of a SunTag. Exemplary SunTags or SunTag components include, without limitation, one or more of the affinity tagged CRISPR nucleases or affinity tag ligands, and fusion proteins thereof, described in WO 2016/011070. In one embodiment, the CRISPR nuclease contains one or more affinity tags that are non-covalently bound to one or more ligand-transcriptional activation domain fusion proteins. In such embodiments, the transcriptional activation domain fused to the affinity tag ligand can be, e.g., one or more of the transcriptional activation domains described herein, such as those of SEQ ID NOs: 13-33, a transcriptional activation domain described in WO 2016/011070, or a combination or derivative thereof.

As used herein, the terms "Cas9," "Cas9 molecule," and the like, refers to a Cas9 polypeptide or a nucleic acid encoding a Cas9 polypeptide. A "Cas9 polypeptide" is a polypeptide that can form a complex with a guide RNA (gRNA) and bind to a nucleic acid target containing a target domain and, in certain embodiments, a PAM sequence. Cas9 molecules include those having a naturally occurring Cas9 polypeptide sequence and engineered, altered, or modified Cas9 polypeptides that differ, e.g., by at least one amino acid residue, from a reference sequence, e.g., the most similar naturally occurring Cas9 molecule. A Cas9 molecule may be a Cas9 polypeptide or a nucleic acid encoding a Cas9 polypeptide. A Cas9 molecule may be a nuclease (an enzyme that cleaves both strands of a double-stranded nucleic acid), a nickase (an enzyme that cleaves one strand of a double-stranded nucleic acid), or a catalytically inactive (or dead) Cas9 molecule. A Cas9 molecule having nuclease or nickase activity is referred to as a "catalytically active Cas9 molecule" (a "caCas9" molecule). A Cas9 molecule lacking the ability to cleave or nick target nucleic acid is referred to as a "catalytically inactive Cas9 molecule" (a "ciCas9" molecule) or a "dead Cas9" ("dCas9").

In certain embodiments, a Cas9 molecule meets one or both of the following criteria: it has at least 20, 30, 40, 50, 55, 60, 65, 70, 75, 80, 81, 82, 83, 84, 85, 86, 87, 88, 89, 90, 91, 92, 93, 94, 95, 96, 97, 98, 99, or 100% homology with, or it differs by no more than 1, 2, 3, 4, 5, 6, 7, 8, 9, 10, 11, 12, 13, 14, 15, 16, 17, 18, 19, 20, 25, 30, 35, 40, 35, 50, 55, 60, 65, 70, 75, 80, 85, 90, 95, 100, 150, 200, 250, 300, 350 or 400, amino acid residues from, the amino acid sequence of a reference sequence, e.g., a naturally occurring Cas9 molecule.

In some embodiments, the Cas9 molecule is a *S. pyogenes* Cas9 (SpCas9) or variant thereof. In some embodiments, the Cas9 molecule is a *S. aureus* Cas9 (SaCas9) or variant thereof (see, e.g., FIGS. 7A-11B herein). In some embodiments, the Cas9 molecule is a *Campylobacter jejuni* Cas9 (CjCas9) or variant thereof (see, Kim et al., *Nat. Comm.*, 8, 14500 (2017). In some embodiments, the Cas9 molecule is a *Neisseria meningitides* Cas9 (NmCas9) or variant thereof (see, U.S. Pat. No. 9,074,199). In some embodiments, the Cas9 molecule is a *Streptococcus thermophilus* Cas9 (StCas9) or variant thereof (see, e.g., Xu et al., *Cell Mol Life Sci.*, 72:383-99 (2014)). In some embodiments, the Cas9 molecule is a dCas9 molecule.

In certain embodiments, the Cas9 molecule is a *S. pyogenes* Cas9 variant. In certain embodiments, the Cas9 variant is the EQR variant. In certain embodiments, the Cas9 variant is the VRER variant. In certain embodiments, the dCas9 molecule is a *S. pyogenes* Cas9 variant. In certain embodiments, the Cas9 variant is the EQR variant. In certain embodiments, the Cas9 variant is the VRER variant. In certain embodiments, a Cas9 system comprises a Cas9 molecule, e.g., a Cas9 molecule described herein, e.g., the Cas9 EQR variant or the Cas9 VRER variant.

In certain embodiments, the Cas9 molecule is a *S. aureus* Cas9 variant. In certain embodiments, the Cas9 variant is the KKH (E782K/N968K/R1015H) variant (see, e.g., Kleinstiver et al., Nature 523, 481-485 (23 Jul. 2015); and Leenay et al. Molecular Cell, Vol. 62, Issue 1, 2016, p. 137), the entire contents of which are expressly incorporated herein by reference and especially with regard to Cas (e.g., Cas9) variants such as those having altered PAM specificities). In certain embodiments, the Cas9 variant is the E782K/K929R/R1015H variant (see, e.g., Kleinstiver 2015). In certain embodiments, the Cas9 variant is the E782K/K929R/N968K/R1015H variant (see, e.g., Kleinstiver 2015). In certain embodiments the Cas9 variant comprises one or more mutations in one of the following residues: E782, K929, N968, R1015. In certain embodiments the Cas9 variant comprises one or more of the following mutations: E782K, K929R, N968K, R1015H and R1015Q (see, e.g., Kleinstiver 2015). In certain embodiments, a Cas9 system comprises a Cas9 molecule, e.g., a Cas9 molecule described herein, e.g., the Cas9 KKH variant.

As used herein, the terms "Cpf1," "Cpf1 molecule," and the like, refers to a Cpf1 polypeptide or a nucleic acid encoding a Cpf1 polypeptide. A "Cpf1 polypeptide" is a polypeptide that can form a complex with a guide RNA (gRNA) and bind to a nucleic acid target containing a target domain and, in certain embodiments, a PAM sequence. Cpf1 molecules include those having a naturally occurring Cpf1 polypeptide sequence and engineered, altered, or modified Cpf1 polypeptides that differ, e.g., by at least one amino acid residue, from a reference sequence, e.g., the most similar naturally occurring Cpf1 molecule. A Cpf1 molecule may be a Cpf1 polypeptide or a nucleic acid encoding a Cpf1 polypeptide. Exemplary Cpf1 polypeptides include those isolated from *Prevotella, Francisella novicida* (FnCpf1), *Lachnospiraceae bacterium* (LbCpf1) and *Acidaminococcus* sp. (AsCpf1) (see, e.g., Tóth et al., *Biology Direct*, 11:46 (2016).

In certain embodiments, a Cpf1 molecule meets one or both of the following criteria: it has at least 20, 30, 40, 50, 55, 60, 65, 70, 75, 80, 81, 82, 83, 84, 85, 86, 87, 88, 89, 90, 91, 92, 93, 94, 95, 96, 97, 98, 99, or 100% homology with, or it differs by no more than 1, 2, 3, 4, 5, 6, 7, 8, 9, 10, 11, 12, 13, 14, 15, 16, 17, 18, 19, 20, 25, 30, 35, 40, 35, 50, 55, 60, 65, 70, 75, 80, 85, 90, 95, 100, 150, 200, 250, 300, 350 or 400, amino acid residues from, the amino acid sequence of a reference sequence, e.g., a naturally occurring Cpf1 molecule.

As used herein, the term "gRNA molecule" or "gRNA" refers to a guide RNA which is capable of targeting a CRISPR nuclease to a target nucleic acid. In one embodiment, the term "gRNA molecule" refers to a guide ribonucleic acid. In another embodiment, the term "gRNA molecule" refers to a nucleic acid encoding a gRNA. In one embodiment, a gRNA molecule is non-naturally occurring. In one embodiment, a gRNA molecule is a synthetic gRNA molecule.

The guide RNA can be a scaffold RNA that binds to one or more protein or nucleic acid ligands (scaffold RNA ligands). The ligands can be fused or otherwise covalently or non-covalently linked to transcriptional activation domains. In an alternative embodiment, the scaffold RNA is not a guide RNA in that it does not specifically associate with a CRISPR nuclease. Exemplary scaffold RNAs, and CRISPR nuclease/scaffold RNA complexes, and methods of making and using such, are described in, e.g., WO 2016/054106 (describing CRISPR-associating and CRISPR independent scaffold RNAs) and Zhang et al., Scientific Reports 5, Article No. 16277 (2015); Konermann et al., 2015, Nature 517:583-8 (describing CRISPR/gRNA-directed synergistic activation mediators (SAM)).

"Subject," as used herein, may mean either a human or non-human animal. The term includes, but is not limited to, mammals (e.g., humans, other primates, pigs, rodents (e.g., mice and rats or hamsters), rabbits, guinea pigs, cows, horses, cats, dogs, sheep, and goats). In an embodiment, the subject is a human. In another embodiment, the subject is poultry. In another embodiment, the subject is piscine. In certain embodiments, the subject is a human, and in certain of these embodiments the human is an infant, child, young adult, or adult.

As used herein, the terms "target nucleic acid" or "target gene" refer to a nucleic acid which is being targeted for binding, e.g., by a CRISPR nuclease in complex with a guide RNA, a guide-RNA, or a scaffold RNA. In certain embodiments, a target nucleic acid comprises one gene, or a promoter or enhancer region operably linked to one gene. In certain embodiments, a target nucleic acid may comprise one or more genes, e.g., two genes, three genes, four genes, or five genes, or promoters or enhancer regions operably linked to one or more genes. In one embodiment, a target nucleic acid may comprise a promoter region, or control region, of a gene. In one embodiment, a target nucleic acid may comprise an intron of a gene. In another embodiment, a target nucleic acid may comprise an exon of a gene. In one embodiment, a target nucleic acid may comprise a coding region of gene. In one embodiment, a target nucleic acid may comprise a non-coding region of a gene. In some embodiments, the target nucleic acid is a control region, promoter, enhancer, intron, exon, transcription start site, coding region, or non-coding region of a gene listed in Table 1 herein.

In some embodiments, the target nucleic acid is a control region, promoter, enhancer, intron, exon, transcription start site, coding region, or non-coding region of a gene in the same pathway as a gene listed in Table 1 herein. The target nucleic acid can, e.g., be a control region, promoter, enhancer, intron, exon, transcription start site, coding region, or non-coding region of a gene upstream and in the same pathway as a gene listed in Table 1 herein. Additionally, where two or more genes or positions are targeted, or alternatively, the target nucleic acid can, e.g., be a control region, promoter, enhancer, intron, exon, transcription start site, coding region, or non-coding region of a gene downstream and in the same pathway as a gene listed in Table 1 herein. Additionally, where two or more genes or positions are targeted, or alternatively, the target nucleic acid can, e.g., be a control region, promoter, enhancer, intron, exon, transcription start site, coding region, or non-coding region of a gene in a parallel pathway as a gene listed in Table 1 herein. Exemplary genes in the same pathway or a parallel pathway as one or more of the genes listed in Table 1 are described e.g., in the KEGG pathway database (available at www.genome.jp/kegg/pathway.html).

"Target position" as used herein, refers to a site on a target nucleic acid that is hybridized to a guide RNA (e.g., in complex with a CRISPR nuclease) or scaffold RNA. Optimized target positions include, without limitation, one or more target positions optimized for transcriptional activation that are described in WO 2016/011080.

"Episomal vector" or "episomally propagating vector" refers to a plasmid or viral vector that persists or propagates in a mammalian cell as an episomal element. Episomal vectors described herein can encode one or more components (e.g., CRISPR nuclease, guide RNA, zinc finger nuclease, TALEN, TAL effector, scaffold RNA, transcriptional activator, affinity element, or combination thereof) for treatment of a disease or condition by transcriptional activation (e.g., a disease or condition of Table 1). Episomal vectors include, but are not limited to, Adeno-associated virus (AAV) vectors, and Epstein-barr virus (EBV) vectors. Suitable AAV vectors and methods for making and using such AAV vectors, e.g., for delivering the vectors into target cells are described in Samulski R et al. (1987), J. Virol. 61: 3096-3101; Walsh et al., Proc. Soc. Exp. Biol. Med. 204: 289-300 (1993); Fisher K J et al. (1996), J. Virol, 70: 520-532; Samulski R et al. (1989), J. Virol. 63: 3822-3826; U.S. Pat. Nos. 5,252,479; 5,139,941; 5,436,146; International Patent Application No. WO 94/13788; and International Patent Application No. WO 93/24641, the entire disclosures of which are herein incorporated by reference.

As used herein, the term "Zinc Finger Nuclease" refers to a zinc finger DNA binding protein (or zinc finger DNA binding domain within a larger protein) that binds DNA in a sequence-specific manner through one or more zinc fingers, which are regions of amino acid sequence within the zinc finger binding domain whose structure is stabilized through coordination of a zinc ion. The term zinc finger DNA binding protein is often abbreviated as zinc finger nuclease or ZFN.

As used herein, the term "transcription activator-like effector nuclease" refers to a protein, that includes a transcription activator-like effector DNA-binding domain fused to a DNA cleavage domain, that binds DNA in a sequence-specific manner. The term transcription activator-like effector nuclease is often abbreviated to TALEN.

DETAILED DESCRIPTION OF THE INVENTION

Introduction

Described herein are methods and compositions for treating a disease in a mammalian subject associated with, exacerbated by, or caused by reduced transcription of a gene, reduced amount of a gene product, or reduced activity of a gene product by increasing transcription of a target gene. Such methods and compositions can be useful, e.g., for treating a haploinsufficiency disease in the subject. Haploinsufficiency diseases that can be treated by the methods and compositions described herein include, without limitation, one or more of the diseases listed in Table 1. Table 1 provides the Entrez Gene ID (column 2) from the national center for bioinformatics (NCBI) and corresponding gene symbol (column 1) provided by the human genome nomenclature committee (HGNC), a pubmed ID (PMID) citation to a supporting reference (column 4), and a brief description of the associated disorder (column 5). The table is adapted from Supplementary Table 1 of Dang et al., *European Journal of Human Genetics* (2008) 16, 1350-57 and the ClinVar (https://www.ncbi.nlm.nih.gov/clinvar) and ClinGen (https://www.clinicalgenome.org) databases.

Nucleases

In some embodiments of the methods described herein, a host cell is contacted with one or more nucleases. In some embodiments, the nuclease is a endonuclease, site-specific recombinase, transposase, topoisomerase, zinc finger nuclease, TALEN, and includes modified derivatives and variants thereof.

In some embodiments, a nuclease is capable of targeting a designated nucleotide or region within the target site. In some embodiments, the nuclease is capable of targeting a region positioned between the 5' and 3' regions of the target site. In another embodiment, the nuclease is capable of targeting a region positioned upstream or downstream of the 5' and 3' regions of the target site (e.g., upstream or downstream of the transcription start site (TSS)). A recognition sequence is a polynucleotide sequence that is specifically recognized and/or bound by the nuclease. The length of the recognition site sequence can vary, and includes, for example, nucleotide sequences that are at least 10, 12, 14, 16, 18, 19, 20, 21, 22, 23, 24, 25, 26, 27, 28, 29, 30, 35, 40, 45, 50, 55, 60, 65, 70 or more nucleotides in length. In some embodiments, the recognition sequence is palindromic, i.e., the sequence on one DNA strand reads the same in the opposite direction on the complementary DNA strand. In some embodiments, the target site of the nuclease is within the recognition sequence.

Zinc Finger Nuclease

In some embodiments, the nuclease is a zinc-finger nuclease (ZFN). ZFNs typically comprise a zinc finger DNA binding domain and a nuclease domain. Generally, ZFNs include two zinc finger arrays (ZFAs), each of which is fused to a single subunit of a non-specific endonuclease, such as the nuclease domain from the FokI enzyme, which becomes active upon dimerization. Typically, a single ZFA consists of 3 or 4 zinc finger domains, each of which is designed to recognize a specific nucleotide triplet (GGC, GAT, etc.). A ZFN composed of two "3-finger" ZFAs is therefore capable of recognizing an 18 base pair target site (i.e., recognition sequence); an 18 base pair recognition sequence is generally unique, even within large genomes such as those of humans and plants. By directing the co-localization and dimerization of the two FokI nuclease monomers, ZFNs generate a functional site-specific endonuclease that can target a particular locus (e.g., gene, promotor or enhancer).

Zinc-finger nucleases useful in the methods disclosed herein include those that are known and ZFN that are engineered to have specificity for one or more target sites described herein (e.g., promotor or enhancer nucleotide sequence). Zinc finger domains are amenable for designing polypeptides which specifically bind a selected polynucleotide recognition sequence within a target site of the host cell genome. ZFN can comprise an engineered DNA-binding zinc finger domain linked to a non-specific endonuclease domain, for example, a nuclease domain from a Type IIs endonuclease such as HO or FokI. In some examples, a zinc finger DNA binding domain can be fused to a site-specific recombinase, transposase, or a derivative thereof that retains DNA nicking and/or cleaving activity.

In a preferred embodiment, additional functionalities can be fused to the zinc-finger binding domain, including but not limited to, transcriptional activator domains (such as VP16, VP48, VP64, VP160 and the like) or transcription repressor domains (such as KRAB). In one embodiment, the zinc finger nuclease is engineered such that the zinc finger nuclease comprises a transcriptional activator domain selected from VP16, VP48, VP64 or VP160. In one embodiment, the zinc finger nuclease is engineered such that the zinc finger nuclease comprises a transcriptional activator domain selected from HSF1, VP16, VP64, p65, RTA, MyoD1, SET7, VPR, histone acetyltransferase p300, TET1 hydroxylase catalytic domain, LSD1, CIB1, AD2, CR3, GATA4, p53, SP1, MEF2C, TAX, PPAR-gamma, and SET9. For example, engineered zinc finger transcriptional activator that interact with a promoter region of the gamma-globulin gene was shown to enhance fetal hemoglobin production in primer adult erythroblasts (Wilber et al., *Blood,* 115(15): 3033-3041). Other polydactyl zinc-finger transcription factors are also known in the art, including those disclosed in Beerli and Barbas (see, Nature Technology, (2002) 20:135-141).

Each zinc finger domain recognizes three consecutive base pairs in the target DNA. For example, a three finger domain recognizes a sequence of nine contiguous nucleotides, with a dimerization requirement of the nuclease, two sets of zinc finger triplets are used to bind a 18 nucleotide recognition sequence. Useful zinc finger modules include those that recognize various GNN and ANN triplets (Dreier et al., (2001) *J Biol Chem* 276:29466-78; Dreier et al., (2000) *J Mol Biol* 303:489-502; Liu et al., (2002) *J Biol Chem* 277:3850-6), as well as those that recognize various CNN or TNN triplets (Dreier et al., (2005) *J Biol Chem* 280:35588-97; Jamieson et al., (2003) *Nature Rev Drug Discovery* 2:361-8). See also, Durai et al., (2005) *Nucleic Acids Res* 33:5978-90; Segal, (2002) *Methods* 26:76-83; Porteus and Carroll, (2005) *Nat Biotechnology* 23:967-73; Pabo et al., (2001) *Ann Rev Biochem* 70:313-40; Wolfe et al., (2000) *Ann Rev Biophys Biomol Struct* 29:183-212; Segal and Barbas (2001) *Curr Opin Biotechnol* 12:632-7; Segal et al., (2003) *Biochemistry* 42:2137-48; Beerli and Barbas, (2002) *Nat Biotechnol* 20:135-41; Carroll et al., (2006) *Nature Protocols* 1:1329; Ordiz et al., (2002) *Proc Natl Acad Sci USA* 99:13290-5; Guan et al., (2002) *Proc Natl Acad Sci USA* 99:13296-301; WO2002099084; WO00/42219; WO02/42459; WO2003062455; US20030059767; US Patent Application Publication Number 2003/0108880; U.S. Pat. Nos. 6,140,466, 6,511,808 and 6,453,242. Useful zinc-finger nucleases also include those described in WO03/080809; WO05/014791; WO05/084190; WO08/021207; WO09/042186; WO09/054985; and WO10/065123.

In some embodiments, a ZFN comprises a fusion protein having a cleavage domain of a Type IIS restriction endonuclease fused to an engineered zinc finger binding domain, wherein the binding domain further comprises one or more transcriptional activators. In some embodiments, the type IIS restriction endonuclease is selected from a HO endonuclease or a FokI endonuclease. In some embodiments, the zinc finger binding domain comprises 3, 4, 5 or 6 zinc fingers. In another embodiment, the zinc finger binding domain specifically binds to a recognition sequence corresponding to a promoter or enhancer disclosed herein (e.g., SIM1, MC4R, PKD1, SETD5, THUMPD3, SCN2A and PAX6 promotor or enhancer). In one embodiment, the one or more transcriptional activators is selected from VP16, VP48, VP64, or VP160. Generally, the DNA-binding domain of a ZFN contains between 3 and 6 individual zinc finger repeats and can recognize between 9 and 18 contiguous nucleotides. Each ZFN can be designed to target a specific target site in the host cell genome, e.g., a promotor sequence, an enhancer sequence, or exon/intron within a gene.

TALENs

In some embodiments of the methods, the nuclease is a TALEN. TAL effectors (TALEs) are proteins secreted by *Xanthomonas* bacteria and play an important role in disease or triggering defense mechanisms, by binding host DNA and activating effector-specific host genes. see, e.g., Gu et al. (2005) *Nature* 435:1122-5; Yang et al., (2006) *Proc. Natl. Acad. Sci. USA* 103:10503-8; Kay et al., (2007) *Science* 318:648-51; Sugio et al., (2007) *Proc. Natl. Acad. Sci. USA* 104:10720-5; Romer et al., (2007) *Science* 318:645-8; Boch et al., (2009) *Science* 326(5959):1509-12; and Moscou and Bogdanove, (2009) 326(5959):1501. A TALEN comprises a TAL effector DNA-binding domain fused to a DNA cleavage domain. The DNA binding domain interacts with DNA in a sequence-specific manner through one or more tandem repeat domains. The repeated sequence typically comprises 33-34 highly conserved amino acids with divergent $12^{th}$ and $13^{th}$ amino acids. These two positions, referred to as the Repeat Variable Diresidue (RVD) are highly variable and show a strong correlation with specific nucleotide recognition (Boch et al., (2009) *Science* 326(5959):1509-12; and Moscou and Bogdanove, (2009) 326(5959):1501). This relationship between amino acid sequence and DNA recognition sequence has allowed for the engineering of specific DNA-binding domains by selecting a combination of repeat segments containing the appropriate RVDs.

The TAL-effector DNA binding domain can be engineered to bind to a target DNA sequence and fused to a nuclease domain, e.g., a Type IIS restriction endonuclease, such as FokI (see e.g., Kim et al. (1996) *Proc. Natl. Acad. Sci. USA* 93:1156-1160). In some embodiments, the nuclease domain can comprises one or more mutations (e.g., FokI variants) that improve cleavage specificity (see, Doyon et al., (2011) *Nature Methods,* 8 (1): 74-9) and cleavage activity (Guo et al., (2010) *Journal of Molecular Biology,* 400 (1): 96-107). Other useful endonucleases that can be used as the nuclease domain include, but are not limited to, HhaI, HindIII, Nod, BbvCI, EcoRI, BglI, and AlwI. In some embodiments, the TALEN can comprise a TAL effector DNA binding domain comprising a plurality of TAL effector repeat sequences that bind to a specific nucleotide sequence (i.e., recognition sequence) in the target DNA. While not to be construed as limiting, TALENs useful for the methods provided herein include those described in WO10/079430 and U.S. Patent Application Publication No. 2011/0145940.

In some embodiments, the TAL effector DNA binding domain can comprise 10 or more DNA binding repeats, and preferably 15 or more DNA binding repeats. In some embodiments, each DNA binding repeat comprises a RVD that determines recognition of a base pair in the target DNA, and wherein each DNA binding repeat is responsible for recognizing one base pair in the target DNA. In some embodiments, the RVD comprises one or more of: HD for recognizing C; NG for recognizing T; NI for recognizing A; NN for recognizing G or A; NS for recognizing A or C or G or T; N* for recognizing C or T, where * represents a gap in the second position of the RVD; HG for recognizing T; H* for recognizing T, where * represents a gap in the second position of the RVD; IG for recognizing T; NK for recognizing G; HA for recognizing C; ND for recognizing C; HI for recognizing C; HN for recognizing G; NA for recognizing G; SN for recognizing G or A; and YG for recognizing T.

In a preferred embodiment, the TALEN is engineered such that the TAL effector comprises one or more transcriptional activator domains (e.g., VP16, VP48, VP64 or VP160). For example, engineered TAL effectors having a transcriptional activator domain at the c-terminus of the TAL effector were shown to modulate transcription of Sox2 and Klf4 genes in human 293FT cells (Zhang et al., Nature Biotechnology, 29(2):149-153 (2011). Other TAL effector transcription factors (TALE-TFs) are also known in the art, including those disclosed in Perez-Pinera et al., (Nature Methods, (2013) 10(3):239-242) that demonstrated modulation of IL1RN, KLK3, CEACAM5 and ERBB2 genes in human 293T cells using TALE-TFs. In some embodiments, the one or more transcriptional activator domains are located adjacent to the nuclear localization signal (NLS) present in the C-terminus of the TAL effector. In another embodiment, the TALE-TFs can bind nearby sites upstream or downstream of the transcriptional start site (TSS) for a target gene. In one embodiment, the TAL effector comprises a transcriptional activator domain selected from VP16, VP48, VP64 or VP160. In another embodiment, the TAL effector comprises a transcriptional activator domain selected from HSF1, VP16, VP64, p65, RTA, MyoD1, SET7, VPR, histone acetyltransferase p300, TET1 hydroxylase catalytic domain, LSD1, CIB1, AD2, CR3, GATA4, p53, SP1, MEF2C, TAX, PPAR-gamma, and SET9.

In some embodiments, the TALEN comprises a TAL effector DNA-binding domain fused to a DNA cleavage domain, wherein the TAL effector comprises a transcriptional activator. In some embodiments, the DNA cleavage domain is of a Type IIS restriction endonuclease selected from a HO endonuclease or a FokI endonuclease. In some embodiments, the TAL effector DNA-binding domain specifically binds to a recognition sequence corresponding to a promoter region or enhancer region disclosed herein (e.g., SIM1, MC4R, PKD1, SETD5, THUMPD3, SCN2A and PAX6 promotor or enhancer). Generally, the DNA-binding domain of a TALEN is designed to target a specific target site in the host cell, e.g., a promotor sequence or an enhancer sequence.

In some embodiments, the target site for the zinc finger nuclease or TALEN is endogenous to the host cell, such as a native locus in the host cell genome. In some embodiments, the target site is selected according to the type of nuclease to be utilized in the method. If the nuclease to be utilized is a zinc finger nuclease, optimal target sites may be selected using a number of publicly available online resources. See, e.g., Reyon et al., BMC Genomics 12:83 (2011), which is hereby incorporated by reference in its entirety. Publicly available methods for engineering zinc finger nucleases include: (1) Context-dependent Assembly (CoDA), (2) Oligomerized Pool Engineering (OPEN), (3) Modular Assembly, (4) ZiFiT (internet-accessible software for the design of engineered zinc finger arrays), (5) ZiFDB (internet-accessible database of zinc fingers and engineered zinc finger arrays), and (6) ZFNGenome. For example, OPEN is a publicly available protocol for engineering zinc finger arrays with high specificity and in vivo functionality, and has been successfully used to generate ZFNs that function efficiently in plants, zebrafish, and human somatic and pluripotent stem cells. OPEN is a selection-based method in which a pre-constructed randomized pool of candidate ZFAs is screened to identify those with high affinity and specificity for a desired target sequence. Additionally, ZFNGenome is a GBrowse-based tool for identifying and visualizing potential target sites for OPEN-generated ZFNs. ZFNGenome provides a compendium of potential ZFN target sites in sequenced and annotated genomes of model organisms. ZFNGenome includes more than 11 million potential ZFN target sites, mapped within the fully sequenced genomes of seven model organisms; S. cerevisiae, C. reinhardtii, A. thaliana, D. melanogaster, D. rerio, C. elegans, and H. sapiens. ZFNGenome provides information about each potential ZFN target site, including its chromosomal location and position relative to transcription initiation site(s). Users can query ZFNGenome using several different criteria (e.g., gene ID, transcript ID, target site sequence).

In some embodiments, if the nuclease is a TALEN, optimal target sites may be selected in accordance with the methods described by Sanjana et al., Nature Protocols, 7:171-192 (2012), which is hereby incorporated by reference in its entirety. TALENs function as dimers, and a pair of TALENs, referred to as the left and right TALENs, target sequences on opposite strands of DNA. TALENs are engineered as a fusion of the TALE DNA-binding domain and a monomeric FokI catalytic domain. To facilitate FokI dimerization, the left and right TALEN target sites are generally selected with a spacing of approximately 14-20 bases.

In some embodiments, the one or more nucleases useful for the methods described herein are provided, e.g., delivered into the host cell as a purified protein. In some embodiments, the one or more nucleases are provided via polynucleotide(s) comprising a nucleic acid encoding the nuclease. In another embodiment, the one or more nucleases can be introduced into the host cell as purified RNA which can be directly translated in the host cell nucleus. In a preferred embodiment, the polynucleotide comprising a nucleic acid encoding the nuclease comprises an expression vector that allows for the expression of the nuclease within a host cell. Suitable expression vectors include episomal vectors.

In some embodiments, where the nuclease functions as a dimer requiring the separate expression of each monomer, e.g., zinc finger nucleases and TALENs, each monomer of the dimer may be expressed from the same episomal vector or from different episomal vectors. In another embodiment, where multiple nucleases are introduced to the cell to introduce double-strand breaks at different target sites, the nucleases can be encoded on a single episomal vector or on separate episomal vectors.

In one aspect, the present invention provides a method of treating a haploinsufficiency disease in a mammalian subject, the method comprising contacting a cell of the subject with a composition comprising a zinc finger nuclease or TALEN that, under conditions present in a nucleus of the cell, the zinc finger nuclease or TALEN specifically hybridizes to a promoter region or an enhancer region; wherein the contacting forms a complex comprising the DNA binding domain of the zinc finger nuclease or TALEN, and the promoter region or enhancer region, wherein the complex activates transcription of the wild-type copy of the haploinsufficient gene in an amount and for a duration sufficient to treat the haploinsufficiency disease in the subject. In some embodiments, the promoter or enhancer region corresponds to a promoter or enhancer region (i.e., control region) of any of the genes listed in Table 1.

In some embodiments, the contacting comprises contacting the cell with an episomal vector encoding the zinc finger nuclease or TALEN. In some embodiments, the episomal vector(s) are non-integrating. In some embodiments, the zinc finger nuclease or TALEN has been modified to comprises one or more transcriptional activation domains. In one embodiment, the one or more transcriptional activation domains is selected from the group consisting of HSF1, VP16, VP64, p65, MyoD1, RTA, SET7/9, VPR, histone acetyltransferase p300, an hydroxylase catalytic domain of a TET family protein (e.g., TET1 hydroxylase catalytic domain), LSD1, CIB1, AD2, CR3, EKLF1, GATA4, PRVIE, p53, SP1, MEF2C, TAX, and PPARγ. In some embodiments, the transcriptional activation domain is VP64. In some embodiments, the haploinsufficient gene is SIM1, Leptin, Leptin receptor, MC4R, SCN2A, SETD5, PAX6, PKD1, MC3R, POMC, STAT3, STAT5, SOCS3, GHR, NPY, NPY1R, NPY2R, NPY5R, PYY, AMPK (PRKAA1, PRKAA2, PRKAB1, PRKAB2, PRKAG1, PRKAG2, PRKAG3), OXT, JAK2, SHP2, NOS3, NROB2, BRS3, CARTPT, FABP4, HTR2C, IL6, NHLH2, NMU, NPB, NPBWRI, PNPLA2, UCP3, ADIPOQ, APOA5, ARNT2, ASIP, C1QTNF2, C3AR1, CCK, CPT1B, CSF2, DGAT1, DGAT2, GHRL, GHSR, HSD11B1, HTR7, INSIG1, INSIG2, LIPC, NMUR1, NMUR2, NPBWR2, NTS, PPARGC1A, PPY, RETN, SIRT1, TGFBR2, WDTC1, or FOXO1.

TABLE 1

Genes Associated With Haploinsufficiency Diseases

| Gene Symbol | Entrez Gene ID | Chromosome | PubMed (PMID) | Disorder/Syndrome |
| --- | --- | --- | --- | --- |
| TP73 | 7161 | 1 | 11454718 | prostate hyperplasia and prostate cancer |
| DFFB | 1677 | 1 | 16156899 | oligodendroglioma development |
| KCNAB2 | 8514 | 1 | 11580756 | characteristic craniofacial abnormalities, mental retardation, and epilepsy with 1p36 deletion syndrome |
| CHD5 | 26038 | 1 | — | monosomy 1p36 syndrome |
| CAMTA1 | 23261 | 1 | 15709179 | tumors development |
| PINK1 | 65018 | 1 | 15349860 | sporadic early-onset parkinsonism |
| SAM68 | 10657 | 1 | 17927519 | mammary tumor onset and tumor multiplicity |
| KCNQ4 | 9132 | 1 | — | DEAFNESS, AUTOSOMAL DOMINANT NONSYNDROMIC SENSORINEURAL 2 |
| GLUT1 | 6513 | 1 | 12029447, 11477212, 11136715, 16497725 | Facilitated glucose transporter protein type 1 (GLUT1) deficiency syndrome |
| MYH | 4595 | 1 | 16292541 | hepatocellular carcinoma and cholangiocarcinom |
| FOXE3 | 2301 | 1 | 11980846 | anterior segment dysgenesis similar to Peters' anomaly |
| HUD | 1996 | 1 | 16278682 | poor prognosis |
| INK4C | 1031 | 1 | 16260494 | medulloblastoma formation |
| NFIA | 4774 | 1 | 17530927 | Complex central nervous system (CNS) malformations and urinary tract defects |
| CCN1 | 3491 | 1 | 17023674 | delayed formation of the ventricular septum in the embryo and persistent ostium primum atrial septal defects |
| ABCA4 | 24 | 1 | — | Stargardt disease, retinitis pigmentosa-19, and macular degeneration age-related 2 |
| WNT2B | 7482 | 1 | 17351355 | mental retardation, short stature and colobomata |
| ADAR | 103 | 1 | 16536805 | dyschromatosis symmetrica hereditaria |
| ATP1A2 | 477 | 1 | — | familial hemiplegic migraine type 2 |
| MPZ | 4359 | 1 | — | neurologic diseases, including CHN, DSS, and CMT1B |

TABLE 1-continued

Genes Associated With Haploinsufficiency Diseases

| Gene Symbol | Entrez Gene ID | Chromosome | PubMed (PMID) | Disorder/Syndrome |
| --- | --- | --- | --- | --- |
| MYOC | 4653 | 1 | — | hereditary juvenile-onset open-angle glaucoma |
| HRPT2 | 79577 | 1 | 16458039 | Ossifying fibroma (progressive enlargement of the affected jaw) |
| LRH-1 | 2494 | 1 | 17670946, 15684064 | inflammatory bowel disease |
| IRF6 | 3664 | 1 | — | van der Woude syndrome and popliteal pterygium syndrome |
| PROX1 | 5629 | 1 | — | Lymphatic vascular defects, adult-onset obesity |
| TP53BP2 | 7159 | 1 | — | no suppression of tumor growth |
| NLRP3 | 114548 | 1 | — | CINCA syndrome |
| ID2 | 3398 | 2 | 15569159 | Congenital hydronephrosis |
| MYCN | 4613 | 2 | 15821734 | reduced brain size and intestinal atresias in Feingold syndrome |
| GCKR | 2646 | 2 | 9570959 | one form of maturity onset diabetes of the young |
| SPAST | 6683 | 2 | — | SPASTIC PARAPLEGIA 4 |
| MSH6 | 2956 | 2 | 10751599 | limitation of mismatch repair |
| FSHR | 2492 | 2 | 14502087 | degenerative changes in the central nervous system |
| SPR | 6697 | 2 | 15241655 | dopa-responsive dystonia |
| PAX8 | 7849 | 2 | — | congenital hypothyroidism |
| SMADIP1 | 9839 | 2 | 11595972, 16688751 | syndromic Hirschsprung disease |
| RPRM | 56475 | 2 | 15592418 | tumorigenesis, no suppression of tumor growth |
| SCN1A | 6323 | 2 | 16865694, 16075041 | Severe myoclonic epilepsy of infancy (SMEI) or Dravet syndrome |
| HOXD13 | 3239 | 2 | 12900906 | foot malformations |
| COL3A1 | 1281 | 2 | — | Ehlers-Danlos syndrome type IV, and with aortic and arterial aneurysms |
| SLC40A1 | 30061 | 2 | 16135412 | ferroportin disease |
| SATB2 | 23314 | 2 | — | craniofacial dysmorphologies, cleft palate |
| SUMO1 | 7341 | 2 | 17606301, 16990542 | nonsyndromic cleft lip and palate |
| BMPR2 | 659 | 2 | 11115378 | primary pulmonary hypertension |
| XRCC5 | 7520 | 2 | 16325483 | retarded growth, increased radiosensitivity, elevated p53 levels and shortened telomeres |
| PAX3 | 5077 | 2 | 12070244, 9731536 | developmental delay and autism |
| STK25 | 10494 | 2 | 15521982 | mild-to-moderate mental retardation with an Albright hereditary osteodystrophy-like phenotype |
| CHL1 | 10752 | 3 | — | 3p deletion (3p−) syndrome |
| SRGAP3 | 9901 | 3 | 12195014 | severe mental retardation |
| VHL | 7428 | 3 | 16061637 | increased lung cancer susceptibility |
| GHRL | 51738 | 3 | — | GHRELIN POLYMORPHISM |
| PPARG | 5468 | 3 | 15073042 | susceptibility to mammary, ovarian and skin carcinogenesis |
| SRG3 | 6599 | 3 | 17255092 | proteasomal degradation |
| RASSF1A | 11186 | 3 | 11585766 | pathogenesis of a variety of cancers, no suppression of tumor growth |
| TKT | 7086 | 3 | — | reduced adipose tissue and female fertility |
| MITF | 4286 | 3 | 10952390, 9170159 | Waardenburg syndrome type 2 |
| FOXP1 | 27086 | 3 | — | tumors development |
| ROBO1 | 6091 | 3 | — | predispose to dyslexia |
| DIRC2 | 84925 | 3 | — | onset of tumor growth |
| ATP2C1 | 27032 | 3 | 15811312, 17597066 | orthodisease, skin disorder |
| FOXL2 | 668 | 3 | 11468277 | blepharophimosis syndrome associated with ovarian dysfunction |
| ATR | 545 | 3 | 15282542 | mismatch repair-deficient |
| SI | 6476 | 3 | — | SUCRASE-ISOMALTASE DEFICIENCY, CONGENITAL |

TABLE 1-continued

Genes Associated With Haploinsufficiency Diseases

| Gene Symbol | Entrez Gene ID | Chromosome | PubMed (PMID) | Disorder/Syndrome |
| --- | --- | --- | --- | --- |
| TERC | 7012 | 3 | 16284252, 15326392 | Autosomal dominant dyskeratosis congenita (AD DC), a rare inherited bone marrow failure syndrome |
| SOX2 | 6657 | 3 | 16529618, 15503273 | hippocampal malformations and epilepsy |
| OPA1 | 4976 | 3 | 16735988, 11017080 | optic atrophy |
| TFRC | 7037 | 3 | — | stressed erythropoiesis and neurologic abnormalities |
| FGFR3 | 2261 | 4 | 9199352 | a variety of skeletal dysplasias, including the most common genetic form of dwarfism, achondroplasia |
| LETM1 | 3954 | 4 | 16719275 | Wolf Hirshhorn syndrome |
| SH3BP2 | 6452 | 4 | — | Wolf-Hirschhorn syndrome |
| MSX1 | 4487 | 4 | 14630905 | oligodontia |
| RBPJ | 3516 | 4 | — | embryonic lethality and formation of arteriovenous malformations |
| PHOX2B | 8929 | 4 | — | predispose to Hirschsprung disease |
| ENAM | 10117 | 4 | 15649948 | Amelogenesis imperfecta (inherited defects of dental enamel formation) |
| MAPK10 | 5602 | 4 | — | epileptic encephalopathy of the Lennox-Gaustaut type |
| PKD2 | 5311 | 4 | 16720597, 10615132 | Autosomal dominant polycystic kidney disease |
| SNCA | 6622 | 4 | 12477695 | familial Parkinson's disease |
| RIEG | 5308 | 4 | 9480756 | Rieger syndrome (RIEG) characterized by malformations of the anterior segment of the eye, failure of the periumbilical skin to involute, and dental hypoplasia |
| ANK2 | 287 | 4 | — | arrhythmia |
| MAD2L1 | 4085 | 4 | 17038523 | optimal hematopoiesis |
| PLK4 | 10733 | 4 | 16025114 | mitotic infidelity and carcinogenesis |
| FBXW7 | 55294 | 4 | — | cancer (breast, ovary) tumors development |
| TERT | 7015 | 5 | — | DYSKERATOSIS CONGENITA |
| SEMA5A | 9037 | 5 | 9464278 | abnormal brain development |
| GDNF | 2668 | 5 | 11774071 | complex human diseases (Hirschsprung-like intestinal obstruction and early-onset lethality) |
| FGF10 | 2255 | 5 | 16476029, 15654336 | craniofacial development and developmental disorders |
| PIK3R1 | 5295 | 5 | 10829070 | insulin resistance |
| APC | 324 | 5 | 14691304 | familial adenomatous polyposis |
| RAD50 | 10111 | 5 | 16474176 | hereditary breast cancer susceptibility associated with genomic instability |
| SMAD5 | 4090 | 5 | 12064918 | secondary myelodysplasias and acute myeloid leukemias |
| EGR1 | 1958 | 5 | 17420284 | development of myeloid disorders |
| TCOF1 | 6949 | 5 | 17552945, 16465596, 15930015, 15249688 | depletion of neural crest cell precursors, Treacher Collins syndrome |
| NPM1 | 4869 | 5 | 16341035, 16007073 | myelodysplasias and leukemias |
| NKX2-5 | 1482 | 5 | 16470726, 10398271, 15368344 | microcephaly and congenital heart disease |
| MSX2 | 4488 | 5 | 10742104 | pleiotropic defects in bone growth and ectodermal organ formation |
| NSD1 | 64324 | 5 | 16970856, 16547423, 15720303, 15640245, 15539801, 14631206, 14517949, 12687502, 12676901, 11896389 | Sotos syndrome |

TABLE 1-continued

Genes Associated With Haploinsufficiency Diseases

| Gene Symbol | Entrez Gene ID | Chromosome | PubMed (PMID) | Disorder/Syndrome |
|---|---|---|---|---|
| FOXC1 | 2296 | 6 | 14564054, 11170889 | Axenfeld-Rieger anomaly of the anterior eye chamber |
| DSP | 1832 | 6 | 11841538, 11476106, 10594734, 17475244 | skin fragility/woolly hair syndrome; disruption of tissue structure, integrity and changes in keratinocyte proliferation |
| EEF1E1 | 9521 | 6 | — | no suppression of tumor growth |
| TNXA | 7146 | 6 | 15733269 | Ehlers-Danlos syndrome |
| TNX | 7148 | 6 | 15733269 | Elastic fiber abnormalities in hypermobility type Ehlers-Danlos syndrome |
| HMGA1 | 3159 | 6 | — | insulin resistance and diabetes |
| RUNX2 | 860 | 6 | 16270353, 16187316, 15952089, 15566413, 10204840, 9690033, 9207800 | cleidocranial dysplasia |
| CD2AP | 23607 | 6 | 12764198 | glomerular disease susceptibility |
| ELOVL4 | 6785 | 6 | 17311087, 17254625 | defective skin permeability barrier function and neonatal lethality |
| NT5E | 4907 | 6 | 12805562 | Neuropathy target esterase deficiency |
| SIM1 | 6492 | 6 | 16728530, 10587584 | impaired melanocortin-mediated anorexia and activation of paraventricular nucleus neurons |
| COL10A1 | 1300 | 6 | — | Schmid type metaphyseal chondrodysplasia and Japanese type spondylometaphyseal dysplasia |
| PARK2 | 5071 | 6 | — | PARKINSON DISEASE 2 |
| TWIST1 | 7291 | 7 | 16540516, 16237669, 17003487, 15829502, 11854168 | coronal synostosis |
| GLI3 | 2737 | 7 | 15739154, 14608643, 9054938 | Greig cephalopolysyndactyly and Pallister-Hall syndromes |
| GCK | 2645 | 7 | — | non-insulin dependent diabetes mellitus (NIDDM), maturity onset diabetes of the young, type 2 (MODY2) and persistent hyperinsulinemic hypoglycemia of infancy (PHHI) |
| FKBP6 | 8468 | 7 | 15770126 | Williams-Beuren syndrome |
| ELN | 2006 | 7 | 14556246, 10198167, 16820942, 16784071, 16476938, 12016585, 11735026, 10942104, 10885576, 10780788 | cardiovascular disease and connective tissue abnormalities |
| LIMK1 | 3984 | 7 | 9637430 | Williams syndrome (WS), a neurodevelopmental disorder |
| RFC2 | 5982 | 7 | — | growth deficiency as well as developmental disturbances in Williams syndrome |
| GTF3 | 9569 | 7 | 10573005 | abnormal muscle fatiguability |
| GTF2I | 2969 | 7 | — | Williams-Beuren syndrome |
| NCF1 | 653361 | 7 | 15626477 | autosomal recessive chronic granulomatous disease |
| KRIT1 | 889 | 7 | 12404106 | Cerebral Cavernous Malformations (vascular malformations characterised by abnormally enlarged capillary cavities) |
| COL1A2 | 1278 | 7 | 17898012 | subtle symptoms like recurrent joint subluxation or hypodontia |
| SHFM1 | 7979 | 7 | 17230488 | severe mental retardation, short stature, microcephaly and deafness |
| RELN | 5649 | 7 | 16376115, 11592844 | Cognitive disruption and altered hippocampus synaptic function |

TABLE 1-continued

Genes Associated With Haploinsufficiency Diseases

| Gene Symbol | Entrez Gene ID | Chromosome | PubMed (PMID) | Disorder/Syndrome |
|---|---|---|---|---|
| FOXP2 | 93986 | 7 | 16470794 | Speech and language impairment and oromotor dysprax |
| CAV1 | 857 | 7 | 15816560, 14981899 | 17beta-estradiol-stimulated mammary tumorigenesis |
| ST7 | 7982 | 7 | — | no suppression of tumor growth |
| BRAF | 673 | 7 | — | Cardiofaciocutaneous (CFC) syndrome |
| SHH | 6469 | 7 | 10852374 | Holoprosencephaly, sacral anomalies, and situs ambiguus |
| HLXB9 | 3110 | 7 | 14663834, 12116275 | Currarino syndrome including a presacral mass, sacral agenesis, and anorectal malformation |
| GATA4 | 2626 | 8 | 10096597 | congenital heart disease |
| NKX3-1 | 4824 | 8 | 15734999 | prostate cancer |
| FGFR1 | 2260 | 8 | — | Pfeiffer syndrome, Jackson-Weiss syndrome, Antley-Bixler syndrome, osteoglophonic dysplasia, and autosomal dominant Kallmann syndrome 2 |
| CHD7 | 55636 | 8 | — | CHARGE syndrome |
| CSN5 | 10987 | 8 | 15735686 | TRC8 hereditary kidney cancer |
| EYA1 | 2138 | 8 | — | branchiootorenal dysplasia syndrome, branchiootic syndrome, and sporadic cases of congenital cataracts and ocular anterior segment anomalies |
| TRPS1 | 7227 | 8 | 11285235 | dominantly inherited tricho-rhino-phalangeal (TRP) syndromes |
| DMRT1 | 1761 | 9 | — | failure of testicular development and feminization in male |
| DMRT2 | 10655 | 9 | — | defective testis formation in karyotypic males and impaired ovary function in karyotypic females |
| MLLT3 | 4300 | 9 | — | neuromotor developmental delay, cerebellar ataxia, and epilepsy |
| ARF | 1029 | 9 | 16199529, 12019208 | acute myeloid leukemia |
| CDKN2B | 1030 | 9 | 10388473 | syndrome of cutaneous malignant melanoma and nervous system tumors |
| BAG1 | 573 | 9 | 15560850 | lung tumorigenesis |
| PAX5 | 5079 | 9 | — | pathogenesis of lymphocytic lymphomas |
| GCNT1 | 2650 | 9 | 16778138 | T lymphoma cells resistant to cell death |
| ROR2 | 4920 | 9 | 17632781 | basal cell nevus syndrome (BCNS) |
| PTCH1 | 5727 | 9 | 11922389, 14500378 | Primitive neuroectodermal tumors formation |
| NR5A1 | 2516 | 9 | 14594453 | impaired testicular development, sex reversal, and adrenal failure |
| LMX1B | 4010 | 9 | 15774843, 11668639, 9837817 | nail-patella syndrome |
| ENG | 2022 | 9 | 15718503, 16470589 | Hereditary hemorrhagic telangiectasia type 1 |
| TSC1 | 7248 | 9 | 14633685 | transitional cell carcinoma of the bladder |
| COL5A1 | 1289 | 9 | 16431952, 11391664, 10777716 | Structural abnormalities of the cornea and lid |
| NOTCH1 | 4851 | 9 | 16601454 | aortic valve disease (cardiac malformation and aortic valve calcification) |
| EHMT1 | 79813 | 9 | 16826528, 15805155 | 9q34 subtelomeric deletion syndrome |
| KLF6 | 1316 | 10 | 17297474 | cellular growth dysregulation and tumorigenesis |

TABLE 1-continued

Genes Associated With Haploinsufficiency Diseases

| Gene Symbol | Entrez Gene ID | Chromosome | PubMed (PMID) | Disorder/Syndrome |
|---|---|---|---|---|
| GATA3 | 2625 | 10 | 17046739, 16817354, 15994092, 15705923, 11577985, 11389161 | HDR (hypoparathyroidism, deafness and renal dysplasia) syndrome |
| ANX7 | 310 | 10 | 14608035 | tumorigenesis |
| PTEN | 5728 | 10 | 16938570, 16793127, 16738322, 16288012, 16027169, 15466193, 15001465, 12569555, 12461751, 11553783, 9697695, 12011252 | prostate cancer high-grade prostatic intra-epithelial neoplasias |
| PAX2 | 5076 | 10 | 14569086 | renal-coloboma syndrome |
| FGF8 | 2253 | 10 | 17448458 | several human craniofacial disorders |
| BUB3 | 9184 | 10 | 16600919 | short life span that is associated with the early onset of aging-related features |
| CDKN1C | 1028 | 11 | 10424812 | Beckwith-Wiedemann syndrome |
| NUP98 | 4928 | 11 | — | destruction of securin in mitosis |
| PAX6 | 5080 | 11 | 16866875, 16719277, 16717455, 15480875, 15057935, 12782766, 12552561, 11920832, 11431688, 16646034 | eye diseases |
| WT1 | 7490 | 11 | 8827067, 17931563 | congenital genitourinary (GU) anomalies and/or bilateral disease and tumorigenesis |
| EXT2 | 2132 | 11 | 11137991 | type II form of multiple exostoses |
| ALX4 | 60529 | 11 | 15057119, 9636085 | Tibial aplasia, lower extremity mirror image polydactyly, brachyphalangy, craniofacial dysmorphism and genital hypoplasia |
| FEN1 | 2237 | 11 | 16978612 | neuromuscular and neurodegenerative diseases |
| SF1 | 7536 | 11 | 17940071, 17200175 | mild gonadal dysgenesis and impaired androgenization |
| FGF3 | 2248 | 11 | 17656375 | otodental syndrome |
| FZD4 | 8322 | 11 | 17103440 | complex chromosome rearrangement with multiple abnormalities including growth retardation, facial anomalies, exudative vitreoretinopathy (EVR), cleft palate, and minor digital anomalies |
| ATM | 472 | 11 | 10571946, 10363981 | High incidence of cancer |
| H2AX | 3014 | 11 | 12914700 | genomic instability, early onset of various tumors |
| FLI1 | 2313 | 11 | 15525489 | Paris-Trousseau thrombopenia |
| NFRKB | 4798 | 11 | 11920839 | cellular immunodeficiency, pancytopenia, malformations |
| PHB2 | 11331 | 12 | — | enhanced estrogen receptor function |
| ETV6 | 2120 | 12 | 16643428 | a paediatric pre-B acute lymphoblastic leukaemia |
| CDKN1B | 1027 | 12 | 16951165, 11042700, 10935480 | ErbB2-induced mammary tumor growth |
| COL2A1 | 1280 | 12 | 10819645 | Stickler syndrome |
| KRT5 | 3852 | 12 | — | epidermolysis bullosa simplex |
| MYF6 | 4618 | 12 | 11053684 | myopathy and severe course of Becker muscular dystrophy |
| IGF1 | 3479 | 12 | 15769976 | subtle inhibition of intrauterine and postnatal growth |
| SERCA2 | 488 | 12 | 17116488, 16204033, 11389134 | colon and lung cancer |
| TBX5 | 6910 | 12 | 15289437, 12789647, 12736217, 11572777 | maturation failure of conduction system morphology and function in Holt-Oram syndrome |
| TBX3 | 6926 | 12 | 17265068, 16896345, 12668170, 12376101, 12116211 | ulnar-mammary syndrome |

TABLE 1-continued

Genes Associated With Haploinsufficiency Diseases

| Gene Symbol | Entrez Gene ID | Chromosome | PubMed (PMID) | Disorder/Syndrome |
| --- | --- | --- | --- | --- |
| HNF1A | 6927 | 12 | 14633861, 12530534 | reduced serum apolipoprotein M levels |
| BRCA2 | 675 | 13 | 15172125 | predisposed to breast, ovarian, pancreatic and other cancers |
| FKHR | 2308 | 13 | 15489287 | Alveolar rhabdomyosarcomas |
| RB1 | 5925 | 13 | 12531801 | Metaphase cytogenetic abnormalities |
| ZIC2 | 7546 | 13 | 11699604, 11285244 | neurological disorderss, behavioral abnormalities |
| LIG4 | 3981 | 13 | — | LIG4 syndrome, nonlymphoid tumorigenesis |
| COCH | 1690 | 14 | 16078052 | unknown |
| NPAS3 | 64067 | 14 | 12746393 | schizophrenia |
| NKX2-1 | 7080 | 14 | — | Choreoathetosis, hypothyroidism, pulmonary alterations, neurologic phenotype and secondary hyperthyrotropinemia, and diseases due to transcription factor defects |
| PAX9 | 5083 | 14 | 16479262, 16333316, 11941488, 11781684 | posterior tooth agenesis |
| BMP4 | 652 | 14 | 16835935 | a contiguous gene syndrome comprising anophthalmia, pituitary hypoplasia, and ear anomalies |
| GCH1 | 2643 | 14 | — | malignant hyperphenylalaninemia and dopa-responsive dystonia |
| SIX6 | 4990 | 14 | 10512683 | bilateral anophthalmia and pituitary anomalies |
| RAD51B | 5890 | 14 | 16778173 | centrosome fragmentation and aneuploidy |
| BCL11B | 64919 | 14 | 17306224 | suppression of lymphomagenesis and thymocyte development |
| SPRED1 | 161742 | 15 | — | neurofibromatosis type 1-like syndrome |
| BUBR1 | 701 | 15 | 14744753 | enhanced tumor development |
| DLL4 | 54567 | 15 | — | embryonic lethality due to major defects in arterial and vascular development |
| FBN1 | 2200 | 15 | — | Marfan syndrome, isolated ectopia lentis, autosomal dominant Weill-Marchesani syndrome, MASS syndrome, and Shprintzen-Goldberg craniosynostosis syndrome |
| ALDH1A2 | 8854 | 15 | — | facilitate posterior organ development and prevent spina bifida |
| TPM1 | 7168 | 15 | — | type 3 familial hypertrophic cardiomyopathy |
| P450SCC | 1583 | 15 | 11502818 | 46, XY sex reversal and adrenal insufficiency |
| BLM | 641 | 15 | 12242442 | the autosomal recessive disorder Bloom syndrome |
| COUP-TFII | 7026 | 15 | 15384084 | several malformations, pre- and postnatal growth retardation and developmental |
| SOX8 | 30812 | 16 | — | the mental retardation found in ATR-16 syndrome |
| TSC2 | 7249 | 16 | 16027168, 12100629 | differential cancer susceptibility |
| PKD1 | 5310 | 16 | — | autosomal dominant polycystic kidney disease |
| CBP | 1387 | 16 | 11962765 | Rubinstein-Taybi syndrome |
| SOCS1 | 8651 | 16 | 15197228 | severe liver fibrosis and hepatitis-induced carcinogenesis |
| PRM2 | 5620 | 16 | — | infertility |
| PRM1 | 5619 | 16 | — | infertility |
| ABCC6 | 368 | 16 | — | pseudoxanthoma elasticum |
| ERAF | 51327 | 16 | — | subtle erythroid phenotype |

TABLE 1-continued

Genes Associated With Haploinsufficiency Diseases

| Gene Symbol | Entrez Gene ID | Chromosome | PubMed (PMID) | Disorder/Syndrome |
|---|---|---|---|---|
| SALL1 | 6299 | 16 | 16429401 | Townes-Brocks syndrome |
| CBFB | 865 | 16 | 17022082 | delayed cranial ossification, cleft palate, congenital heart anomalies, and feeding difficulties |
| CTCF | 10664 | 16 | 17962299, 15761865 | loss of imprinting of insulin-like growth factor-II in Wilms tumor |
| WWOX | 51741 | 16 | 17575124 | initiation of tumor development |
| FOXF1 | 2294 | 16 | 11943666 | defects in formation and branching of primary lung buds |
| FOXC2 | 2303 | 16 | 16910099, 16081467, 15624441, 12719382, 11694548, 11078474 | the lymphatic/ocular disorder Lymphedema-Distichiasis |
| YWHAE | 7531 | 17 | — | pathogenesis of small cell lung cancer |
| HIC1 | 3090 | 17 | 16724116 | Miller-Dieker syndrome |
| LIS1 | 5048 | 17 | 17148952, 16642511, 9760204 | abnormal cell proliferation, migration and differentiation in the adult dentate gyrus |
| P53 | 7157 | 17 | 15583690, 12517413, 12467136, 11695559, 11532857, 11319275 | male oral squamous cell carcinomas |
| PMP22 | 5376 | 17 | 15955700 | hereditary neuropathy with liability to pressure palsies |
| COPS3 | 8533 | 17 | 10851253 | Circadian rhythm abnormalities of melatonin in Smith-Magenis syndrome |
| RAI1 | 10743 | 17 | 17041942, 17024248, 16845274, 15690371, 15565467 | Smith-Magenis syndrome |
| TOP3A | 7156 | 17 | — | Smith-Magenis syndrome |
| SHMT1 | 6470 | 17 | — | Smith-Magenis syndrome |
| RNF135 | 84282 | 17 | 17632510 | phenotypic abnormalities including overgrowth |
| NF1 | 4763 | 17 | 16893911, 16835260, 15804420, 15676286, 15103551, 12124168, 9187663, 17103458 | neurofibromatosis type 1 |
| SUZ12 | 23512 | 17 | — | mental impairment in constitutional NF1 microdeletions |
| MEL-18 | 7703 | 17 | 12196719 | breast carcinogenesis |
| KLHL10 | 317719 | 17 | — | disrupted spermiogenesis |
| STAT5B | 6777 | 17 | 15870688 | striking amelioration of IL-7-induced mortality and disease development |
| STAT5A | 6776 | 17 | 15870688 | striking amelioration of IL-7-induced mortality and disease development |
| BECN1 | 8678 | 17 | — | autophagy function, and tumor suppressor function |
| BRCA1 | 672 | 17 | 17420720, 17404506, 15289302 | shortened life span and ovarian tumorigenesis |
| PGRN | 2896 | 17 | 17168647, 16862115 | neurodegeneration |
| MAPT | 4137 | 17 | — | neuronal cell death, neurodegenerative disorders such as Alzheimer's disease, Pick's disease, frontotemporal dementia, cortico-basal degeneration and progressive supranuclear palsy |
| CSH1 | 1442 | 17 | 14642004 | Silver-Russell syndrome |
| POLG2 | 11232 | 17 | — | mtDNA deletions causes COX deficiency in muscle fibers and results in the clinical phenotype |
| PRKAR1A | 5573 | 17 | 15371594 | Carney complex, a familial multiple neoplasia syndrome |
| SOX9 | 6662 | 17 | 17142326, 11606049, 8894698, 8001137 | skeletal dysplasias |

TABLE 1-continued

Genes Associated With Haploinsufficiency Diseases

| Gene Symbol | Entrez Gene ID | Chromosome | PubMed (PMID) | Disorder/Syndrome |
|---|---|---|---|---|
| NHERF1 | 9368 | 17 | 17078868 | breast tumours |
| FSCN2 | 25794 | 17 | 16043865 | photoreceptor degeneration, autosomal dominant retinitis pigmentosa |
| DSG1 | 1828 | 18 | 17194569 | diseases of epidermal integrity |
| DSG2 | 1829 | 18 | — | ARRHYTHMOGENIC RIGHT VENTRICULAR DYSPLASIA |
| TCF4 | 6925 | 18 | 17478476 | Pitt-Hopkins syndrome, a syndromic mental disorder |
| FECH | 2235 | 18 | 10068685 | protoporphyria |
| MC4R | 4160 | 18 | 12851322, 12639913, 10598807 | increased adiposity and linear growth |
| GALR1 | 2587 | 18 | — | uncontrolled proliferation and neoplastic transformation |
| SALL3 | 27164 | 18 | — | 18q deletion syndrome |
| LKB1 | 6794 | 19 | 12218179 | Peutz-Jeghers syndrome |
| PNPLA6 | 10908 | 19 | 15094302 | organophosphorus-induced hyperactivity and toxicity |
| RYR1 | 6261 | 19 | — | malignant hyperthermia susceptibility, central core disease, and minicore myopathy with external ophthalmoplegia |
| TGFB1 | 7040 | 19 | 17114585 | Aggressive pancreatic ductal adenocarcinoma |
| RPS19 | 6223 | 19 | — | Diamond-Blackfan anemia |
| DMPK | 1760 | 19 | 10021468 | cardiac disease in myotonic dystrophy |
| CRX | 1406 | 19 | 10892846 | photoreceptor degeneration, Leber congenital amaurosis type III and the autosomal dominant cone-rod dystrophy 2 |
| PRPF31 | 26121 | 19 | — | retinitis pigmentosa with reduced penetrance |
| JAG1 | 182 | 20 | 11861489, 11139239, 10590916, 17786115, 11152664, 10534349 | Alagille syndrome |
| PAX1 | 5075 | 20 | 12774041 | Klippel-Feil syndrome |
| GDF5 | 8200 | 20 | 16532400, 12357473 | Multiple-synostosis syndrome |
| HNF4A | 3172 | 20 | 10905494 | monogenic autosomal dominant non-insulin-dependent diabetes mellitus type I |
| SALL4 | 57167 | 20 | 16790473 | Okihiro syndrome |
| MC3R | 4159 | 20 | — | susceptibility to obesity |
| RAE1 | 8480 | 20 | 16355229 | premature separation of sister chromatids, severe aneuploidy and untimely degradation of securin |
| GNAS | 2778 | 20 | 17652219, 15579796 | reduced activation of a downstream target in epithelial tissues |
| EDN3 | 1908 | 20 | — | Hirschsprung disease |
| KCNQ2 | 3785 | 20 | 12700166 | epilepsy susceptibility |
| SOX18 | 54345 | 20 | 17290276 | mental retardation |
| SLC5A3 | 6526 | 21 | — | brain inositol deficiency |
| RUNX1 | 861 | 21 | 17394134, 16364766, 15339695, 15061191, 11830488, 11721958, 15297309, 14556655, 11756147, 10684580 | The 8p11 myeloproliferative syndrome |
| DYRK1A | 1859 | 21 | 12192061 | neurological defects, developmental delay |
| COL6A1 | 1291 | 21 | — | autosomal dominant disorder, Bethlem myopathy |
| PRODH | 5625 | 22 | 17028864 | 22q11 Deletion syndrome |
| DGCR2 | 9993 | 22 | — | DiGeorge syndrome |
| HIRA | 7290 | 22 | 9063745, 8111380 | DiGeorge syndrome (cranio-facial, cardiac and thymic malformations) |
| TBX1 | 6899 | 22 | 16969581, 16684884, 15778864, 12539040, 12351571, 11242049 | 22q11 deletion syndrome and schizophrenia |

TABLE 1-continued

Genes Associated With Haploinsufficiency Diseases

| Gene Symbol | Entrez Gene ID | Chromosome | PubMed (PMID) | Disorder/Syndrome |
|---|---|---|---|---|
| COMT | 1312 | 22 | 16848928 | 22q11.2 deletion syndrome |
| RTN4R | 65078 | 22 | — | schizophrenia susceptibility (schizoaffective disorders are common features in patients with DiGeorge/velocardiofacial syndrome) |
| PCQAP | 51586 | 22 | 11414760 | DiGeorge syndrome |
| LZTR1 | 8216 | 22 | — | DiGeorge syndrome |
| INI1 | 6598 | 22 | 16912184 | pituitary tumorigenesis |
| MYH9 | 4627 | 22 | 16162639 | hematological abnormalities |
| SOX10 | 6663 | 22 | 11641219 | the etiology of Waardenburg/Hirschsprung disease |
| FBLN1 | 2192 | 22 | — | limb malformations |
| PPARA | 5465 | 22 | — | prostate cancer |
| PROSAP2 | 85358 | 22 | 11431708, 12065602 | The terminal 22q13.3 deletion syndrome, characterized by severe expressive-language delay, mild mental retardation, hypotonia, joint laxity, dolichocephaly, and minor facial dysmorphisms |
| SHOX | 6473 | X | 17881654, 17726696, 16776105, 16319696, 15356038, 15173321, 15118270, 14981722, 14557470, 14513876, 14513875, 12673642, 12510982, 12439897, 12116254, 12035792, 11889214, 11701728, 11546827, 11523902, 11503163, 11408757, 11134233, 10905666, 10878753, 10842291, 10798359, 10749976, 10599728 | congenital form of growth failure, the aetiology of "idiopathic" short stature and the growth deficits and skeletal anomalies in Leri Weill, Langer and Turner syndrome |
| P2RY8 | 286530 | X | 15466006 | mentally retarded males |
| NLGN4X | 57502 | X | — | autism and Asperger syndrome |
| TRAPPC2 | 6399 | X | — | spondyloepiphyseal dysplasia tarda |
| RPS4X | 6191 | X | — | unknown |
| CSF2RA | 1438 | X | 8950669 | growth deficiency |
| CHRDL1 | 91851 | X | 3196642 | topographic retinotectal projection and in the regulation of retinal angiogenesis in response to hypoxia |
| SF3B4 | 10262 | 1 | 24003905, 27127115, | Nager syndrome, Hepatocellular carcinoma and Rodriguez Acrofacial Dysotosis |
| CTNND2 | 1501 | 5 | 29127138, 25839933 | Intellectual disability, epilepsy |
| AAGAB | 79719 | 15 | 26608363, 25771163 | Buschke-Fischer-Brauer and punctate palmoplantar keratoderma |
| ABCD1 | 215 | X | 26454440, 29136088 | adrenoleukodystrophy |
| AKT3 | 10000 | 1 | 28969385, 27297869 | Developmental disorders and breast cancer |
| ANKRD11 | 29123 | 16 | 28422132, 27605097 | KBG syndrome |
| ANOS1 | 3730 | X | 28780519, 25892360 | Kallmann syndrome |
| AP1S2 | 8905 | X | 17617514, 23756445, | Mental retardation |
| AR | 367 | X | 29051026 | Kennedy's disease and androgen insensitivity |
| ARSE | 415 | X | 20301713, 23470839 | chondrodysplasia punctata |
| ARX | 170302 | X | 25044608 | cognitive disability and epilepsy |
| ASXL1 | 171023 | 20 | 27616637 | myelodysplastic syndromes and chronic myelomonocytic leukemia |
| ATP7A | 538 | X | 22992316, 24754450 | Menkes disease, X-linked distal spinal muscular atrophy, and occipital horn syndrome |
| ATP8A2 | 51761 | 13 | 20683487 | cerebellar ataxia and cognitive disabilities |
| ATRX | 546 | X | 20301622 | cognitive disabilities as well as alpha-thalassemia (ATRX) syndrome |

TABLE 1-continued

Genes Associated With Haploinsufficiency Diseases

| Gene Symbol | Entrez Gene ID | Chromosome | PubMed (PMID) | Disorder/Syndrome |
|---|---|---|---|---|
| AUTS2 | 26053 | 7 | 26717414 | autism spectrum disorders, intellectual disability, and developmental delay |
| AVPR2 | 554 | X | 27565746, 27117808 | Nephrogenic Diabetes Insipidus (NDI) |
| BAG3 | 9531 | 10 | 28211974 | cardiomyopathy |
| BCL11A | 53335 | 2 | 28891213 | Autism and intellectual development |
| BCOR | 54880 | X | 26573325 | sarcoma of the kidney |
| BMPR1A | 657 | 10 | 26383923 | Intellectual disability |
| BRWD3 | 254065 | X | 24462886, 17668385 | cognitive disabilities and X-linked macrocephaly |
| BTK | 695 | X | 19039656 | agammaglobulinemia |
| CACNA1C | 775 | 12 | 28493952, 26204268 | Autism |
| CASK | 8573 | X | 28783747, 24927672 | FG syndrome 4, intellectual disability and microcephaly |
| CDH1 | 999 | 16 | 26182300 | breast, colorectal, thyroid, gastric and ovarian cancer |
| CDKL5 | 6792 | X | 27265524, 26701947 | infantile spasm syndrome (ISSX), also known as X-linked West syndrome, and Rett syndrome (RTT). |
| CHD2 | 1106 | 15 | 26677509 | Neurodevelopmental disorders |
| CHD8 | 57680 | 14 | 26921529, 25989142, 2673379 | Autism |
| CHM | 1121 | X | 27820636 | choroideremia |
| CHRM3 | 1131 | 1 | 26959877 | Schizophrenia |
| CLCN5 | 1184 | X | 27117801, 29058463 | Dent disease and renal tubular disorders complicated by nephrolithiasis |
| CNKSR2 | 22866 | X | 22511892 | Intellectual disability |
| CNTN4 | 152330 | 3 | 21308999 | autism spectrum disorders |
| CNTNAP2 | 26047 | 7 | 27439707 | neurodevelopmental disorders, including Gilles de la Tourette syndrome, schizophrenia, epilepsy, autism, ADHD and intellectual disability |
| COL11A1 | 1301 | 1 | 21035103 | Fibrochondrogenesis, Stickler syndrome and with Marshall syndrome |
| COL1A1 | 1277 | 17 | 28102596 | imperfecta types I-IV, Ehlers-Danlos syndrome type VIIA, Ehlers-Danlos syndrome Classical type, Caffey Disease and idiopathic osteoporosis |
| CREBBP | 1387 | 16 | 27342041 | Rubinstein-Taybi syndrome (RTS) and acute myeloid leukemia |
| CRYBB2 | 1415 | 22 | 25489230, 25964531 | Cataracts and prostate cancer |
| CUL4B | 8450 | X | 24898194 | Intellectual disability |
| CYBB | 1536 | X | 27917630 | chronic granulomatous disease (CGD |
| DCX | 1641 | X | 25868952 | pilepsy, cognitive disability, subcortical band heterotopia and lissencephaly syndrome |
| DICER1 | 23405 | 14 | 24761742 | familial tumor susceptibility syndrome |
| DKC1 | 1736 | X | 27570172, 25499969 | X-linked dyskeratosis congenita |
| DLG3 | 1741 | X | 19795139 | cognitive disability |
| DMD | 1756 | X | 28247318 | uchenne muscular dystrophy (DMD), Becker muscular dystrophy (BMD), and cardiomyopathy |
| DSC2 | 1824 | 18 | 26310507 | arrhythmogenic right ventricular dysplasia-11, and cancer |
| EBP | 10682 | X | 22121851 | Chondrodysplasia punctata 2 |
| EDNRB | 1910 | 13 | 8852658 | Hirschsprung disease type 2 |
| EDA | 1896 | X | 25846883 | X-linked hypohidrotic ectodermal dysplasia |
| EFNB1 | 1947 | X | 15959873 | craniofrontonasal syndrome |
| EFTUD2 | 9343 | 17 | 26507355 | mandibulofacial dysostosis with microcephaly |

TABLE 1-continued

Genes Associated With Haploinsufficiency Diseases

| Gene Symbol | Entrez Gene ID | Chromosome | PubMed (PMID) | Disorder/Syndrome |
| --- | --- | --- | --- | --- |
| EMX2 | 2018 | 10 | 8528262 | schizencephaly |
| EP300 | 2033 | 22 | 25712426 | Rubinstein-Taybi syndrome and epithelial cancer |
| ERF | 2077 | 19 | 26097063 | craniosynostosis |
| ERMARD | 55780 | 6 | 24056535 | Periventricular nodular heterotopia |
| EXT1 | 2131 | 8 | 24009674 | Multiple osteochondromas |
| EYA4 | 2070 | 6 | 15735644 | Cardiomyopathy and hearing loss |
| F8 | 2157 | X | 28777843 | hemophilia A |
| F9 | 2158 | X | 28007939 | hemophilia B or Christmas disease |
| FAM58A | 92002 | X | 18297069 | STAR syndrome |
| FANCB | 2187 | X | 21910217 | VACTERL syndrome |
| FAS | 355 | 10 | 21490157 | Autoimmune lymphoproliferative syndrome |
| FGD1 | 2245 | X | 27199457 | dysplasia in Aarskog-Scott syndrome and a syndromatic form of X-linked cognitive disability |
| FLCN | 201163 | 17 | 28970150 | Birt-Hogg-Dube syndrome |
| FLG | 2312 | 1 | 21514438 | ichthyosis vulgaris |
| FLNA | 2316 | X | 22238415 | Periventricular nodular heterotopias, otopalatodigital syndromes, frontometaphyseal dysplasia, Melnick-Needles syndrome, and X-linked congenital idiopathic intestinal pseudoobstruction |
| FOXG1 | 2290 | 14 | 28851325 | Rett syndrome |
| FRMD7 | 90167 | X | 25678693 | congenital nystagmus |
| FTSJ1 | 24140 | X | 18401546 | cognitive disability |
| GATA2 | 2624 | 3 | 21670465, 21892158 | monocytopenia and mycobacterial infection syndrome and Emberger syndrome |
| GATA6 | 2627 | 18 | 25706805 | congenital defects and cardiomyopathy |
| GDI1 | 2664 | X | 21736009 | cognitive disability |
| GJA5 | 2702 | 1 | 25992486 | atrial fibrillation |
| GJA8 | 2703 | 1 | 28526010 | zonular pulverulent cataracts, nuclear progressive cataracts, and cataract-microcornea syndrome |
| GK | 2710 | X | 10851254 | glycerol kinase deficiency |
| GLA | 2717 | X | 28723748 | Fabry disease |
| GLI2 | 2736 | 2 | 25974718 | Greig cephalopolysyndactyly syndrome, Pallister-Hall syndrome, preaxial polydactyly type IV, postaxial polydactyly types A1 and B |
| GLMN | 11146 | 1 | 15689436 | glomuvenous malformations |
| GPC3 | 2719 | X | 28371070 | Simpson-Golabi-Behmel syndrome |
| GRIA3 | 2892 | X | 19449417 | Intellectual disability |
| GRIN2A | 2903 | 16 | 27683935 | epilepsy and speech disorder |
| GRIN2B | 2904 | 12 | 27818011 | neurodevelopmental disorders autism, attention deficit hyperactivity disorder, epilepsy and schizophrenia |
| HCCS | 3052 | X | — | microphthalmia syndrome |
| HDAC4 | 9759 | 2 | 20691407 | Mental retardation |
| HMGA2 | 8091 | 12 | 25809938 | Silver-Russell syndrome |
| HNF1B | 6928 | 17 | 27838256 | Intellectual disability |
| HNRNPK | 3190 | 9 | 26173930 | Intellectual disability |
| HPRT1 | 3251 | X | 29185864 | Lesch-Nyhan syndrome or gout |
| HNRNPU | 3192 | 1 | 28393272 | epileptic encephalopathy and intellectual disability |

TABLE 1-continued

Genes Associated With Haploinsufficiency Diseases

| Gene Symbol | Entrez Gene ID | Chromosome | PubMed (PMID) | Disorder/Syndrome |
|---|---|---|---|---|
| IDS | 3423 | X | 27246110 | Hunter syndrome |
| IGF1R | 3480 | 15 | 21811077 | Familial short stature |
| IKBKG | 8517 | X | 27037530 | inncontinentia pigmenti, hypohidrotic ectodermal dysplasia, and immunodeficiencies |
| IL1RAPL1 | 11141 | X | 21933724 | intellectual disability |
| KANSL1 | 284058 | 17 | 20301783 | intellectual disability |
| KAT6B | 23522 | 10 | 26334766 | Say-Barber-Biesecker/Young-Simpson syndrome |
| KCNH2 | 3757 | 7 | 24530480 | long QT syndrome type 2 |
| KDM5C | 8242 | X | 25666439 | cognitive disability |
| KDM6A | 7403 | X | 23076834 | Kabuki syndrome |
| KIAA2022 | 340533 | X | 27358180 | cognitive disability and epilepsy |
| KIF11 | 3832 | 10 | 22653704 | microcephaly |
| KMT2A | 4297 | 11 | 28911906 | Acute lymphoid leukemias and acute myeloid leukemias |
| KMT2D | 8085 | 12 | 27530205 | Kabuki syndrome |
| L1CAM | 3897 | X | | Masa syndrome and L1 syndrome |
| LAMP2 | 3920 | X | 28627787 | Danon disease |
| LDLR | 3949 | 19 | 28873201 | Familial hypercholesterolemia |
| LEMD3 | 23592 | 12 | 26694706 | Buschke-Ollendorff syndrome and melorheostosis |
| LHX4 | 89884 | 1 | 25871839 | hypopituitarism |
| LMNA | 4000 | 1 | 20127487 | cardiomyopathy |
| LRP5 | 4041 | 11 | 27228167 | familial exudative vitreoretinopathy |
| MAGEL2 | 54551 | 15 | 26365340, | Prader-Willi syndrome (PWS) |
| MAGT1 | 84061 | X | 24130152 | intellectual disability |
| MAOA | 4128 | X | 8211186 | Mental retardation |
| MAP2K2 | 5605 | 19 | 25487361 | cardiofaciocutaneous syndrome |
| MBD5 | 55777 | | 27786435, 25271084, 24885232 | Microcephaly, intellectual disabilities, speech impairment, and seizures |
| MECP2 | 4204 | X | 29141583 | Rett syndrome |
| MED13L | 23389 | 12 | 28371282, 28645799 | Intellectual disability |
| MEF2C | 4208 | 5 | 27255693 | cognitive disability, epilepsy, and cerebral malformation |
| MEIS2 | 4212 | 15 | 25712757 | Intellectual disability |
| MEN1 | 4221 | 11 | 9510467, 15105049, 21763627 | Multiple Endocrine Neoplasia type 1 |
| MID1 | 4281 | X | 25304119 | Opitz syndrome |
| MLH1 | 4292 | 3 | 15942939 | colon cancer |
| MNX1 | 3110 | 7 | 24095820 | Currarino syndrome |
| MSH2 | 4436 | 2 | 26498247 | hereditary nonpolyposis colon cancer |
| MSH6 | 2956 | 2 | 6099011 | hereditary nonpolyposis colon cancer, colorectal cancer, and endometrial cancer |
| MTAP | 4507 | 9 | 22464254 | diaphyseal medullary stenosis with malignant fibrous histiocytoma (DMSMFH). |
| MTM1 | 4534 | X | 21488203 | X-linked myotubular myopathy |
| MYBPC3 | 4607 | 11 | 27348999 | familial hypertrophic cardiomyopathy |
| MYLK | 4638 | 3 | 28602422 | Megacystis Microcolon Intestinal Hypoperistalsis Syndrome |
| MYT1L | 23040 | 2 | 22547139 | schizophrenia |
| NDP | 4693 | X | 27217716 | Norrie disease |
| NF2 | 4771 | 22 | 11159946 | neurofibromatosis type II |
| NFIX | 4784 | 19 | 26200704 | Marshall-Smith syndrome or Sotos-like syndrome |
| NHS | 4810 | X | 28557584 | Nance-Horan syndrome |
| NIPBL | 25836 | 5 | 26701315 | Cornelia de Lange syndrome |
| NODAL | 4838 | 10 | 19064609 | Cardiovascular malformations |
| NOG | 9241 | 17 | 25391606 | symphalangism (SYM1) and multiple synostoses syndrome (SYNS1) |

TABLE 1-continued

Genes Associated With Haploinsufficiency Diseases

| Gene Symbol | Entrez Gene ID | Chromosome | PubMed (PMID) | Disorder/Syndrome |
|---|---|---|---|---|
| NR0B1 | 190 | X | 25968435 | congenital adrenal hypoplasia and hypogonadotropic hypogonadism |
| NRXN1 | 9378 | 2 | 26279266 | Pitt-Hopkins-like syndrome-2 and schizophrenia |
| NSDHL | 50814 | X | 26014843 | CHILD syndrome |
| NXF5 | 55998 | X | 11566096 | Mental retardation |
| NYX | 60506 | X | 26234941 | X-linked congenital stationary night blindness |
| OCRL | 4952 | X | 27059748 | oculocerebrorenal syndrome of Lowe and also Dent disease |
| OFD1 | 8481 | X | 28371265 | oral-facial-digital syndrome type I and Simpson-Golabi-Behmel syndrome type 2 |
| OPHN1 | 4983 | X | 17845870 | X-linked cognitive disability |
| OTC | 5009 | X | 26446336 | Hyperammonemia |
| OTX2 | 5015 | 14 | 27299576, 28388256 | syndromic microphthalmia 5 and pituitary hormone deficiency 6 |
| PAFAH1B1 | 5048 | 17 | 11754098 | Lissencephaly |
| PAK2 | 5062 | 3 | 21841781 | intellectual disability |
| PAK3 | 5063 | X | 18523455 | intellectual disability |
| PCDH19 | 57526 | X | 27179713 | epileptic encephalopathy and autism |
| PDHA1 | 5160 | X | 10679936 | X-linked Leigh syndrome |
| PGK1 | 5230 | X | 16567715 | neurological impairment |
| PHEX | 5251 | X | 27840894 | Hypophospatemic rickets |
| PHF6 | 84295 | X | 22190899 | cognitive disability and epilepsy |
| PHF8 | 23133 | X | 17594395 | Mental retardation and cleft palate |
| PIGA | 5277 | X | 24706016 | encephalopathies |
| PITX3 | 5309 | 10 | 16565358 | Ocular and neurological disorders |
| PKP2 | 5318 | 12 | 27030002 | cardiomyopathy |
| PLP1 | 5354 | X | 27793435 | Pelizaeus-Merzbacher disease and spastic paraplegia type 2 |
| POLR1D | 51082 | 13 | 24603435 | Treacher Collins syndrome (TCS) |
| PORCN | 64840 | X | 23696273 | focal dermal hypoplasia |
| PQBP1 | 10084 | X | 21204222 | cognitive disability |
| PRPS1 | 5631 | X | 26089585 | Charcot-Marie-Tooth disease and Arts syndrome |
| PRRT2 | 112476 | 16 | 22744660 | paroxysmal kinesigenic dyskinesias |
| PTHLH | 5744 | 12 | 26733284 | osteochondoplasia |
| PTPN11 | 5781 | 12 | 28328117 | Noonan syndrome |
| RAB39B | 116442 | X | 20159109 | cognitive disability, epilepsy, and macrocephaly |
| RASA1 | 5921 | 5 | 26969842 | capillary malformations and Parkes Weber syndrome |
| RBFOX1 | 54715 | 16 | 26174448 | Epilepsy |
| RET | 5979 | 10 | — | Hirschsprung disease |
| RP2 | 6102 | X | 16969763 | Retinal dystrophies |
| RPS17 | 6218 | 15 | 23812780 | Diamond-Blackfan anemia |
| RPS24 | 6229 | 10 | 17186470 | Diamond-Blackfan anemia |
| RPS26 | 6231 | 12 | 22045982 | Diamond-Blackfan anemia |
| RPS6KA3 | 6197 | X | 26297579 | Coffin-Lowry syndrome |
| RS1 | 6247 | X | 26043410 | retinoschisis |
| SCN2A | 6326 | 2 | 26291284 | Epilepsy and autism |
| SCN5A | 6331 | 3 | 28069705 | Long QT syndrome type 3 |
| SDHAF2 | 54949 | 11 | 21224366 | paraganglioma |
| SDHB | 6390 | 1 | 27839933 | paraganglioma |
| SDHC | 6391 | 1 | 26652933 | paraganglioma |
| SDHD | 6392 | 11 | 28924001 | paraganglioma |
| SETBP1 | 26040 | 18 | 28346496 | Schinzel-Giedion syndrome |
| SETD5 | 55209 | 3 | 27375234 | Intellectual disability |
| SGCE | 8910 | 7 | 26783545 | Myoclonus dystonia |
| SH2B1 | 25970 | 16 | 23160192 | Maladaptive behaviors and obesity |
| SH2D1A | 4068 | X | — | Lymphoproliferative syndrome |
| SIX3 | 6496 | 2 | 19346217 | holoprosencephaly |
| SLC16A12 | 387700 | 10 | 18304496 | Juvenile cataracts and renal glucosuria |

TABLE 1-continued

Genes Associated With Haploinsufficiency Diseases

| Gene Symbol | Entrez Gene ID | Chromosome | PubMed (PMID) | Disorder/Syndrome |
| --- | --- | --- | --- | --- |
| SLC16A2 | 6567 | X | 27805744 | Allan-Herndon-Dudley syndrome |
| SLC2A1 | 6513 | 1 | 25532859 | Paroxysmal exertion-induced dyskinesia |
| SLC4A10 | 57282 | 2 | 18413482 | Epilepsy and mental retardation |
| SLC6A8 | 6535 | X | 24137762 | Mental retardation |
| SLC9A6 | 10479 | X | 25044251 | cognitive disability |
| SMAD3 | 4088 | 15 | 22803640 | Cardiovascular malformations and aneurysms |
| SMAD4 | 4089 | 18 | 18823382 | pancreatic cancer, juvenile polyposis syndrome, and hereditary hemorrhagic telangiectasia syndrome |
| SMARCA4 | 6597 | 19 | 23775540 | Rhabdoid tumor predisposition syndrome |
| SMARCB1 | 6598 | 22 | 28338502 | Rhabdoid tumor predisposition syndrome |
| SMS | 6611 | X | 23696453 | intellectual disability |
| SNURF | 8926 | 15 | 22511895 | Prader-Willi Syndrome |
| SOX11 | 6664 | 2 | 6543203 | Autism and mental retardation |
| SOX5 | 6660 | 12 | 23498568 | Mental retardation |
| SPINK1 | 6690 | 5 | 27159572 | hereditary pancreatitis and tropical calcific pancreatitis |
| SRY | 6736 | Y | 7987333 | gonadal dysgenesis |
| STK11 | 6794 | 19 | 29141581 | Peutz-Jeghers syndrome and cancer |
| STS | 412 | X | 26421812 | X-linked ichthyosis (XLI) |
| STXBP1 | 6812 | 9 | 26865513 | infantile epileptic encephalopathy-4 |
| SYN1 | 6853 |  | 22807112 | neuronal degeneration such as Rett syndrome |
| SYNGAP1 | 8831 | 6 | 23161826 | intellectual disability and autism |
| TAB2 | 23118 | 6 | 25940952 | congenital heart defects |
| TBX20 | 57057 | 7 | 26118961 | cardiac pathologies |
| TBX22 | 50945 | X | 22851992 | Cleft palate |
| TBX4 | 9496 | 17 | 15106123 | Small patella syndrome |
| TCF12 | 6938 | 15 | 26068201 | Anaplastic oligodendroglioma |
| TDGF1 | 6997 | 3 | 12073012 | forebrain defects |
| TFAP2B | 7021 | 6 | 24507797 | Char syndrome |
| TGFBR1 | 7046 | 9 | 21358634 | Ferguson-Smith disease (FSD) |
| TGFBR2 | 7048 | 3 | 28344185 | Syndrome, Loeys-Deitz Aortic Aneurysm Syndrome |
| TGIF1 | 7050 | 18 | 16962354 | holoprosencephaly type 4 |
| TIMM8A | 1678 | X | 20301395 | Jensen syndrome |
| TNNI3 | 7137 | 19 | 18006163 | cardiomyopathy |
| TP63 | 8626 | 3 | 11462173 | ectodermal dysplasia, cleft lip/palate, and split-hand/foot malformation |
| TSPAN7 | 7102 | X | 19339915 | cognitive disability and neuropsychiatric diseases |
| UBE2A | 7319 | X | 16909393 | cognitive disability |
| UBE3A | 7337 | 15 | 28559284 | autism |
| UPF3B | 65109 | X | 22609145 | Mental retardation |
| VEGFA | 7422 | 6 | 20420808 | Cardiovascular defects |
| WDR45 | 11152 | X | 27030146 | neurodegeneration |
| XIAP | 331 | X | 26182687 | dysgammaglobulinemia |
| YAP1 | 10413 | 11 | 24462371 | hearing loss, intellectual disability, hematuria, and orofacial clefting |
| ZC4H2 | 55906 | X | 23623388 | cognitive disability |
| ZDHHC9 | 51114 | X | 28687527 | cognitive disability |
| ZEB2 | 9839 | 2 | 15121779 | Mowat-Wilson syndromw |
| ZFPM2 | 23414 |  | 24769157 | Cardiovascular malformations |
| ZIC1 | 7545 | 3 | 24782033 | Hepatocellular carcinoma |
| ZIC3 | 7547 | X | 24123890 | X-linked visceral heterotaxy |
| ZIC4 | 84107 | 3 | 21204220 | Danny-Walker malformation |
| ZNF41 | 7592 | X | 14628291 | cognitive disability |
| ZNF674 | 641339 | X | 22126752 | cognitive disability |
| ZNF711 | 7552 | X | 21384559 | cognitive disability |
| CACNA1A | 773 | 19 |  | Neurological disorders |

Compositions

Episomal Vectors

Described herein are compositions useful as components for targeting transcriptional activation domains to genetic control elements to increase transcription of an endogenous gene and thereby treat a disease or condition associated with, exacerbated by, or caused by reduced transcription of a gene, reduced amount of a gene product, or reduced activity of a gene product. The components include guide RNAs, scaffold RNAs, scaffold RNA ligands, CRISPR nucleases, transcriptional activation domains, affinity tag(s), affinity tag ligand(s), fusion proteins of one or more thereof, and combinations thereof. The components also include episomal vectors that encode one or more guide RNAs, scaffold RNAs, scaffold RNA ligands, CRISPR nucleases, transcriptional activation domains, affinity tag(s), affinity tag ligand(s), fusion proteins of one or more thereof, and combinations thereof. The episomal vectors can be single- or double-stranded DNA, single-stranded RNA, or double-stranded RNA.

In one embodiment, an episomal vector encoding a CRISPR nuclease, such as a catalytically inactive CRISPR nuclease is be provided. In some cases, the episomal vector encodes a CRISPR nuclease fused to one or more transcriptional activation domains. In some cases, the episomal vector encodes a CRISPR nuclease fused to one or more affinity tags. In some cases, the episomal vector encodes a CRISPR nuclease fused to one or more affinity tags and one or more transcriptional activation domains. CRISPR nuclease fusion proteins can contain transcriptional activator domain(s) and/or affinity tag(s) fused at the amino-terminus of the CRISPR nuclease, at the carboxy terminus, or a combination thereof. Additionally or alternatively, the CRISPR nuclease can be modified by the insertion of transcriptional activator domain(s) and/or affinity tag(s) within a surface loop. The episomal vector (e.g., AAV vector) can contain a promoter that is operably linked to the CRISPR nuclease or CRISPR nuclease fusion protein. The promoter can be a promoter that is endogenous to a viral source from which the episomal vector is derived. For example, where the episomal vector is an AAV vector, the promoter can be an endogenous AAV promoter. Alternatively, the promoter can be a promoter that is heterologous to the viral source form which the episomal vector is derived. For example, where the episomal vector is an AAV vector, the promoter can be a non-AAV promoter. The promoter can be a promoter of a gene targeted for transcriptional activation (e.g., a gene selected from Table 1) or a promoter that is heterologous to the targeted gene. The promoter can be constitutive (e.g., a CMV promoter, CAG promoter, CBA promoter, EF1a promoter, PGK promoter, etc.), tissue specific (e.g., a synapsin, camKIIa, GFAP, RPE, ALB, TBG, MBP, MCK, TNT, or aMHC, promoter, and the like), or inducible (e.g., tetracycline inducible).

In one embodiment, an episomal vector encoding a zinc finger nuclease is provided. In some cases, the episomal vector encodes a zinc finger nuclease fused to one or more transcriptional activation domains. In some cases, the episomal vector encodes a zinc finger nuclease fused to one or more affinity tags. In some cases, the episomal vector encodes a zinc finger nuclease fused to one or more affinity tags and one or more transcriptional activation domains. Zinc finger nuclease fusion proteins can contain transcriptional activator domain(s) and/or affinity tag(s) fused at the amino-terminus of the zinc finger nuclease, at the carboxy terminus, or a combination thereof. The episomal vector (e.g., AAV vector) can contain a promoter that is operably linked to the zinc finger nuclease or zinc finger nuclease fusion protein. The promoter can be a promoter that is endogenous to a viral source from which the episomal vector is derived. For example, where the episomal vector is an AAV vector, the promoter can be an endogenous AAV promoter. Alternatively, the promoter can be a promoter that is heterologous to the viral source form which the episomal vector is derived. For example, where the episomal vector is an AAV vector, the promoter can be a non-AAV promoter. The promoter can be a promoter of a gene targeted for transcriptional activation (e.g., a gene selected from Table 1) or a promoter that is heterologous to the targeted gene. The promoter can be constitutive (e.g., a CMV promoter, CAG promoter, CBA promoter, EF1a promoter, PGK promoter, etc.), tissue specific (e.g., a synapsin, camKIIa, GFAP, RPE, ALB, TBG, MBP, MCK, TNT, or aMHC, promoter, and the like), or inducible (e.g., tetracycline inducible).

In one embodiment, an episomal vector encoding a TALEN is provided. In some cases, the episomal vector encodes a TALEN fused to one or more transcriptional activation domains. In some cases, the episomal vector encodes a TALEN fused to one or more affinity tags. In some cases, the episomal vector encodes a TALEN fused to one or more affinity tags and one or more transcriptional activation domains. TALENs can contain transcriptional activator domain(s) and/or affinity tag(s) fused at the amino-terminus, at the carboxy terminus, or a combination thereof. The episomal vector (e.g., AAV vector) can contain a promoter that is operably linked to the TALEN. The promoter can be a promoter that is endogenous to a viral source from which the episomal vector is derived. For example, where the episomal vector is an AAV vector, the promoter can be an endogenous AAV promoter. Alternatively, the promoter can be a promoter that is heterologous to the viral source form which the episomal vector is derived. For example, where the episomal vector is an AAV vector, the promoter can be a non-AAV promoter. The promoter can be a promoter of a gene targeted for transcriptional activation (e.g., a gene selected from Table 1) or a promoter that is heterologous to the targeted gene. The promoter can be constitutive (e.g., a CMV promoter, CAG promoter, CBA promoter, EF1a promoter, PGK promoter, etc.), tissue specific (e.g., a synapsin, camKIIa, GFAP, RPE, ALB, TBG, MBP, MCK, TNT, or aMHC, promoter, and the like), or inducible (e.g., tetracycline inducible).

In one embodiment, an episomal vector encoding a guide RNA is provided. The guide RNA can be a small guide RNA. The guide RNA can be a component of a synergistic activation mediator (e.g., as described in Zhang et al., Scientific Reports 5, Article No. 16277 (2015); and Konermann et al., 2015, Nature 517:583-8). The episomal vector (e.g., AAV vector) can contain a promoter that is operably linked to the guide RNA. The promoter can be a promoter that is endogenous to a viral source from which the episomal vector is derived. For example, where the episomal vector is an AAV vector, the promoter can be an endogenous AAV promoter. Alternatively, the promoter can be a promoter that is heterologous to the viral source form which the episomal vector is derived. For example, where the episomal vector is an AAV vector, the promoter can be a non-AAV promoter. The promoter can be a promoter of a gene targeted for transcriptional activation (e.g., a gene selected from Table 1) or a promoter that is heterologous to the targeted gene. The promoter can be constitutive (e.g., a CMV promoter, CAG promoter, CBA promoter, EF1a promoter, PGK promoter, etc.), tissue specific (e.g., a synapsin, camKIIa, GFAP, RPE, ALB, TBG, MBP, MCK, TNT, or aMHC, promoter, and the like), or inducible (e.g., tetracycline inducible).

In some embodiments, the episomal vector encodes both a CRISPR nuclease and a guide RNA. In some cases, the CRISPR nuclease is operably linked to a promoter and the guide RNA is operably linked to a different promoter. In some cases, the two promoters are the same. In some cases, the two promoters are different. In some cases, both promoters are inducible. In some cases, both promoters are tissue specific. In some cases, both promoters are constitutive. In some cases, one promoter is constitutive and the other promoter is tissue specific. In some cases, one promoter is constitutive and the other promoter is inducible. In some cases, one promoter is tissue specific and the other is inducible.

In some embodiments, the episomal vector encodes a scaffold RNA, such as a scaffold RNA described in WO 2016/054106. In some embodiments, the episomal vector also encodes a CRISPR nuclease. Additionally or alternatively, the episomal vector can also encode one or more transcriptional activation domain(s). In some cases, the transcriptional activation domain(s) are fused to a binding element that binds to the scaffold RNA (e.g., binds to an ms2, f6, PP7, com, or L7a sequence of a scaffold RNA).

In some embodiments, two or more different episomal vector are provided. For example, an episomal vector encoding a CRISPR nuclease and a separate episomal vector encoding a guide RNA can be provided. Alternatively, an episomal vector encoding a CRISPR nuclease and a guide RNA can be provided and a separate episomal vector encoding one or more transcriptional activation domain(s) can be provided. In some cases, the one or more transcriptional activation domains are fused to a binding element that binds a scaffold RNA (e.g., binds a guide RNA of an SAM). In some cases, the one or more transcriptional activation domains are fused to a binding element that binds an affinity tag of a CRISPR nuclease. In some embodiments, an episomal vector encoding a scaffold RNA is provided and a separate episomal vector is provided that encodes one or more transcriptional activation domain(s) fused to a binding element that binds the scaffold RNA.

In some embodiments, the episomal vector encodes a zinc finger nuclease or TALEN that hybridizes to or specifically hybridizes to (e.g., under stringent hybridization conditions) a gene listed in Table 1, or a gene in the same pathway or a parallel pathway as a gene listed in Table 1. In some cases, the episomal vector encodes a zinc finger nuclease or TALEN that hybridizes to or specifically hybridizes to (e.g., under stringent hybridization conditions) a control region (e.g., promoter region or enhancer region) of a gene listed in Table 1, or a gene in the same pathway or a parallel pathway as a gene listed in Table 1.

In some cases, the episomal vector encodes a zinc finger nuclease or TALEN that hybridizes to or specifically hybridizes to (e.g., under stringent hybridization conditions) to SIM1, Leptin, Leptin receptor, MC4R, SCN2A, SETD5, PAX6, PKD1, MC3R, POMC, STAT3, STAT5, SOCS3, GHR, NPY, NPY1R, NPY2R, NPY5R, PYY, AMPK (PRKAA1, PRKAA2, PRKAB1, PRKAB2, PRKAG1, PRKAG2, PRKAG3), OXT, JAK2, SHP2, NOS3, NROB2, BRS3, CARTPT, FABP4, HTR2C, IL6, NHLH2, NMU, NPB, NPBWRI, PNPLA2, UCP3, ADIPOQ, APOA5, ARNT2, ASIP, CIQTNF2, C3AR1, CCK, CPT1B, CSF2, DGAT1, DGAT2, GHRL, GHSR, HSD11B1, HTR7, INSIG1, INSIG2, LIPC, NMUR1, NMUR2, NPBWR2, NTS, PPARGC1A, PPY, RETN, SIRT1, TGFBR2, WDTC1, or FOXO1. In some cases, the episomal vector encodes a zinc finger nuclease or TALEN that hybridizes to or specifically hybridizes to (e.g., under stringent hybridization conditions) a control region (e.g., promoter region or enhancer region) of SIM1, Leptin, Leptin receptor, MC4R, SCN2A, SETD5, PAX6, PKD1, MC3R, POMC, STAT3, STAT5, SOCS3, GHR, NPY, NPY1R, NPY2R, NPY5R, PYY, AMPK (PRKAA1, PRKAA2, PRKAB1, PRKAB2, PRKAG1, PRKAG2, PRKAG3), OXT, JAK2, SHP2, NOS3, NROB2, BRS3, CARTPT, FABP4, HTR2C, IL6, NHLH2, NMU, NPB, NPBWRI, PNPLA2, UCP3, ADIPOQ, APOA5, ARNT2, ASIP, CIQTNF2, C3AR1, CCK, CPT1B, CSF2, DGAT1, DGAT2, GHRL, GHSR, HSD11B1, HTR7, INSIG1, INSIG2, LIPC, NMUR1, NMUR2, NPBWR2, NTS, PPARGC1A, PPY, RETN, SIRT1, TGFBR2, WDTC1, or FOXO1.

In some cases, the episomal vector encodes a zinc finger nuclease or TALEN that hybridizes to or specifically hybridizes to (e.g., under stringent hybridization conditions) a control region (e.g., promoter region or enhancer region) of SIM1. In some cases, the episomal vector encodes a zinc finger nuclease or TALEN that hybridizes to or specifically hybridizes to (e.g., under stringent hybridization conditions) a promoter region of SIM1. In some cases, the episomal vector encodes a zinc finger nuclease or TALEN that hybridizes to or specifically hybridizes to (e.g., under stringent hybridization conditions) an enhancer region of SIM1. In some cases, the episomal vector encodes a zinc finger nuclease or TALEN that hybridizes to or specifically hybridizes to (e.g., under stringent hybridization conditions) a control region (e.g., promoter region or enhancer region) of MC4R. In some cases, the episomal vector encodes a zinc finger nuclease or TALEN that hybridizes to or specifically hybridizes to (e.g., under stringent hybridization conditions) a promoter region of MC4R. In some cases, the episomal vector encodes a zinc finger nuclease or TALEN that hybridizes to or specifically hybridizes to (e.g., under stringent hybridization conditions) an enhancer region of MC4R. In some cases, the episomal vector encodes a zinc finger nuclease or TALEN that hybridizes to or specifically hybridizes to (e.g., under stringent hybridization conditions) a control region (e.g., promoter region or enhancer region) of PDK1. In some cases, the episomal vector encodes a zinc finger nuclease or TALEN that hybridizes to or specifically hybridizes to (e.g., under stringent hybridization conditions) a promoter region of PDK1. In some cases, the episomal vector encodes a zinc finger nuclease or TALEN that hybridizes to or specifically hybridizes to (e.g., under stringent hybridization conditions) an enhancer region of PDK1. In some cases, the episomal vector encodes a zinc finger nuclease or TALEN that hybridizes to or specifically hybridizes to (e.g., under stringent hybridization conditions) a control region (e.g., promoter region or enhancer region) of SETD5. In some cases, the episomal vector encodes a zinc finger nuclease or TALEN that hybridizes to or specifically hybridizes to (e.g., under stringent hybridization conditions) a promoter region of SETD5. In some cases, the episomal vector encodes a zinc finger nuclease or TALEN that hybridizes to or specifically hybridizes to (e.g., under stringent hybridization conditions) an enhancer region of SETD5. In some cases, the episomal vector encodes a zinc finger nuclease or TALEN that hybridizes to or specifically hybridizes to (e.g., under stringent hybridization conditions) a control region (e.g., promoter region or enhancer region) of SCN2A. In some cases, the episomal vector encodes a zinc finger nuclease or TALEN that hybridizes to or specifically hybridizes to (e.g., under stringent hybridization conditions) a promoter region of SCN2A. In some cases, the episomal vector encodes a zinc finger nuclease or TALEN that hybridizes to or specifically hybridizes to (e.g., under stringent hybridization conditions) an enhancer region of SCN2A. In some cases, the episomal vector encodes a zinc finger nuclease or TALEN that hybridizes to or specifically hybridizes to (e.g., under stringent hybridization conditions) a control region (e.g., promoter region or enhancer region) of PAX6. In some cases, the episomal vector encodes a zinc finger nuclease or TALEN that hybridizes to or specifically hybridizes to (e.g., under stringent hybridization conditions) a promoter region of PAX6. In some cases, the episomal vector encodes a zinc finger nuclease or TALEN that hybridizes to or specifically hybridizes to (e.g., under stringent hybridization conditions) an enhancer region of PAX6.

In some embodiments, the episomal vector encodes a guide or scaffold RNA that hybridizes to or specifically hybridizes to (e.g., under stringent hybridization conditions) a gene listed in Table 1, or a gene in the same pathway or a parallel pathway as a gene listed in Table 1. In some cases, the episomal vector encodes a guide or scaffold RNA that hybridizes to or specifically hybridizes to (e.g., under stringent hybridization conditions) a control region (e.g., promoter region or enhancer region) of a gene listed in Table 1, or a gene in the same pathway or a parallel pathway as a gene listed in Table 1.

In some cases, the episomal vector encodes a guide or scaffold RNA that hybridizes to or specifically hybridizes to (e.g., under stringent hybridization conditions) to SIM1, Leptin, Leptin receptor, MC4R, SCN2A, SETD5, PAX6, PKD1, MC3R, POMC, STAT3, STAT5, SOCS3, GHR, NPY, NPY1R, NPY2R, NPY5R, PYY, AMPK (PRKAA1, PRKAA2, PRKAB1, PRKAB2, PRKAG1, PRKAG2, PRKAG3), OXT, JAK2, SHP2, NOS3, NROB2, BRS3, CARTPT, FABP4, HTR2C, IL6, NHLH2, NMU, NPB, NPBWRI, PNPLA2, UCP3, ADIPOQ, APOA5, ARNT2, ASIP, CIQTNF2, C3AR1, CCK, CPT1B, CSF2, DGAT1, DGAT2, GHRL, GHSR, HSD11B1, HTR7, INSIG1, INSIG2, LIPC, NMUR1, NMUR2, NPBWR2, NTS, PPARGC1A, PPY, RETN, SIRT1, TGFBR2, WDTC1, or FOXO1.

In some cases, the episomal vector encodes a guide or scaffold RNA that hybridizes to or specifically hybridizes to (e.g., under stringent hybridization conditions) a control region (e.g., promoter region or enhancer region) of SIM1, Leptin, Leptin receptor, MC4R, SCN2A, SETD5, PAX6, PKD1, MC3R, POMC, STAT3, STAT5, SOCS3, GHR, NPY, NPY1R, NPY2R, NPY5R, PYY, AMPK (PRKAA1, PRKAA2, PRKAB1, PRKAB2, PRKAG1, PRKAG2, PRKAG3), OXT, JAK2, SHP2, NOS3, NROB2, BRS3, CARTPT, FABP4, HTR2C, IL6, NHLH2, NMU, NPB, NPBWRI, PNPLA2, UCP3, ADIPOQ, APOA5, ARNT2, ASIP, CIQTNF2, C3AR1, CCK, CPT1B, CSF2, DGAT1, DGAT2, GHRL, GHSR, HSD11B1, HTR7, INSIG1, INSIG2, LIPC, NMUR1, NMUR2, NPBWR2, NTS, PPARGC1A, PPY, RETN, SIRT1, TGFBR2, WDTC1, or FOXO1.

In some cases, the episomal vector encodes a guide or scaffold RNA that hybridizes to or specifically hybridizes to (e.g., under stringent hybridization conditions) a control region (e.g., promoter region or enhancer region) of SIM1. In some cases, the episomal vector encodes a guide or scaffold RNA that hybridizes to or specifically hybridizes to (e.g., under stringent hybridization conditions) a promoter region of SIM1. In some cases, the episomal vector encodes a guide or scaffold RNA that hybridizes to or specifically hybridizes to (e.g., under stringent hybridization conditions) an enhancer region of SIM1. In some cases, the episomal vector encodes a guide or scaffold RNA that hybridizes to or specifically hybridizes to (e.g., under stringent hybridization conditions) a control region (e.g., promoter region or enhancer region) of MC4R. In some cases, the episomal vector encodes a guide or scaffold RNA that hybridizes to or specifically hybridizes to (e.g., under stringent hybridization conditions) a promoter region of MC4R. In some cases, the episomal vector encodes a guide or scaffold RNA that hybridizes to or specifically hybridizes to (e.g., under stringent hybridization conditions) an enhancer region of MC4R. In some cases, the episomal vector encodes a guide or scaffold RNA that hybridizes to or specifically hybridizes to (e.g., under stringent hybridization conditions) a control region (e.g., promoter region or enhancer region) of PDK1. In some cases, the episomal vector encodes a guide or scaffold RNA that hybridizes to or specifically hybridizes to (e.g., under stringent hybridization conditions) a promoter region of PDK1. In some cases, the episomal vector encodes a guide or scaffold RNA that hybridizes to or specifically hybridizes to (e.g., under stringent hybridization conditions) an enhancer region of PDK1. In some cases, the episomal vector encodes a guide or scaffold RNA that hybridizes to or specifically hybridizes to (e.g., under stringent hybridization conditions) a control region (e.g., promoter region or enhancer region) of SETD5. In some cases, the episomal vector encodes a guide or scaffold RNA that hybridizes to or specifically hybridizes to (e.g., under stringent hybridization conditions) a promoter region of SETD5. In some cases, the episomal vector encodes a guide or scaffold RNA that hybridizes to or specifically hybridizes to (e.g., under stringent hybridization conditions) an enhancer region of SETD5. In some cases, the episomal vector encodes a guide or scaffold RNA that hybridizes to or specifically hybridizes to (e.g., under stringent hybridization conditions) a control region (e.g., promoter region or enhancer region) of SCN2A. In some cases, the episomal vector encodes a guide or scaffold RNA that hybridizes to or specifically hybridizes to (e.g., under stringent hybridization conditions) a promoter region of SCN2A. In some cases, the episomal vector encodes a guide or scaffold RNA that hybridizes to or specifically hybridizes to (e.g., under stringent hybridization conditions) an enhancer region of SCN2A. In some cases, the episomal vector encodes a guide or scaffold RNA that hybridizes to or specifically hybridizes to (e.g., under stringent hybridization conditions) a control region (e.g., promoter region or enhancer region) of PAX6. In some cases, the episomal vector encodes a guide or scaffold RNA that hybridizes to or specifically hybridizes to (e.g., under stringent hybridization conditions) a promoter region of PAX6. In some cases, the episomal vector encodes a guide or scaffold RNA that hybridizes to or specifically hybridizes to (e.g., under stringent hybridization conditions) an enhancer region of PAX6.

In some cases, the targeting region of the guide RNA is encoded by, specifically hybridizes to, or is fully complementary to: SEQ ID NO:1 (GACACGGAATTCATTGCCAG), SEQ ID NO:2 (CTGCGGGTTAGGTCTACCGG), SEQ ID NO:3 (GTTGAGCGCTCAGTCCAGCG), SEQ ID NO:4 (TCCCGACGTCGTGCGCGACC), or SEQ ID NO:5 (GCTCTGAATCTTACTACCCG). In some cases, the targeting region of the guide RNA is encoded by, specifically hybridizes to, or is fully complementary to: SEQ ID NO:6 (GCTGTTAACTAAAGACAGGG), SEQ ID NO:7 (GTGGTCTGGGTGATCTCATG), SEQ ID NO:8 (GACAAAGGAACATCTGAGAGG), SEQ ID NO:9 (GTGATCTCATGGGGAAGAGG), or SEQ ID NO:10 (GGCTTTGATCGTGGTCTGGG). In some cases, the targeting region of the guide RNA is encoded by, specifically hybridizes to, or is fully complementary to: SEQ ID NO:11 (GCGAGCCCAGTCGCGTGGGG), SEQ ID NO:12 (GCCAAGAATTGGCCAAAGGG), SEQ ID NO:34 (GTCAAAGGGGCATATGGAAGG), SEQ ID NO:35 (GGGAAGAAAGCCCCACTTGG), SEQ ID NO:36 (GCCCAGTCGCGTGGGGGGGG), or SEQ ID NO:37 (GGAGCGCGAGTGTCACTCGG). In another embodiment, the targeting region of the guide RNA is encoded by, specifically hybridizes to, or is fully complementary to: SEQ ID NO:38 (GCTCACTGTAGGACCCGAGCC), SEQ ID NO:39 (GACGCGGCGCTCATTGGCCAA), SEQ ID NO:40 (CGAGCCGCGAGCCCAGTCGCG), SEQ ID NO:41 (TCCCCCCCCCCCCCCACGCGA), SEQ ID NO:42 (GTCACTCACCCCGATTGGCCA), or SEQ ID NO:43 (CGCGAGCCCAGTCGCGTGGGG). In some embodiments, the targeting region of the guide RNA is encoded by, specifically hybridizes to, or is fully complementary to: SEQ ID NO:44 (GTTGGCTTATCCAAACATCTC), SEQ ID NO:45 (ATGTTAAGCAAGGGTAATAGA), SEQ ID NO:46 (CTGTGAAAGGAATACAATTCA), SEQ ID NO: 47 (GCCAATTCTTGGCAACCAGAGC), SEQ ID NO:48 (GAATTGGCCAAAGGGAGGGGT), or SEQ ID NO:49 (AATTAGCAGACAGCTTGGTAC). In some embodiments, the targeting region of the guide RNA is encoded by, specifically hybridizes to, or is fully complementary to: SEQ ID NO:50 (CTGGCTGATTCCCGAGGATTT), SEQ ID NO:51 (CACTGAATACGGATTGGTCAG), SEQ ID NO:52 (GATGTCTCAGAACCACTGAAT), SEQ ID NO:53 (AACCACTGAATACGGATTGGT), or SEQ ID NO:54 (ACCAATCCGTATTCAGTGGTT). In some embodiments, the targeting region of the guide RNA is encoded by, specifically hybridizes to, or is fully complementary to: SEQ ID NO:55 (GGCGCGGGGCGGACGGGGCGA), SEQ ID NO:56 (GCGCCCCGGGAACGCGTGGGG), SEQ ID NO:57 (CGCCCCGCGCCGCGCGGGGAG), SEQ ID NO:58 (TCCGCCCCGCGCCGCGCGGGG), SEQ ID NO:59 (GGAACGCGTGGGGCGGAGCTT), SEQ ID NO:60 (GCCCCGCGCCGCGCGGGGAGG), SEQ ID NO:61 (TGCGCCCCGGGAACGCGTGGG), SEQ ID NO:62 (GAACGCGTGGGGCGGAGCTTC), SEQ ID NO:63 (GCGGCGCGGGGCGGACGGGGC), or SEQ ID NO:64 (CCCGTCCGCCCCGCGCCGCGC). In some embodiments, the targeting region of the guide RNA is encoded by, specifically hybridizes to, or is fully complementary to: SEQ ID NO:65 (GGCCCACTCGCCGCCAATCAG), SEQ ID NO:66 (GGAAGCCGCCGGGGCCGCCTA), SEQ ID NO:67 (TGATTGGCGGCGAGTGGGCCA), SEQ ID NO:68: (GCCGCCAATCAGCGGAAGCCG), SEQ ID NO:69: (GGCGGCTTCCGCTGATTGGCG), SEQ ID NO:70: (CCGCCAATCAGCGGAAGCCGC), SEQ ID NO:71: (AGCCGCCGGGGCCGCCTAGAG), SEQ ID NO:72: (GCTTCCGCTGATTGGCGGCGA), SEQ ID NO:73: (CGGCGAGTGGGCCAATGGGTG), or SEQ ID NO:74: (CCAATGGGTGCGGGGCGGTGG). In some embodiments, the targeting region of the guide RNA is encoded by or specifically hybridizes to: SEQ ID NO:75 (GGCTGCCGGGGCCGCCTAAAG), SEQ ID NO:76 (GGAGGCTGCCGGGGCCGCCTA), SEQ ID NO:77 (GCCGCCAATCAGCGGAGGCTG), SEQ ID NO:78 (CCGCCAATCAGCGGAGGCTGC), SEQ ID NO:79 (TGGCCGGTGCGCCGCCAATCA), SEQ ID NO:80 (GGCCGGTGCGCCGCCAATCAG), SEQ ID NO:81 (CGGCGCACCGGCCAATAAGTG), SEQ ID NO:82 (ATAAGTGTGGGGCGGTGGGCG), SEQ ID NO:83 (CCAATAAGTGTGGGGCGGTGG), or SEQ ID NO:84 (CAATAAGTGTGGGGCGGTGGG). In some embodiments, the targeting region of the guide RNA is encoded by or specifically hybridizes to: SEQ ID NO:85: CCTTTCTATGACCTAGTCGG, SEQ ID NO:86: CAGAATCAGTAACGCACTGT, SEQ ID NO:87: GAAACCAGGAGAGATAACCC, SEQ ID NO:88: GGACCCCAGATATTCTGGAA, SEQ ID NO:89: TTATTGTTGACTTAACGAAG, SEQ ID NO:90: AAAAAGAAGCAAATAGCTAA, or SEQ ID NO:91: (AGAATCAGTAACGCACTGTA). In some embodiments, the targeting region of the guide RNA is encoded by, specifically hybridizes to, or is fully complementary to: SEQ ID NO:92 (TGTTGGTTTATTGGACCCCAGATATTC), SEQ ID NO:93 (TGTTGGAGAAAATTAACTTAGTGCATA), or SEQ ID NO:94 (TGTTGGTATAACTGCCACTAGAGGGCT). In some embodiments, the targeting region of the guide RNA is encoded by, specifically hybridizes to, or is fully complementary to SEQ ID NO:95 (AGGAGCCGGGACCCACCGG).

In some cases, the targeting region of the guide RNA is encoded by, specifically hybridizes to, or is fully complementary to a sequence that is orthologous and/or homologous to a region of a mouse or human genome corresponding to, or targeted by an sgRNA comprising, one of SEQ ID NOs:1-12, or 34-95. In some cases, the guide RNA is encoded by, specifically hybridizes to, or is fully complementary to a sequence that is 90%, 95%, or 99% identical to, or differs by 1, 2, or 3 nucleotides from, or is 1, 2, or 3 nucleotides longer or shorter at a 5' and/or 3' end than one of SEQ ID NOs:1-12, or 34-95.

One or more of the episomal vectors described herein can be provided as a kit for treatment of a disease in a mammalian subject associated with, exacerbated by, or caused by reduced transcription of a gene, reduced amount of a gene product, or reduced activity of a gene product. For example, an episomal vector encoding a CRISPR nuclease, a zinc finger nuclease, a TALEN, a TAL effector, a guide RNA, a transcriptional activation domain, a scaffold RNA, a scaffold RNA ligand, an affinity tag ligand, fusion proteins of one or more thereof, or a combination thereof, can be provided as a component of a kit containing an episomal vector packaging plasmid, cell line, or helper virus, or a combination thereof.

In some cases, an episomal vector in which the encoded polypeptide(s) and/or RNA(s) are flanked by AAV inverted terminal repeats is provided as a component of a kit containing additional materials for packaging the episomal vector into functional AAV particles. Such additional materials can include one or more plasmids encoding AAV rep and cap genes, one or more plasmids encoding adenovirus helper factors E1A, E1B, E2A, E40RF6 and VA, adenovirus, or a combination thereof. In some cases, the trans-activating elements and/or helper elements for AAV packaging are provided in a stable cell line as a component of the kit.

In some embodiments, the cap gene is an AAV-DJ, AAV1, AAV2, AAV3, AAV4, AAV5, AAV6, AAV7, AAV8, or AAV9 cap gene. In some embodiments, the cap gene is an AAV-DJ, AAV1, AAV2, AAV5, AAV7, AAV8 or AAV9 cap gene. In some embodiments, the cap gene is an AAV2 cap gene. In some embodiments, the cap gene is an AAV-DJ cap gene. In some embodiments, the inverted terminal repeats (ITRs) are AAV1, AAV2, AAV3, AAV4, AAV5, AAV6, AAV7, AAV8, or AAV9 ITRs. In some embodiments, the ITRs are AAV1, AAV2, AAV5, AAV7, AAV8 or AAV9 ITRs. In some embodiments, the ITRs are AAV2 ITRs. In some cases, the capsid protein encoded by the cap gene is the same serotype as the ITRs. For example, the cap gene can be an AAV2 cap gene and the ITRs can be AAV2 ITRs. In some cases, the capsid protein encoded by the cap gene is a different serotype from the serotype of the ITRs. Thus, for example, the cap gene can be an AAV5 cap gene and the ITRs can be AAV2 ITRs. As another example, the cap gene can be an AAV-DJ cap gene and the ITRs can be AAV2 ITRs.

In some cases, the episomal vector can be in a target cell or cell of the target tissue. In some cases, the target cell or cell of a target tissue is a dividing cell. In some cases, the cell is a non-dividing cell. In some cases, the cell is a neuron. In some cases, the cell is a cell of the hypothalamus. In some cases, the target cell or cell of the target tissue is a mammalian cell that contains a genome having at least one functional copy of a target gene, wherein the functional cop(y/ies) in the absence of transcriptional activation by a heterologous complex do not produce enough of a corresponding gene product to produce a wild-type phenotype in an organism. In some cases, the mammalian cell further comprises a scaffold RNA encoded by an episomal vector described herein, a guide RNA encoded by an episomal vector described herein, a CRISPR nuclease encoded by an episomal vector described herein, a SunTag encoded by an one or more episomal vectors described herein, a synergistic activation mediator (SAM) encoded by one or more episomal vectors described herein, a transcriptional activation domain encoded by an episomal vector described herein, an affinity tag ligand encoded by an episomal vector described herein, a fusion of one or more polypeptides described herein encoded by an episomal vector described herein, or a combination thereof.

In some cases, the episomal vector in a target cell or a cell of a target tissue is converted to a circular form, a circular concatemer, or a linear concatemer, e.g., through recombination of repeat elements, such as ITRs. In some cases, the episomal vector in the target cell or the cell of a target tissue is converted from a single-stranded DNA vector into a double-stranded DNA. In some cases, the double-stranded DNA is converted into a circular form, a circular concatemer, or a linear concatemer. In some cases, the episomal vector in the target cell or cell of the target tissue persists as an episomal element providing persistent transgene (e.g., CRISPR nuclease, transcriptional activator, guide RNA, scaffold RNA, etc.) expression. In some cases, the episomal elements is one of the foregoing circular forms, circular concatemers, or linear concatemers.

Viral Particles

One or more of the foregoing episomal vectors can be packaged in a viral particle. For example, the viral particle can contain an episomal vector encoding a CRISPR nuclease, a guide RNA, a scaffold RNA, a transcriptional activator, an affinity tag, an affinity tag ligand, a scaffold RNA ligand, a fusion protein of one or more thereof, or a combination of one or more thereof. The viral particle can be a viral particle that is capable of delivering the episomal vector to a target cell or tissue, such that the episomal vector enter the nucleus of a target cell or a cell of a target tissue and do not, or do not substantially integrate into the genome of the cell.

In some cases, the viral particle delivers the episomal vector to the target cell or cell of the target tissue and the episomal vector is converted to a circular form, a circular concatemer, or a linear concatemer, e.g., through recombination of repeat elements, such as ITRs. In some cases, the episomal vector delivered by the viral particle is converted from a single-stranded DNA vector into a double-stranded DNA. In some cases, the double-stranded DNA is converted into a circular form, a circular concatemer, or a linear concatemer. In some cases, the viral particle delivers an episomal vector to a target cell or cell of the target tissue, and the episomal vector persists as an episomal element providing persistent transgene expression.

The viral particles can be EBV or AAV viral particles. In some cases, the viral particles are AAV viral particles. In some cases, the viral particles are AAV-DJ, AAV1, AAV2, AAV3, AAV4, AAV5, AAV6, AAV7, AAV8, or AAV9 viral particles. In some cases, the viral particles are AAV-DJ, AAV1, AAV2, AAV5, AAV7, AAV8 or AAV9 viral particles. In some cases, the viral particles are AAV2 viral particles. In some cases, the viral particles are AAV-DJ viral particles. The genome packed in the viral particle and encoding the one or more transgenes (the episomal vector) can be an AAV1, AAV2, AAV3, AAV4, AAV5, AAV6, AAV7, AAV8, or AAV9 genome. In some cases, the genome is an AAV1, AAV2, AAV5, AAV7, AAV8 or AAV9 genome. In some cases, the genome is an AAV2 genome. In some cases the genome is the same serotype as the viral particle in which it is packaged. In other cases, the genome and viral particle are of different serotypes. For example, the capsid can be AAV5 serotype and the episomal vector can be AAV2 serotype. As another example, the capsid can be an AAV-DJ serotype and the episomal vector can be an AAV2 serotype.

One or more of the viral particles described herein can be provided as a kit for treatment of a disease in a mammalian subject associated with, exacerbated by, or caused by reduced transcription of a gene, reduced amount of a gene product, or reduced activity of a gene product. For example, an episomal vector encoding a CRISPR nuclease, a guide RNA, a transcriptional activation domain, a scaffold RNA, a scaffold RNA ligand, an affinity tag ligand, fusion proteins of one or more thereof, or a combination thereof, can be packaged into one or more viral particles and provided as a component of a kit containing a suitable pharmaceutical excipient, carrier, diluent, or buffer for delivery to a subject.

In one embodiment, the viral particles are in a suitable pharmaceutical excipient, carrier, diluent, or buffer for delivery to a subject. Such excipients, carriers, diluents, and buffers include any pharmaceutical agent that can be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins Pharmaceutical Dosage Forms and Drug Delivery Systems (1999) H. C. Ansel et al., eds., $7^{th}$ ed., Lippincott, Williams, & Wilkins and Handbook of Pharmaceutical Excipients (2000) A. H. Kibbe et al., eds., $3^{rd}$ ed. Amer. Pharmaceutical Assoc.

Methods

Described herein are methods for treating a disease in a mammalian subject associated with, exacerbated by, or caused by reduced transcription of a gene, reduced amount of a gene product, or reduced activity of a gene product by increasing transcription of a target gene. The methods generally include contacting a target cell or a cell of a target tissue with one or more of the foregoing episomal vectors. In some embodiments, the episomal vectors are non-integrating or substantially non-integrating. In some embodiments, the episomal vectors are packaged into viral particles and the viral particles are contacted with the target cell or the cell of a target tissue. In some cases, the contacting is performed in vivo. In some cases, the contacting is performed in vitro (e.g., using primary cells obtained from the subject) and the contacted cells are delivered to a subject, or optionally cultured and delivered to the subject.

The episomal vectors (e.g., packaged into viral particles) can be delivered by any means known in the art. In some cases, the episomal vectors are contacted with a cell in vivo by systemic delivery (e.g., intravenous delivery). In some cases, the episomal vectors (e.g., packaged into viral particles) are contacted with a cell in vivo by site-specific delivery to an affected cell or tissue. For example, viral particles in which episomal vectors are packaged can be injected into a site of an affected cell or tissue. In some cases, two or more episomal vectors are packaged into viral particles such that each viral particle contains a single copy of one of the two or more episomal vectors or is empty (contains no genome or a genome that lacks a functional transgene). Such viral particles can be delivered as a mixture or individually. In some cases, the particles are delivered simultaneously. In some cases, the particles are delivered sequentially. Typically, the particles are delivered such that the delivered transgenes encoded by the episomal vectors are co-expressed in the subject such that a disease is treated.

In one embodiment, one or more different viral particles (e.g., viral particles having the same capsid but containing vectors that encode different transgenes) are injected into a brain of a subject. In some cases, the one or more viral particles are injected into a hypothalamus of a subject. The viral particles can be delivered to an anterior portion of the hypothalamus, a posterior portion of the hypothalamus, a ventromedial portion of the hypothalamus, or a combination thereof. The viral particles can be delivered bilaterally (e.g., via bilateral injections to a hypothalamus of a subject). In some cases, the one or more viral particles are delivered to a neuron of the subject. In some case, the one or more viral particles are delivered by stereotactic injection.

The dose of viral particle delivered to a subject can be from $1 \times 10^3$ viral particles/kg subject to $1 \times 10^{20}$ viral particles/kg subject. The dose of episomal vector delivered to a subject can be from $1 \times 10^3$ vector molecules/kg subject to $1 \times 10^{20}$ vector molecules/kg subject. In some cases, the dose is from $1 \times 10^4$ to $1 \times 10^{18}$, from $1 \times 10^5$ to $1 \times 10^{16}$, from $1 \times 10^6$ to $1 \times 10^{15}$ viral particles/kg subject or vector molecules/kg subject. In some cases, the dose is at least $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, or $1 \times 10^{15}$ viral particles/kg subject or vector molecules/kg subject. In some cases, vector molecules are in the form of viral genomes delivered in a viral particle. In some cases, the dose is a dose of delivered viral genome (e.g., packaged in a viral particle) encoding a CRISPR nuclease (e.g., dCas9 fused to an activation domain) and a guide RNA (e.g., sgRNA). In some cases, the dose is a dose of delivered viral genome (e.g., packaged in a viral particle) encoding a CRISPR nuclease (e.g., dCas9 fused to an activation domain), and a second dose, such as one or more of the foregoing doses is a dose of delivered viral genome (e.g., packaged in a viral particle) encoding guide RNA (e.g., sgRNA).

In some cases, a systemic does can be higher as compared to a dose applied directly to a tissue or organ to be treated. For example, for treatment of obesity dysregulated by a haploinsufficient sim1 gene in hypothalamus tissue or cell, a lower dose can be delivered to the hypothalamus as compared to a systemic dose. In humans, systemic delivery can, e.g., be about $6.7 \times 10^{13}$–$2.0 \times 10^{14}$ viral genomes (vg)/kg (see, clinicaltrials.gov/ct2/show/NCT02122952) and neurosurgical delivery can, e.g., be about $7.5 \times 10^{11}$–$8.8 \times 10^{12}$ vg/kg (see clinicaltrials.gov/ct2/show/NCT01973543).

A dose can be administered once, or multiple times. In some cases, the dose is delivered at least once within a period of 30 days, 60 days, 90 days, 120 days, or 180 days. In some cases, a dose is delivered at least once every 10 weeks, 20 weeks, 30 weeks, 40 weeks, 52 weeks, or 75 weeks, or 100 weeks. In some cases, a dose is delivered at least once every 6 months, 12 months, 18 months, 2 years, 3 years, 5 years, or 10 years. In some cases, a single dose or 2, or 3, or 4 doses results in persistent and sufficient expression of the otherwise haploinsufficient target gene to treat at least one symptom of a disease or condition caused by the haploinsufficiency for a period of months or years. In some cases, a dose is administered, the sufficiency of expression of a target haploinsufficient gene (e.g., a gene in Table 1 such as sim1) is assessed (e.g., in a target tissue such as hypothalamus) and additional doses are delivered as needed by the same or different route. In some cases, one or more doses of viral particles as described herein are delivered, in sufficient amount to increase transcription of a target gene and thereby treat at least one symptom of a disease associated with, exacerbated by, or caused by reduced transcription of a gene, reduced amount of a gene product, or reduced activity of a gene product, and one or more doses are re-administered when transcription of the target gene has reduced from its maximal expression by at least 10%, 25%, 50%, 75%, 90%, or more.

Examples

Rescue of Haploinsufficiency-Caused Obesity
I. Introduction

Over 300 genes are known to cause human disease due to haploinsufficiency (1, 2), leading to a wide range of phenotypes that include cancer, neurological diseases, developmental disorders, immunological diseases, metabolic disorders, infertility, kidney disease, limb malformations and many others (1). Large-scale exome sequencing analyses estimate that a total of 3,230 human genes could be heterozygous loss-of-function (LoF) intolerant (3). Gene therapy holds great promise in correcting haploinsufficient diseases, by inserting a functional recombinant copy or copies of the mutant gene. Currently, there are a total of 2,300 clinical trials underway for gene therapy, the majority of them using adeno-associated virus (AAV) to deliver the recombinant gene (4). AAV is a preferred gene delivery method due to its ability to deliver DNA without integrating into the genome, not causing pathogenicity and providing long lasting gene expression of the transgene (5). However, AAV has an optimal 4.7 kilo base (kb) packaging capacity, limiting its gene therapy use for genes longer than 3.5 kb (taking into account additional regulatory sequences needed for its stable expression). Analysis of the 3,230 heterozygous LoF genes finds 715 (22%) of them to have coding sequence longer than 3.5 kb, rendering them not suitable for AAV gene therapy.

CRISPR gene editing can potentially fix haploinsufficient mutations, however it would require the need to custom tailor the editing strategy for each mutation. Moreover, it's not a feasible therapy for heterozygous LoF micro-deletions. To address these challenges, we devised a novel therapeutic strategy for haploinsufficiency using CRISPR activation (CRISPRa). CRISPRa takes advantage of the RNA-guided targeting ability of CRISPR to direct a nuclease deficient Cas9 (dCas9) along with a transcriptional activator to regulatory element/s of a specific gene, thus increasing its expression (6-10). Here, we tested whether we can use this system to increase the transcription of the unaffected endogenous gene in a haploinsufficient disease to rescue the disease phenotype.

SIM1 is a transcription factor that is expressed in the developing kidney and central nervous system, and is essential for the formation of the supraoptic (SON) and paraventricular (PVN) nuclei of the hypothalamus (11). It is also thought to play a major role in the leptin pathway (12). In humans, haploinsufficiency of SIM1 due to chromosomal aberrations (12, 13) results in hyperphagic obesity (13) and SIM1 coding mutations, many of them being loss-of-function, are thought to be a major cause of severe obesity in humans (14-16). Sim1 homozygous null mice die perinatally, while Sim1 heterozygous mice ($Sim1^{+/-}$) survive, are hyperphagic and develop early-onset obesity with increased linear growth, hyperinsulinemia and hyperleptinemia (17). A postnatal conditional knockout of hypothalamic Sim1 leads to a similar phenotype in heterozygous mice (18), implicating Sim1 to be an important regulator of energy homeostasis. Overexpression of SIM1, using a human bacterial artificial chromosome in mice, rescues diet-induced obesity and reduced food intake (19), suggesting a potential role for Sim1 as a general therapeutic target for obesity. Here, we used Sim1 as our proof of concept model for our CRISPRa therapeutic strategy. We tested the ability of CRISPRa to rescue the obesity phenotype in $Sim1^{+/-}$ mice using both transgenic and AAV based approaches targeting the Sim1 promoter or its hypothalamus specific enhancer. Our results present a novel therapeutic approach for treating haploinsufficient diseases, or other diseases caused by altered gene dosage.

II. Results

A. Upregulation of Sim1 In Vitro

Figure 1B:
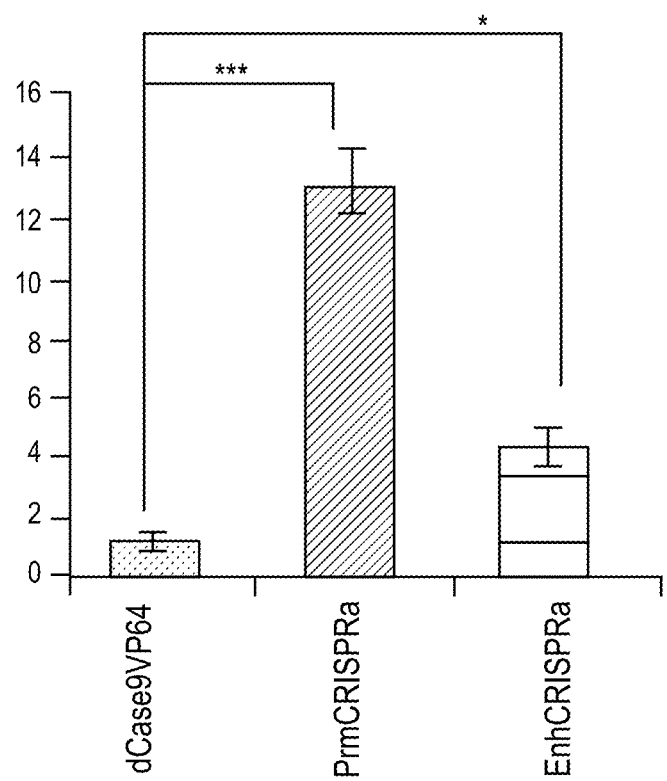
Figure 8A:
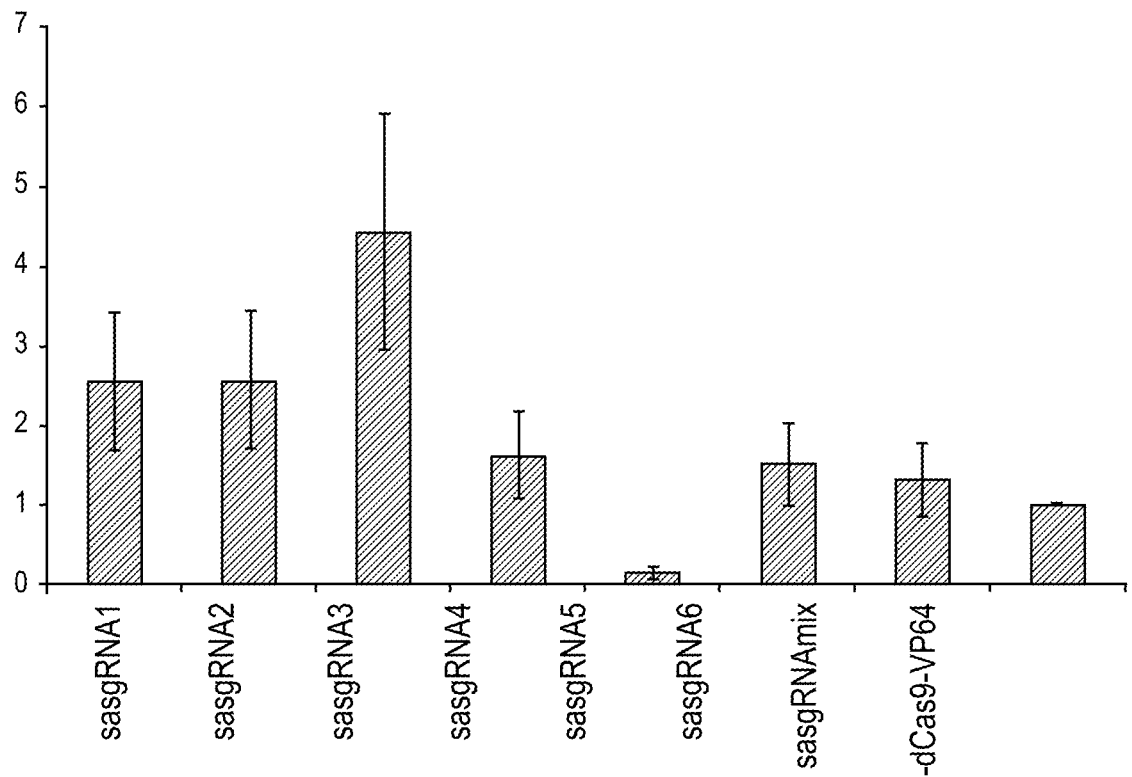
FIG. 8A-8B: CRISPRa Sim1 overexpression in vitro.

We first set out to optimize our CRISPRa conditions in vitro. SIM1 has a well characterized promoter (20) and distant hypothalamus enhancer (~270 kb from the transcription start site), Sim1 candidate enhancer 2 (SCE2 (21)), both of which were chosen as targets for CRISPRa (FIG. 1A). We designed sgRNAs for either the Sim1 promoter or enhancer (SCE2). Using these guides we tested if dCas9 fused to VP64 (dCas9-VP64), a transcriptional activator that carries four tandem copies of VP16 (a herpes simplex virus type 1 transcription factor) (22), can overexpress Sim1 in mouse neuroblastoma cells (Neuro-2a). This activator was chosen due to its lower activation levels compared to other known activators (23), as we wanted to obtain therapeutic Sim1 dosage levels in vivo that are similar to wild-type. Cells were transfected with dCas9-VP64 and the various guides and following 48 hours Sim1 mRNA levels were measured using quantitative PCR (qPCR). We identified one sgRNA for either promoter or SCE2 that was able to overexpress endogenous Sim1 by 13 and 4 fold respectively (FIG. 1B). Additionally, we identified four sgRNAs for the Sim1 promoter that were able to overexpress endogenous Sim1 by over 4-fold (FIG. 7A) and at least one sgRNA for SCE2 that was able to overexpress endogenous Sim1 by over 2-fold (FIG. 8A).

B. Transgenic CRISPRa Rescues Obesity

Figure 1C:
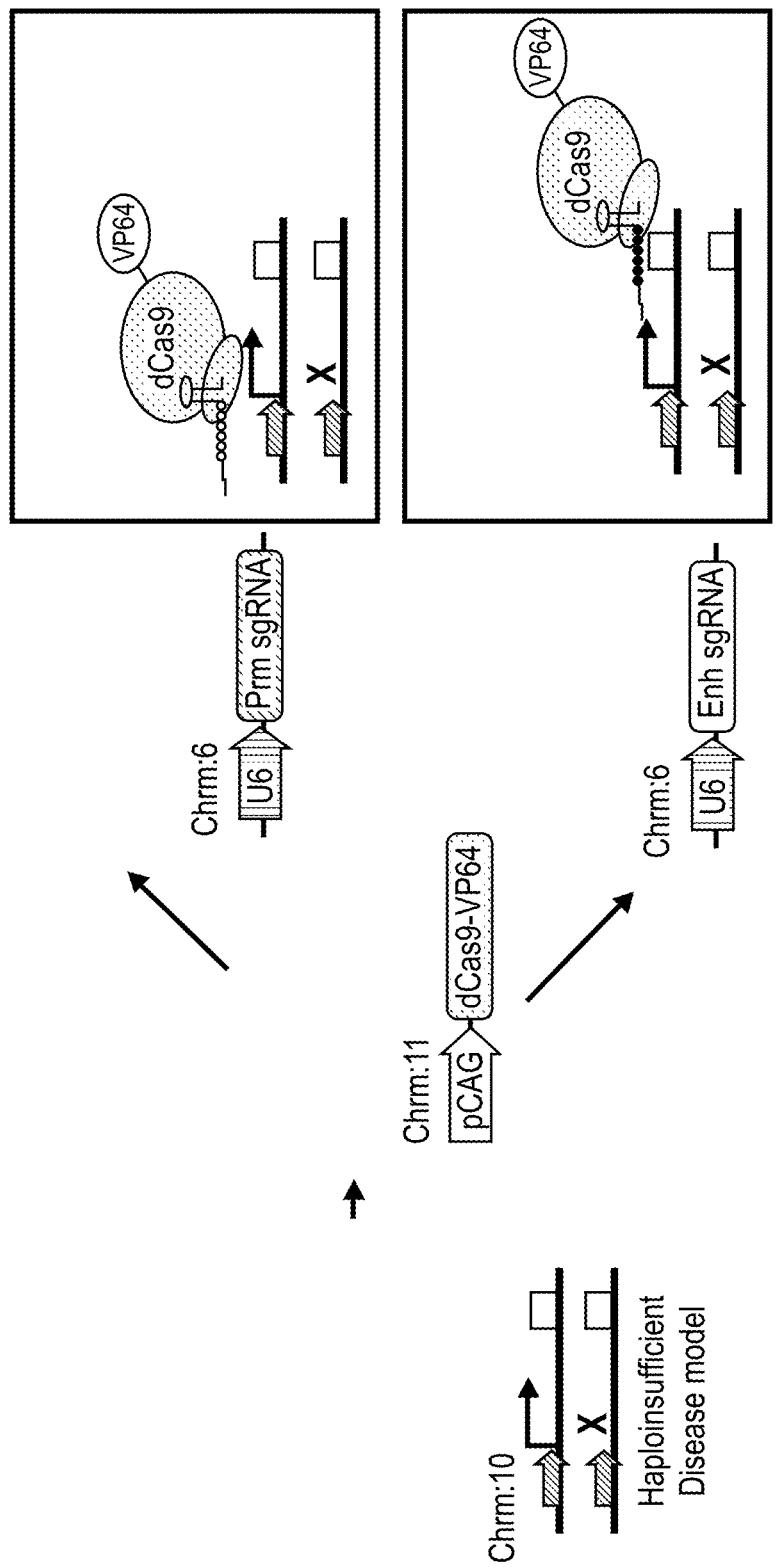
Figure 1D:
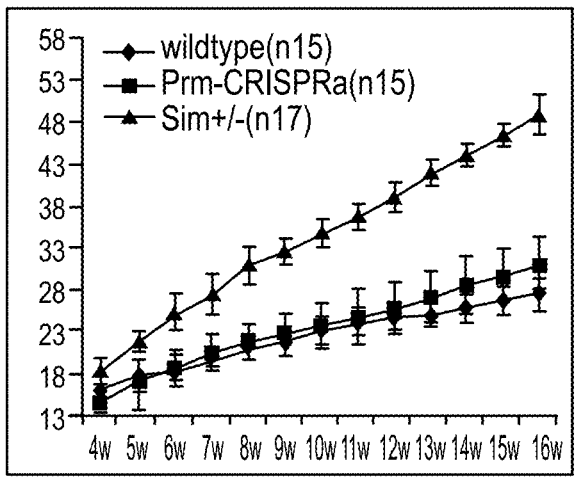
Figure 1D:
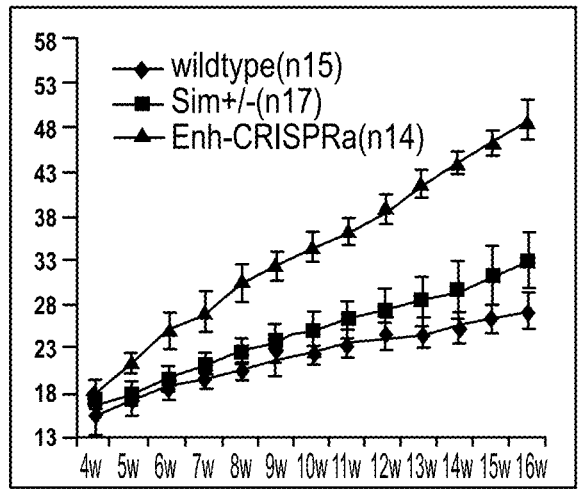
Figure 1D:
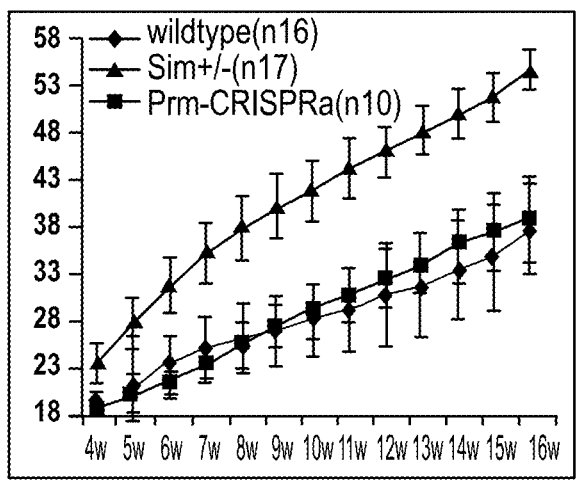
Figure 1D:
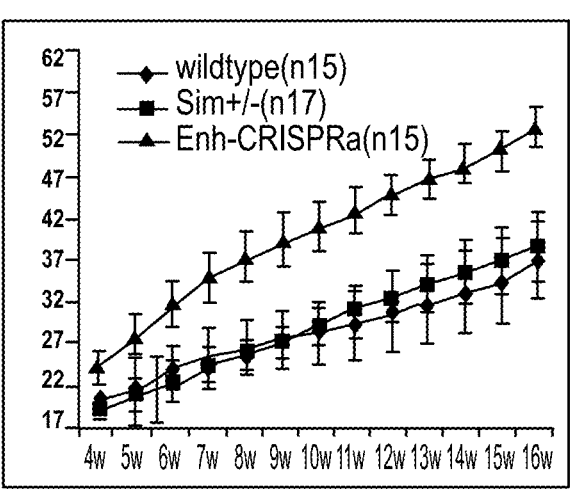
Figure 1E:
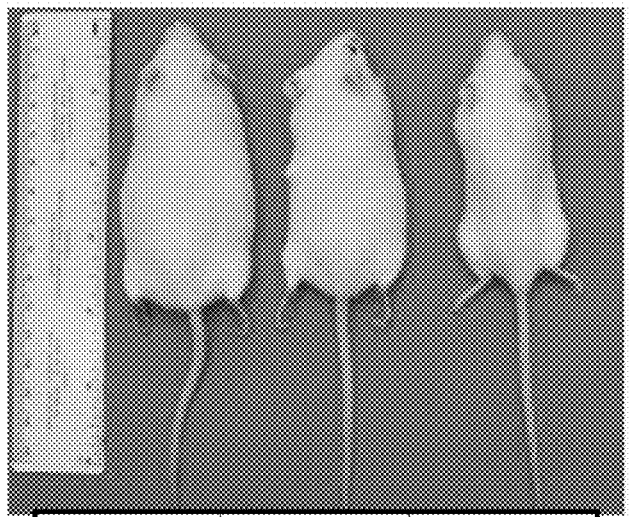
Figure 1F:

To test the ability of our CRISPRa system to activate Sim1 in vivo, we generated knockin mouse lines using TARGATT technology (24) that have dCas9-VP64 inserted into the mouse Hipp11 ($H11P^{CAG-dCas9-VP64}$) locus and either sgRNA, targeting the Sim1 promoter ($ROSA26^{Sim1Pr-sgRNA}$) or SCE2 ($ROSA26^{SCE2En-sgRNA}$), in the Rosa26 locus (FIG. 1C). We then crossed these mice to $Sim1^{+/-}$ mice that develop severe obesity (17). Mice having all three alleles ($Sim1^{+/-} \times H11P^{CAG-dCas9-VP64}$ and $ROSA26^{Sim1Pr-sgRNA}$ or $ROSA26^{SCE2En-sgRNA}$) were maintained using breeders chow (picodiet-5058) and weighed on a weekly basis until 16 weeks of age along with wild-type littermates and $Sim1^{+/-} \times H11P^{CAG-dCas9-VP64}$ mice and $Sim1^{+/-}$, both of which become severely obese (negative controls). Analysis of at least seven females and seven males per condition showed that $Sim1^{+/-}$ mice carrying both dCas9-VP64 and either Sim1 promoter or enhancer sgRNA have a significant reduction in body weight compared to $Sim1^{+/-} \times H11P^{CAG-dCas9-VP64}$ and $Sim1^{+/-}$ littermates (FIGS. 1D-1F).

C. CRISPRa Corrects $Sim1^{+/-}$ Metabolic Profile

Figure 2A:
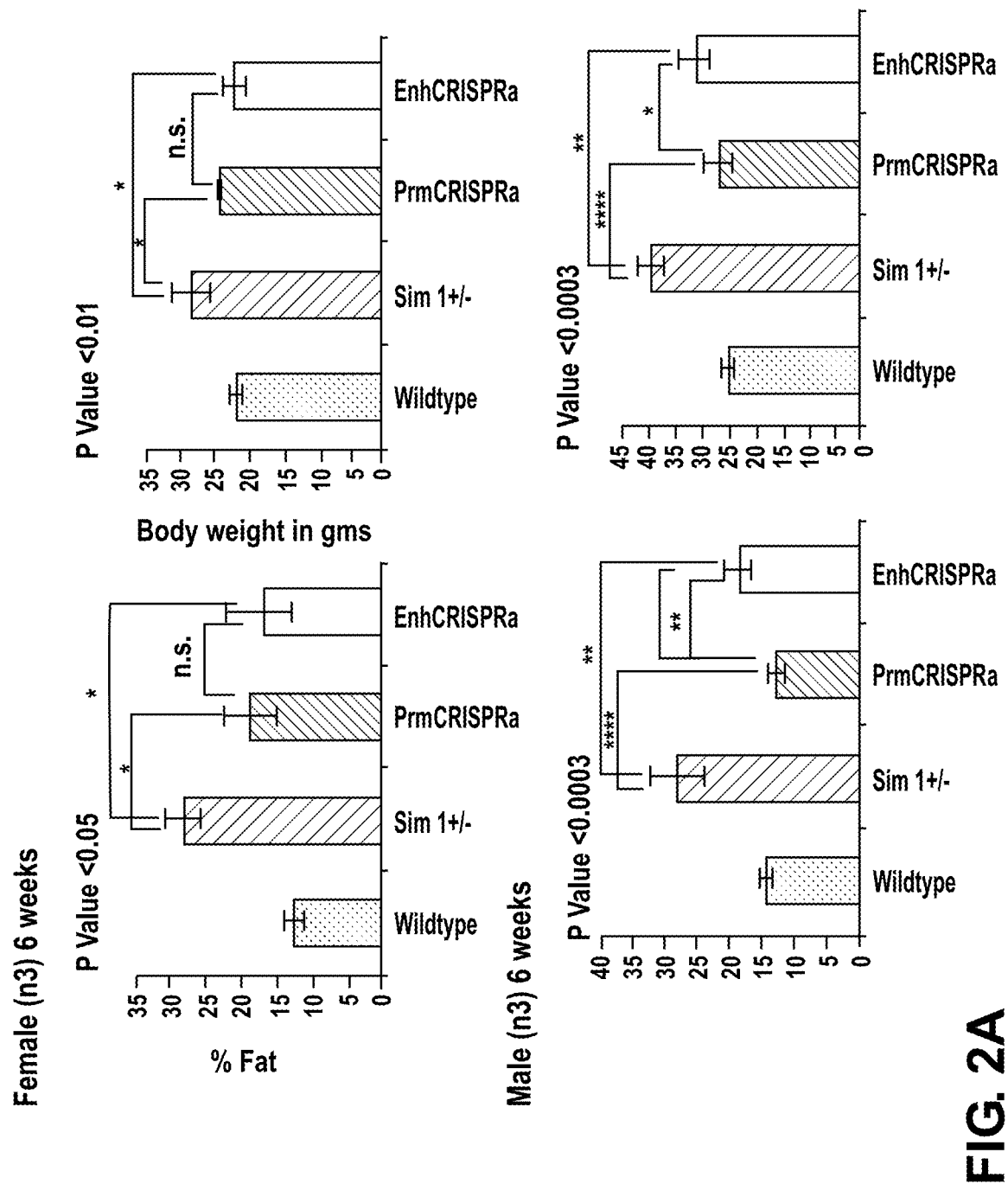
Figure 2B:
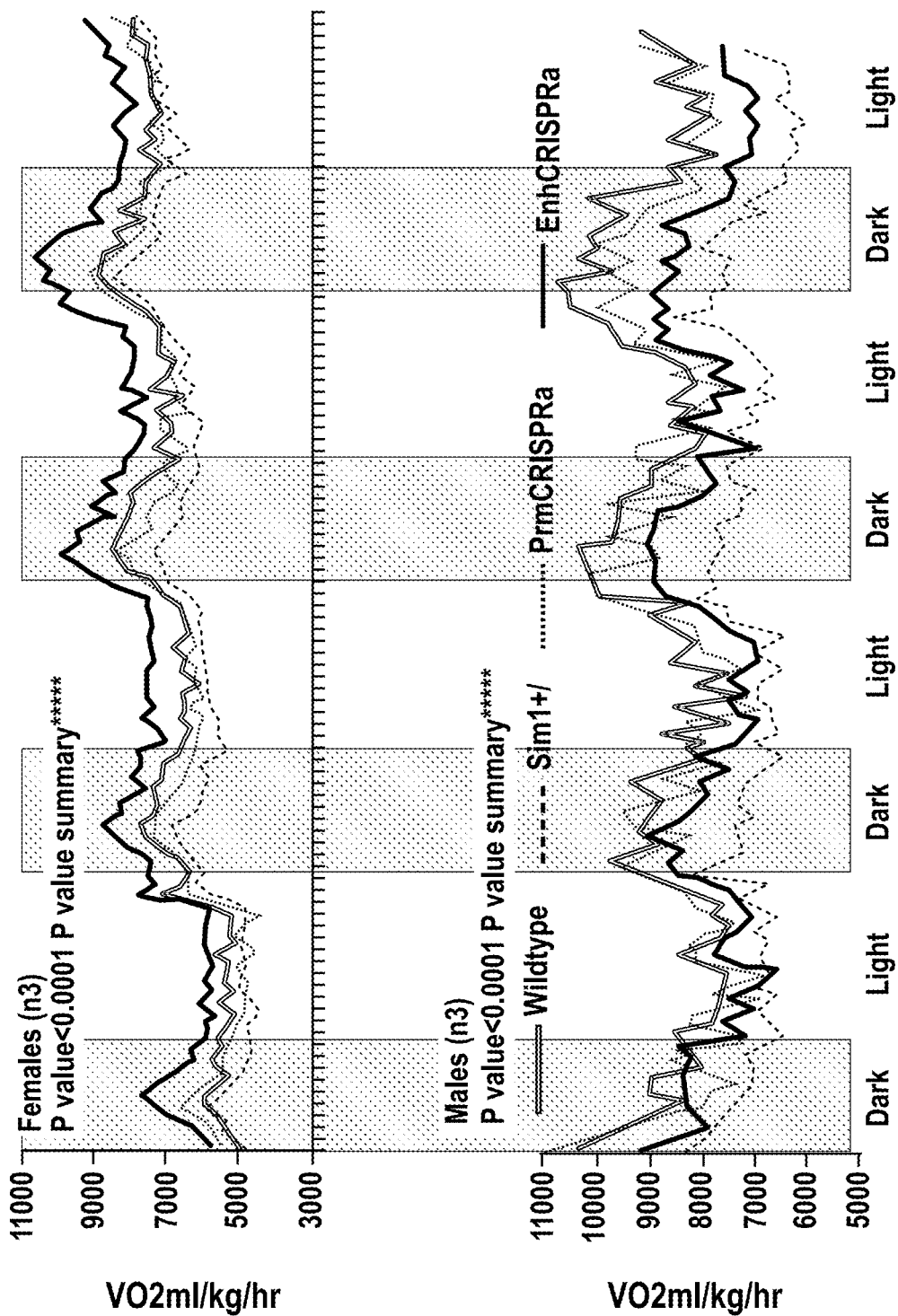

To relate body weight reduction with body composition and metabolic parameters, we next performed metabolic profiling for $Sim1^{+/-} \times H11P^{CAG-dCas9-VP64} \times ROSA26^{Sim1Pr-sgRNA}$ (Prm CRISPRa) $Sim1^{+/-} \times H11P^{CAG-dCas9-VP64} \times ROSA26^{SCE2En-sgRNA}$ (Enh-CRISPRa) and our other mouse lines. Three mice for each genotype were analyzed for body composition and metabolic profiling, right at the onset of the obesity phase, 6-8 weeks of age. Both Prm-CRISPRa and Enh-CRISPRa mice showed a significant reduction in body fat content compared to $Sim1^{+/-}$ in both females and males (FIG. 2A). Metabolic chamber analyses of other hallmarks of $Sim1^{+/-}$ obese mice such as oxygen consumption and food intake showed a shift towards wild-type metabolic parameters in the Prm-CRISPRa and Enh-CRISPRa mice (FIG. 2B-2C). In addition, their respiratory exchange ratio (RER; VCO2/VO2), an indirect method of defining basic metabolic rate, also showed parameters similar to their wild-type littermates (FIG. 2D). However, we did not observe any significant differences for their physical activity in individual chambers. Combined, these results show that both Prm-CRISPRa and Enh-CRISPRa mice have less body fat and demonstrate an improvement in their metabolic parameters that contribute towards a reduction in their overall body weight.

D. Sim1 Activation is Tissue-Specific

Figure 3A:
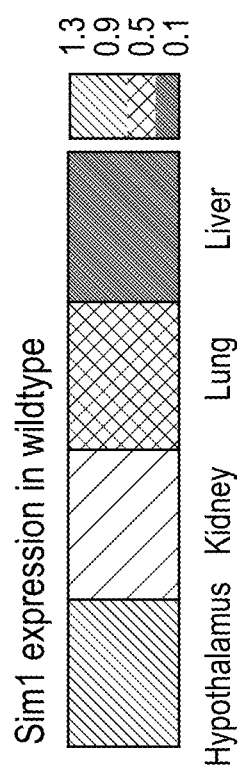
FIGS. 3A-3D dCas9 and Sim1 mRNA expression levels in CRISPRa transgenic mice. A, Heatmap of Sim1 tissue expression. Red and grey filled squares signify tissues where Sim1 is expressed and not expressed, respectively as determined in our wild-type mice. B, dCas9 mRNA expression in the hypothalamus, kidney, lung and liver from 4 Sim1$^{+/-}$× H11P$^{CAG-dCas9-VP64}$ mice. The mean values±s.d were determined based on mRNA fold-increase normalized to beta-actin (for hypothalamus) and Rp138 (for kidney, lung, liver) using the ΔΔCT method. C-D, Sim1 mRNA expression in the hypothalamus, kidney, lung and liver for the following genotypes: wild-type littermates, Sim1$^{+/-}$, H11P$^{CAG-dCas9-VP64}$×ROSA26$^{Sim1Pr-sgRNA}$ (Prm-CRISPRa) and H11P$^{CAG-dCas9-VP64}$×ROSA26$^{SCE2En-sgRNA}$ (Enh-CRISPRa) from 2 females (C) and 2 male (D). The mean values±s.d were determined based on mRNA fold-increase compared to wild-type littermates and normalized to beta-actin or Rp138 using the ΔΔCT method. B.D.L=below detected levels.
Figure 3B:
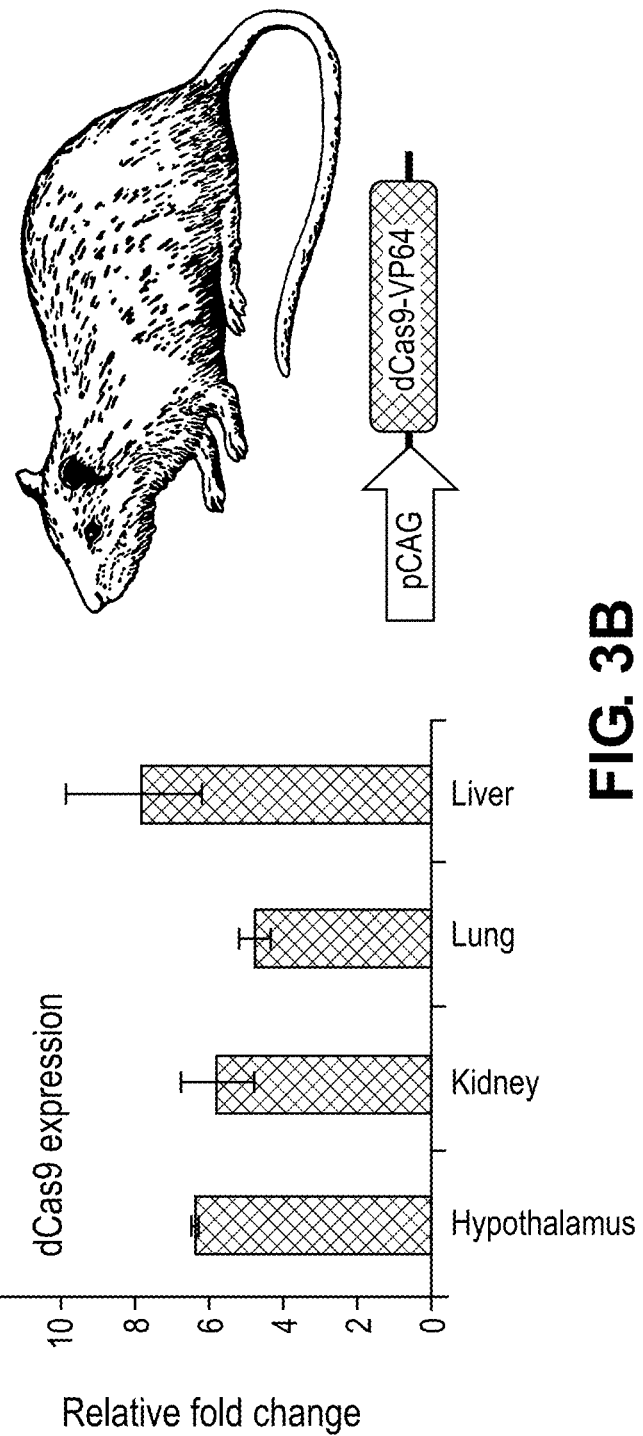
Figures 3C, 3D:
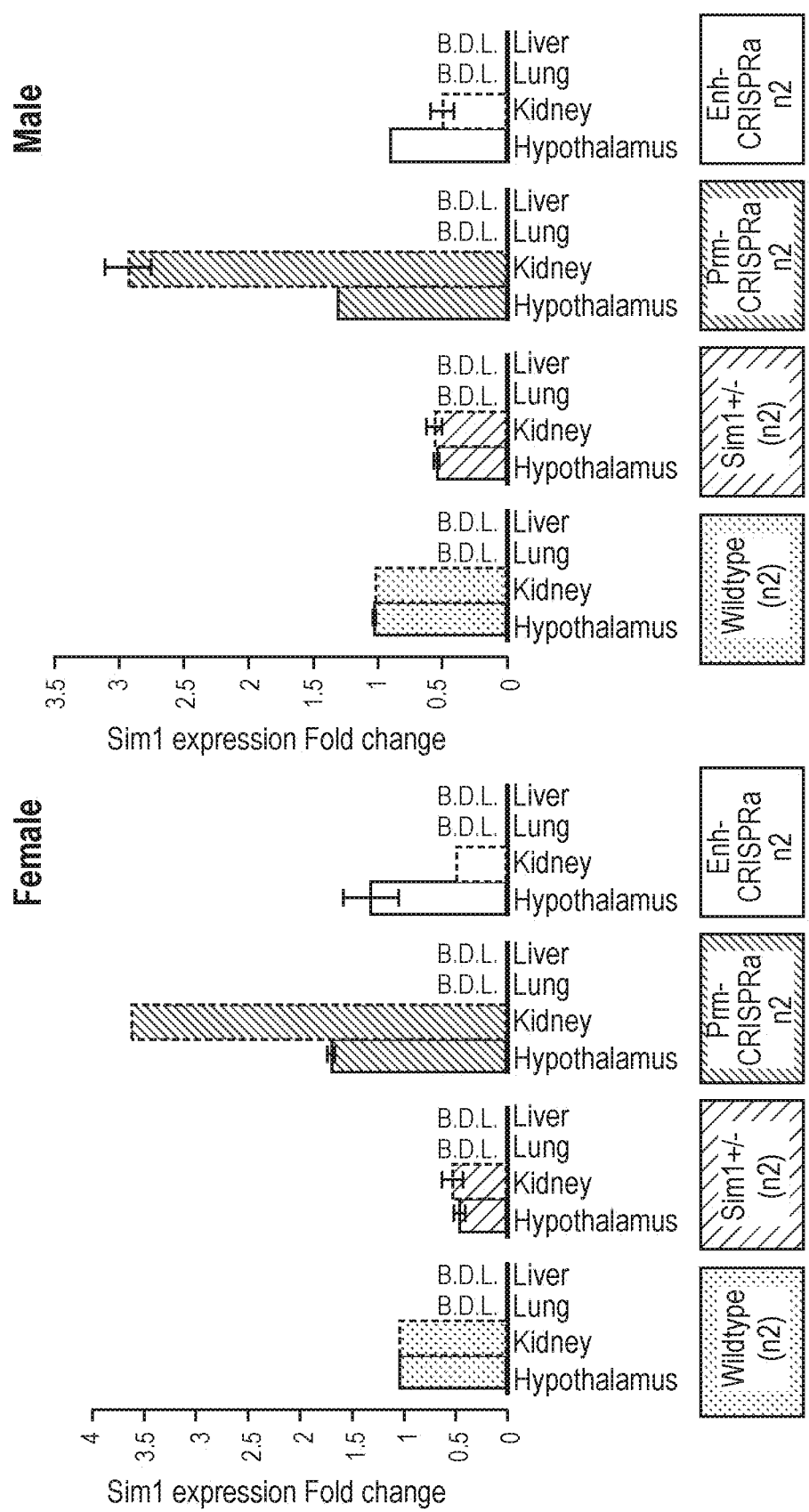

To test for Sim1 activation levels and tissue-specificity in our mice, we measured its mRNA expression levels in different tissues. We selected two tissues where Sim1 is known to be expressed, hypothalamus and kidney, and two tissues where it is not expressed, lung and liver (25) (FIG. 3A). We first measured dCas9 expression, and found it to be expressed in all four tissues, as expected, since we used a ubiquitous CMV enhancer chicken beta-Actin (CAG) promoter to drive its expression (FIG. 3B). In contrast, for Sim1, we observed significantly higher mRNA levels in the hypothalamus and kidney in Prm-CRISPRa mice and only in the hypothalamus of Enh-CRISPRa mice compared to $Sim1^{+/-}$ mice (FIG. 3C-3D). Since we did not observe any significant differences between the obesity phenotype of Prm-CRISPRa and Enh-CRISPRa mice, we could speculate that the activation of Sim1 in the hypothalamus is sufficient to rescue the $Sim1^{+/-}$ obesity phenotype. Interestingly, in tissues where Sim1 is not expressed (i.e. liver and lung), we could not detect Sim1 expression in Prm-CRISPRa or Enh-CRISPRa mice despite observing Cas9 expression. These results imply that in the in vivo conditions of our study, dCas9-VP64 could only upregulate expression in tissues where the cis-regulatory elements of its target gene are active. This suggests that cis-regulatory elements could be used to determine the tissue-specificity of CRISPRa.

E. CRISPRa AAV Reduces Sim1$^{+/-}$ Weight Gain

Figure 8B:
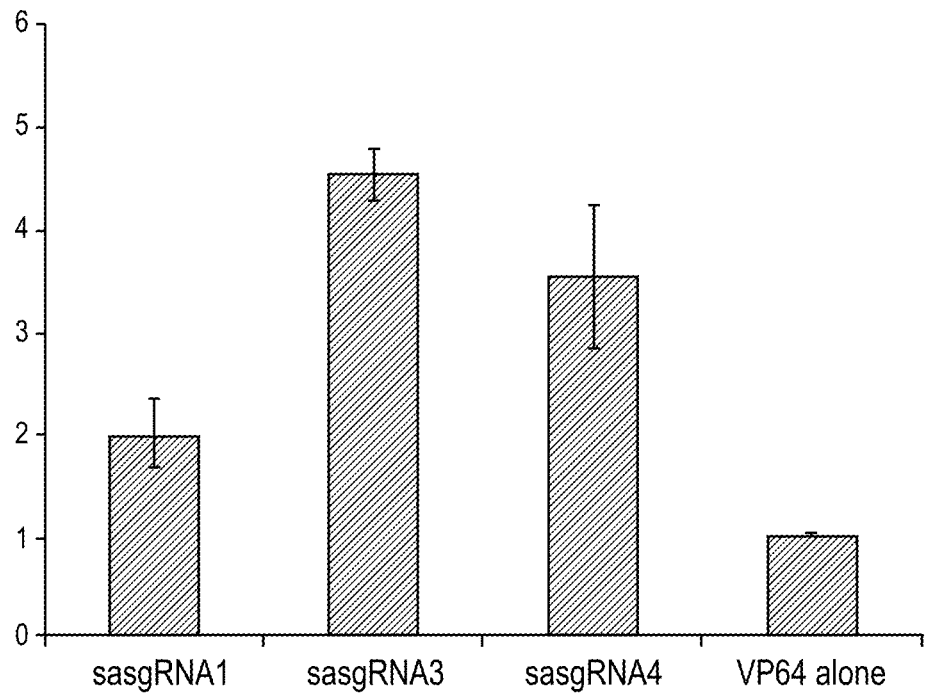

To further translate this approach to a therapeutic strategy for haploinsufficiency, we took advantage of AAV to deliver CRISPRa into the hypothalamus of Sim1$^{+/-}$ mice. We generated the following three AAV vectors: 1) dCas9-VP64 driven by a cytomegalovirus (CMV) promoter (pCMV-dCas9-VP64); 2) Sim1 promoter sgRNA along with mCherry (pU6-Sim1Pr-CMV-mCherry); 3) SCE2 sgRNA along with mCherry (pU6-SCE2-CMV-mCherry). For the pCMV-dCas9-VP64 vector, due to the size of dCas9-VP64 expression cassette, we obtained a 5.4 kb insert. While this insert size is above the 4.7 kb limit, it was shown that going above 5 kb reduces transgene expression levels but still could be used for delivery (26). These vectors were packaged individually into AAV-DJ serotype, which is a chimera of type 2, 8 and 9 that was shown to achieve high expression levels in multiple tissues (27) (FIG. 4A). We did observe lower but usable viral titers for pCMV-dCas9-VP64 AAV (see methods). We first tested if of our AAV CRISPRa vectors could overexpress Sim1 in vitro using Neuro-2a cells. We observed a 4 and 5 fold upregulation of Sim1 mRNA expression when targeting the promoter or enhancer respectively (FIG. 4A). Using additional sgRNAs (SEQ ID NOS:38, 40 or 42), we observed that our AAV CRISPRa vectors could overexpress Sim1 in vitro using Neuro-2a cells. We observed a 2-fold to 6-fold upregulation of Sim1 mRNA expression when targeting the promoter (FIG. 7B) and a 2-fold to 4.5-fold upregulation of Sim1 mRNA expression when targeting the enhancer (SCE2) (FIG. 8B).

Figure 4D:
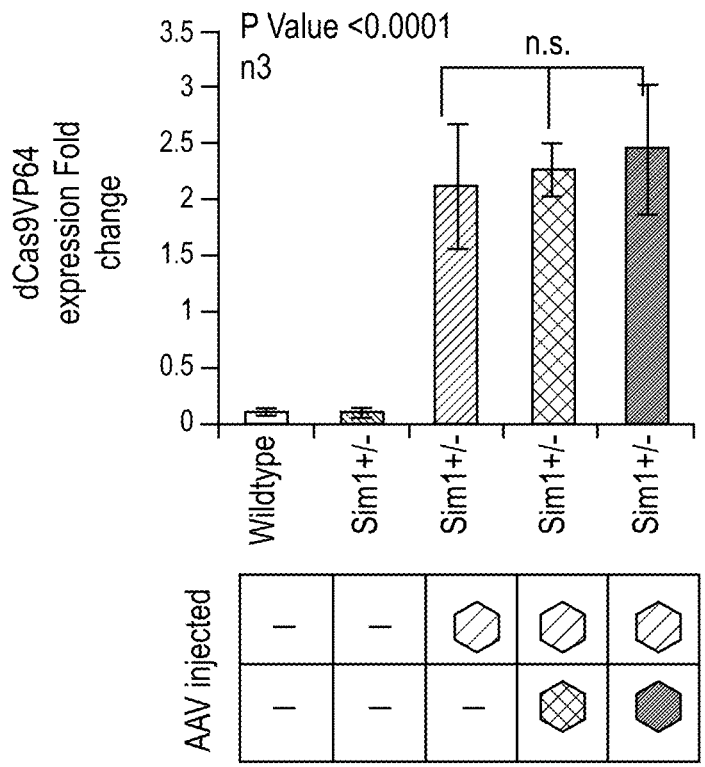
Figure 4E:
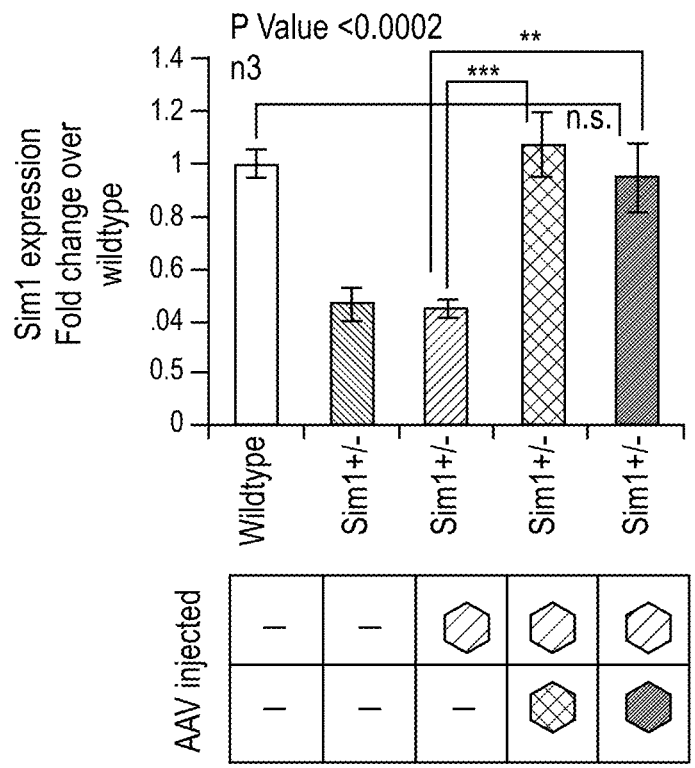
Figure 5A:
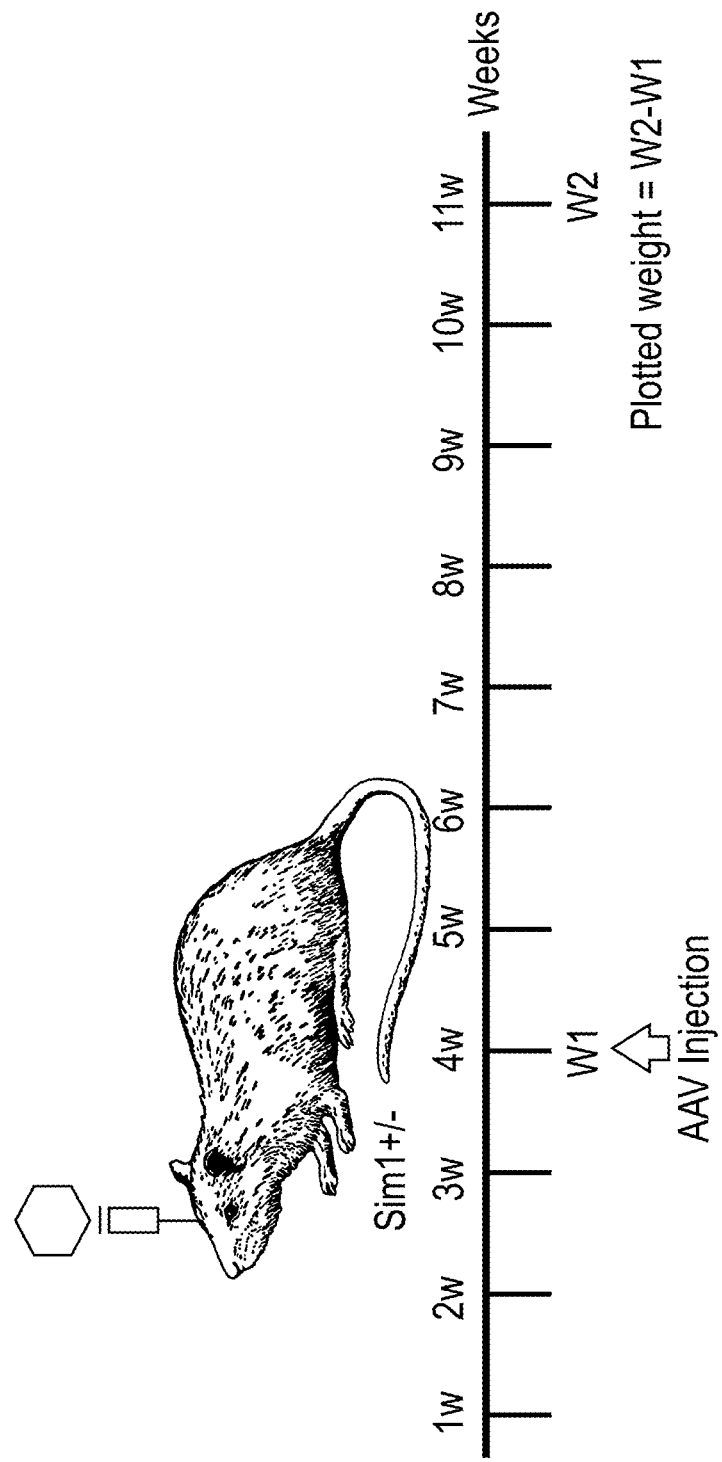
FIGS. 5A-5C CRISPRa-AAV injection in PVN reduces weight gain in Sim1$^{+/-}$ mice. A, Timeline for weight measurement post CRISPRa-AAV injection in PVN. B-C, Weight gain determined over a 7 week period from Sim1$^{+/-}$ mice injected with pCMV-dCas9-VP64 (dCas9-VP64), pCMV-dCas9-VP64+pSim1Pr-mCherry (Prm-CRIPSRa) pCMV-dCas9-VP64+pSCE2En-mCherry (Enh-CRISPRa) compared to un-injected wild-type littermates and Sim1$^{+/-}$ mice. Mean values±s.d are shown from 3 females (B) and 3 males (C). *=p-value<0.001***=p-value<0.0005 n.s=non-significant; (ANOVA, Tukey test).
Figure 5B:
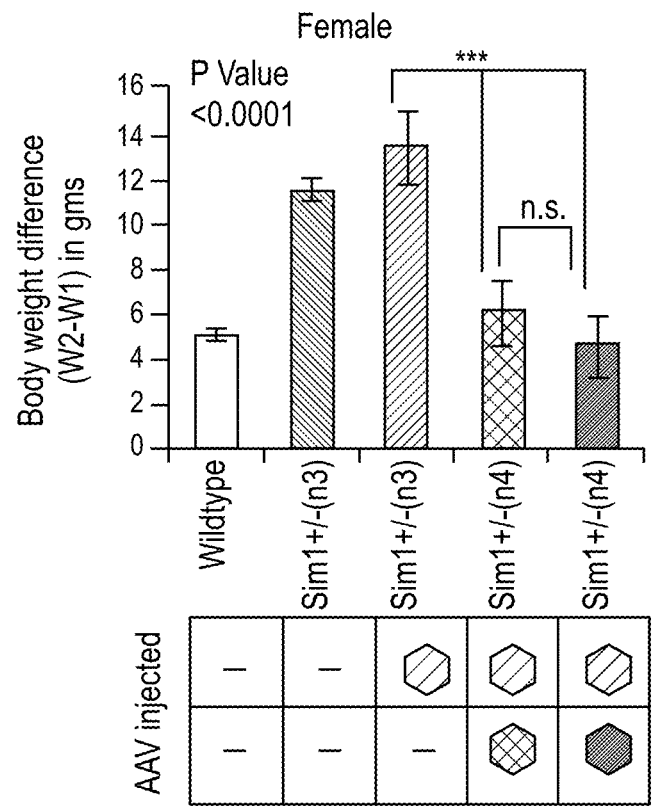
Figure 5C:
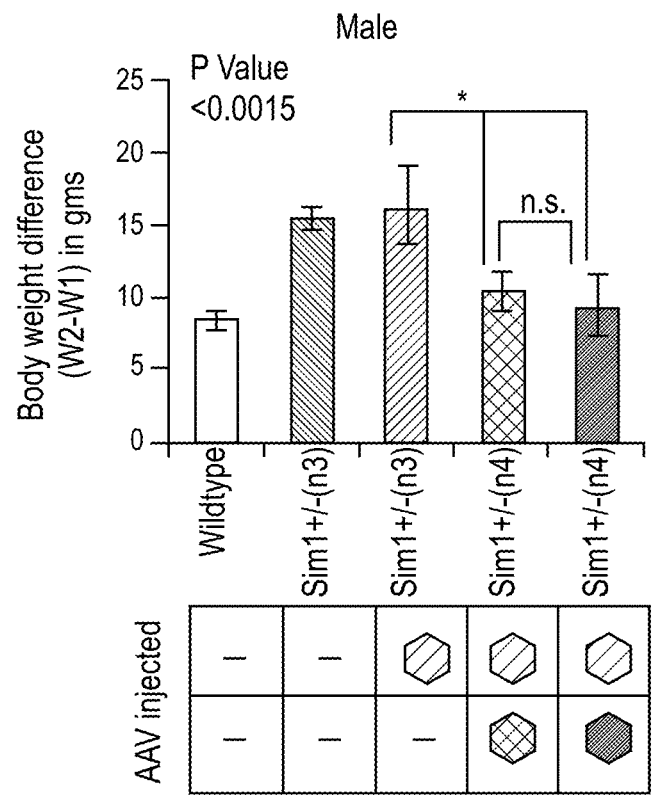

Next, we performed stereotactic injections to deliver virus carrying pCMV-dCas9-VP64 and either pU6-Sim1Pr-CMV-mCherry (Prm-CRISPRa-AAV) or pU6-SCE2-CMV-mCherry (Enh-CRISPRa-AAV) into the PVN of the hypothalamus of Sim1$^{+/-}$ mice at four weeks of age, before they start developing obesity. As negative controls, we also injected Sim1$^{+/-}$ mice with pCMV-dCas9-VP64 virus only. We tested for the expression of our sgRNA-CMV-mCherry cassette by performing immunostaining on the hypothalamus of injected mice and found it to be expressed in the PVN (FIG. 4B-4C). To test whether Sim1 expression levels were increased by delivering CRISPRa-AAV to the hypothalamus of Sim1$^{+/-}$ mice, we measured mRNA expression levels for both dCas9 and Sim1 from 11 week old AAV injected mice. dCas9 was found to be expressed in the hypothalamus of all our pCMV-dCas9-VP64 AAV injected mice (FIG. 4D). Sim1 upregulation was observed in both Prm-CRISPRa-AAV and Enh-CRISPRa-AAV injected hypothalami, but not in mice injected with only pCMV-dCas9-VP64-AAV (FIG. 4E). The injected mice were measured for body weight up to 11 weeks of age (FIG. 5A). We observed a significant weight reduction in the Prm-CRISPRa-AAV or Enh-CRISPRa-AAV injected mice compared to the Sim1$^{+/-}$ or pCMV-dCas9-VP64-AAV injected Sim1$^{+/-}$ mice (FIG. 5B-5C). These results show that CRISPRa-AAV mediated upregulation could be used as a viable gene therapy tool to treat haploinsufficiency.

F. Upregulation of Mc4r In Vitro

Over 70% of obesity that has genetic basis is caused by defects in the leptin pathway. MC4R is part of the leptin pathway and mutations in it are the most commonly found mutations in obese individuals (~5% of the 1 percentile obese population). Since it is a downstream factor, upregulation of MC4R and SIM1 could possibly rescue obesity caused by mutations in these other leptin pathway genes. Here, we have shown that we can upregulate MC4R by targeting its promoter and have also shown that upregulation of SIM1 can increase MC4R expression. We were also able to rescue the obesity phenotype in Mc4r heterozygous mice (performed essentially as set forth in the upregulation of Sim1 in vitro, discussed above). As such, MC4R upregulation could be used as therapy for obesity.

Figure 9A:
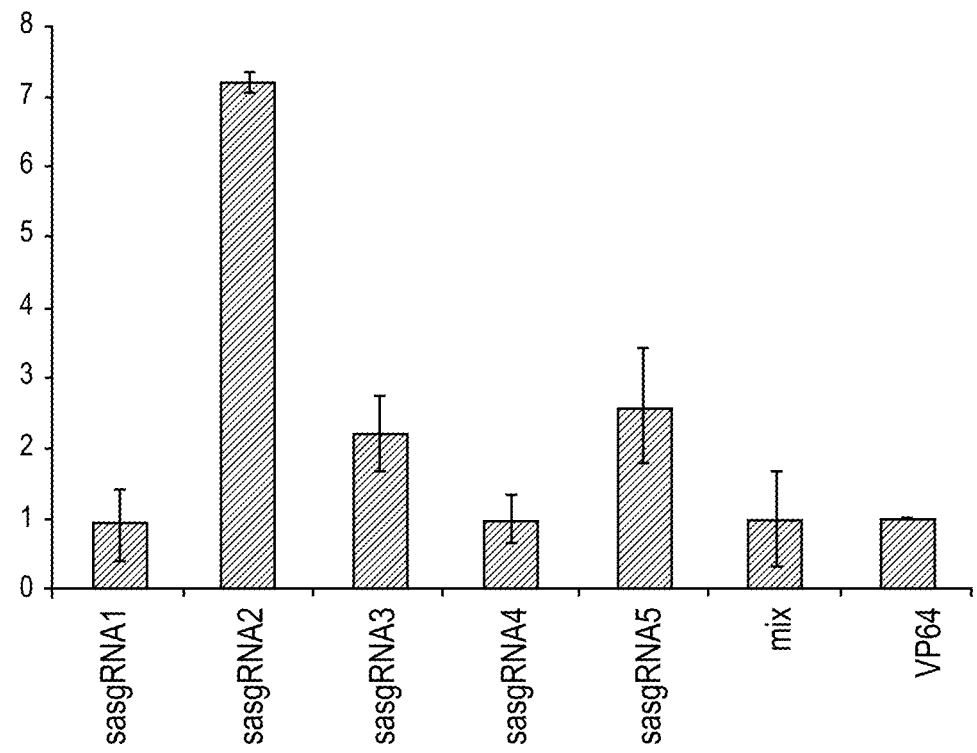
FIG. 9A-9B: CRISPRa Mc4r overexpression in vitro.

We designed sgRNAs for the Mc4r promoter (See, SEQ ID NOS:50-54). Using these guides we tested if dCas9 fused to VP64 (dCas9-VP64) can overexpress Mc4r in mouse neuroblastoma cells (Neuro-2a). Cells were transfected with dCas9-VP64 and the various guides and following 48 hours Mc4r mRNA levels were measured using quantitative PCR (qPCR). We identified one sgRNA for the Mc4r promoter that was able to overexpress endogenous Mc4r by 7-fold (FIG. 9A).

G. CRISPRa AAV Induces Upregulation of Mc4r

Figure 9B:
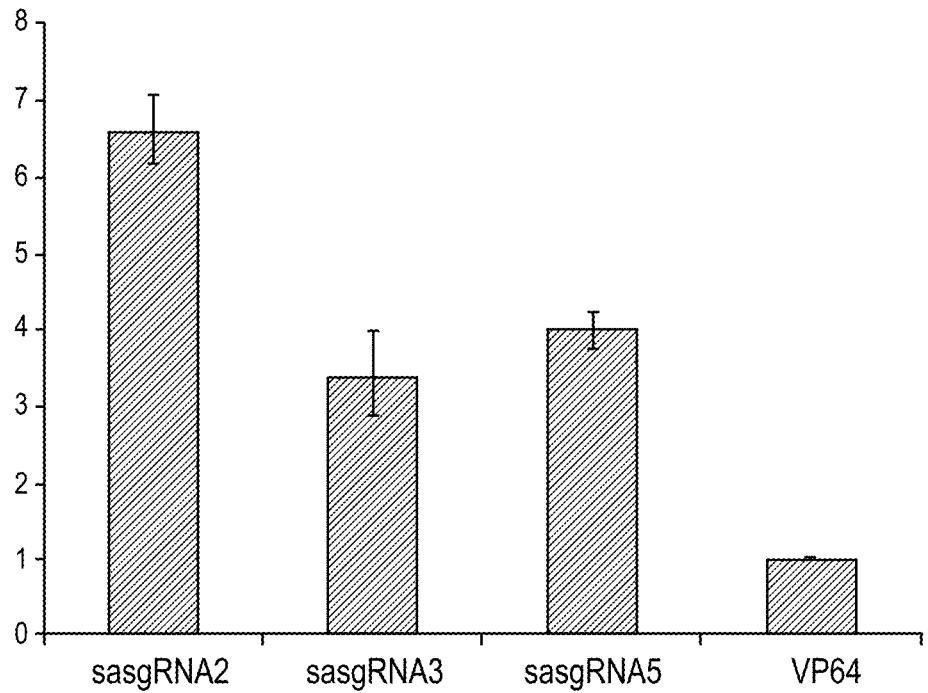

We next tested if of our AAV CRISPRa vectors (prepared essentially as described under Sim1 CRISPRa AAV, above) containing sgRNAs, SEQ ID NOS:51, 52 or 54, could overexpress Mc4r in vitro using Neuro-2a cells. We observed between a 3.4-fold and 6.6-fold upregulation of Mc4r mRNA expression when targeting the promoter (FIG. 9B).

H. Upregulation of SCN2A In Vitro

Mutations in SCN2A are the most commonly found mutations in individuals with autism spectrum disorder (ASD) and epilepsy. The majority of mutations are loss of function leading to ASD due to haploinsufficiency. Here, we have shown that we can upregulate SCN2A by targeting its promoter. As such, SCN2A upregulation could be used as therapy for ASD and epilepsy.

Figure 12A:
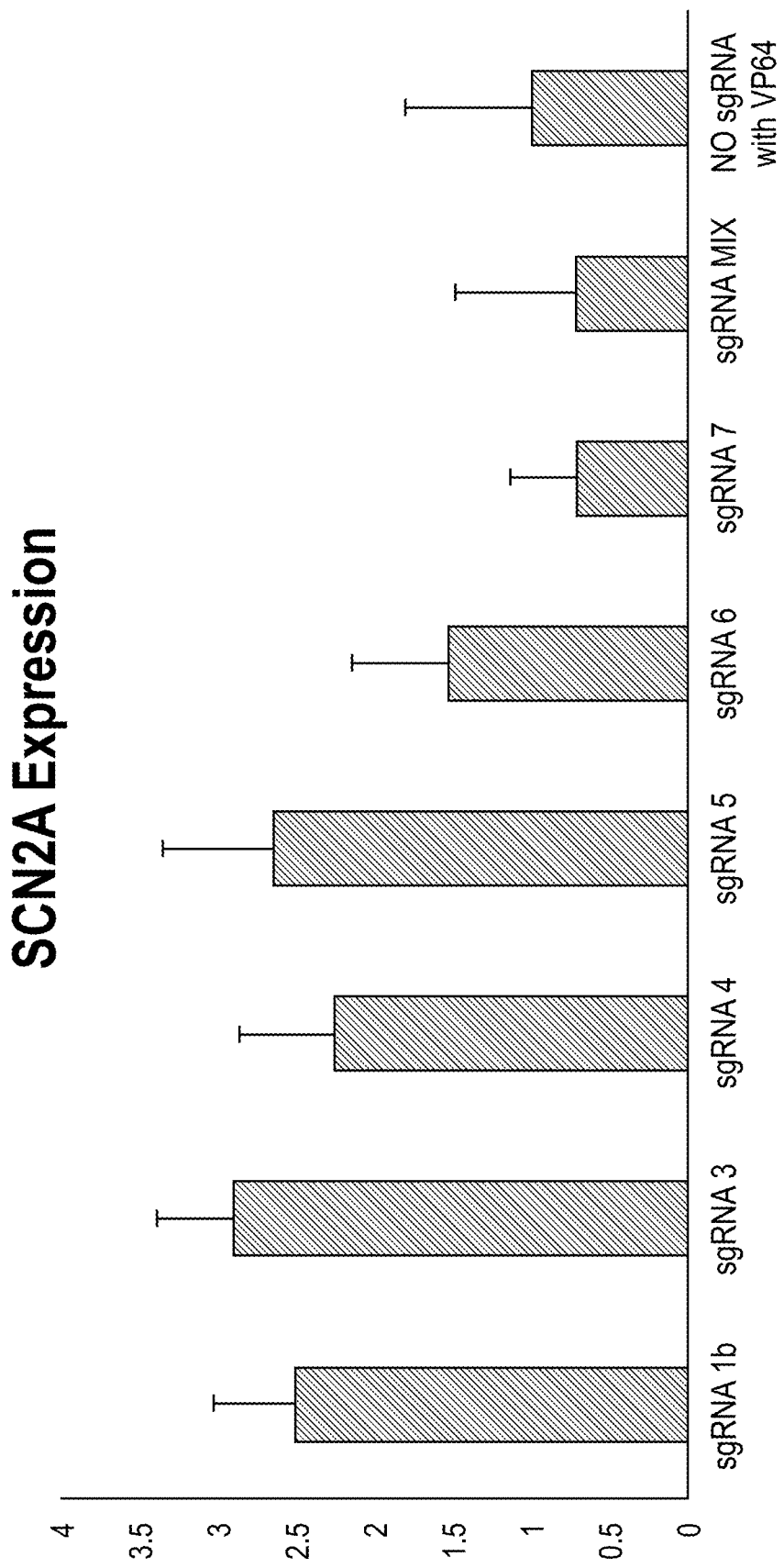
FIG. 12A-12B: CRISPRa Scn2A overexpression in vitro.

We designed sgRNAs for the Scn2a promoter (See, SEQ ID NOS:85-91). Using these guides we tested if dCas9 fused to VP64 (dCas9-VP64) can overexpress Scn2a in mouse neuroblastoma cells (Neuro-2a). Cells were transfected with dCas9-VP64 and the various guides and following 48 hours Scn2a mRNA levels were measured using quantitative PCR (qPCR). We identified four sgRNAs for the Scn2a promoter that were able to overexpress endogenous Scn2a by over 2-fold (FIG. 12A).

I. CRISPRa AAV Induces Upregulation of Scn2A

Figure 12B:
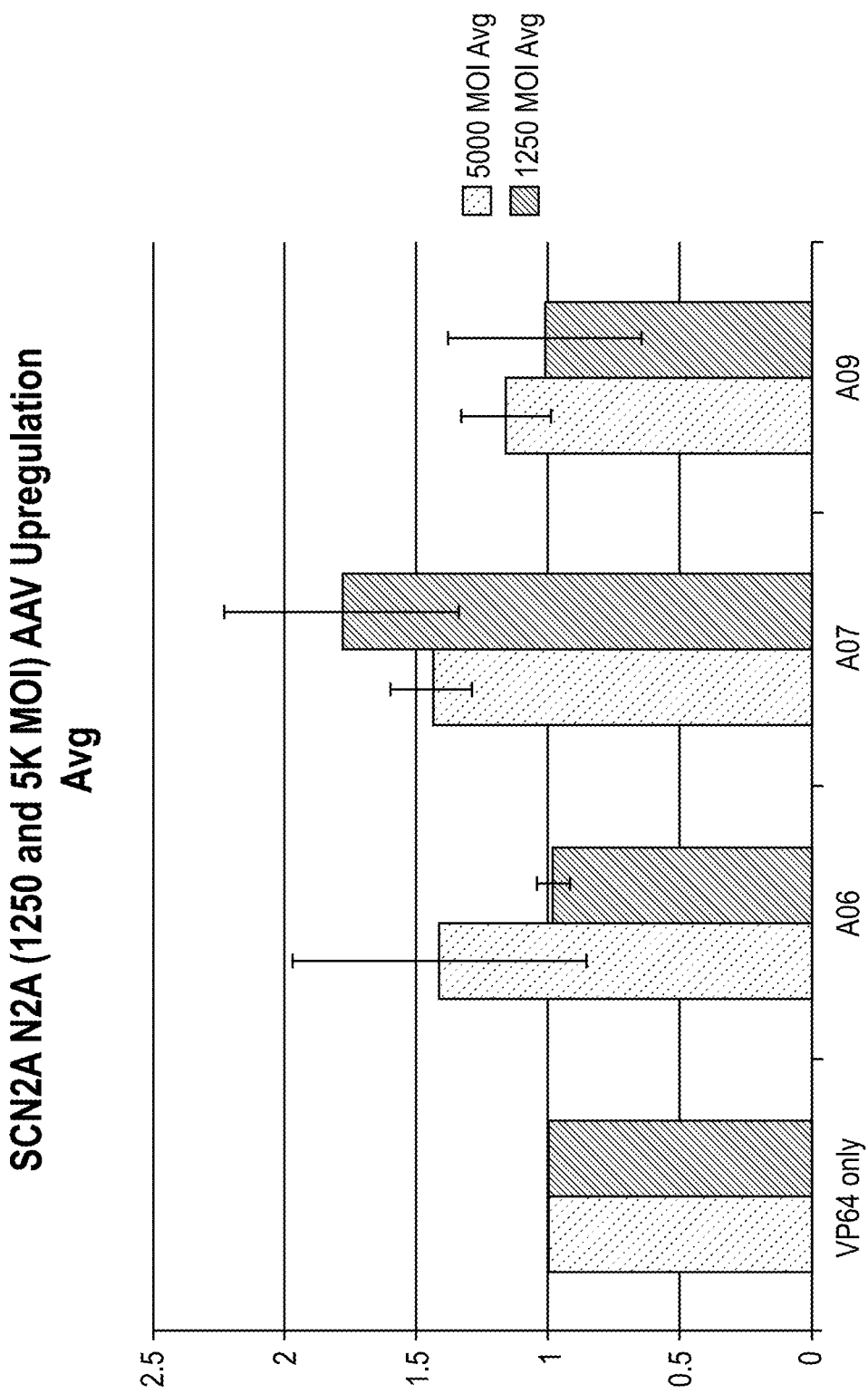

We next tested if of our AAV CRISPRa vectors (prepared essentially as described under Sim1 CRISPRa AAV, above) containing sgRNAs, SEQ ID NOS:92-94, could overexpress Scn2a in vitro using Neuro-2a cells. Two different multiplicity of infection (MOI) were used: 5,000 and 1,750 viral genome (vg/ml). We observed a slight upregulation of Scn2a mRNA expression when targeting the promoter with a MOI of 5,000 viral genomes per ml (FIG. 12B).

J. Upregulation of SETD5 In Vitro

Mutations in SETD5 lead to mental retardation-23 (OMIM #615761) which include intellectual disability and dysmorphic features. Here, we have shown that we can upregulate SETD5 by targeting its promoter. As such, SETD5 upregulation could be used as therapy for intellectual disability.

Figure 11A:
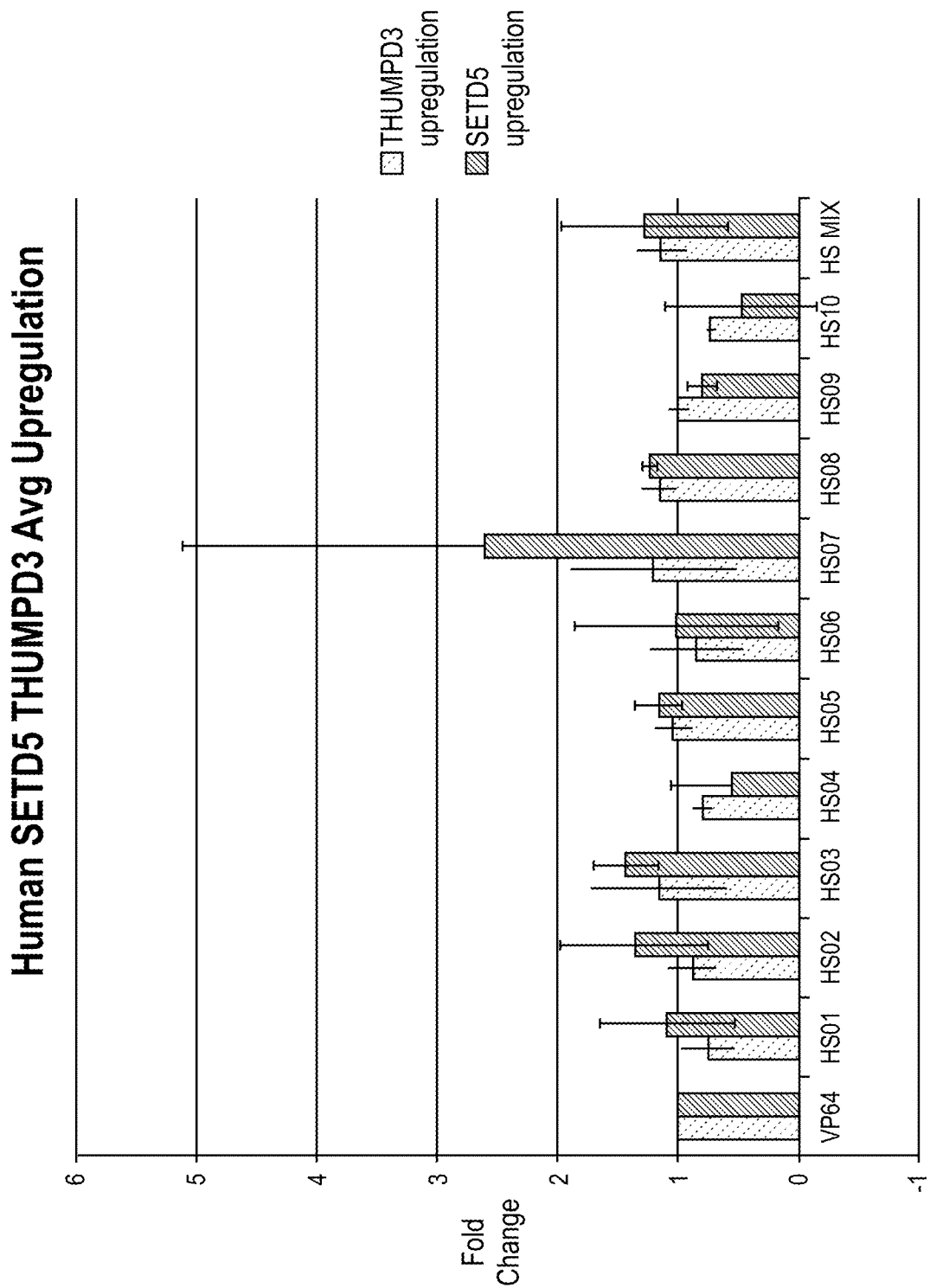
FIG. 11A-11B: CRISPRa SETD5 overexpression in vitro.
Figure 11B:
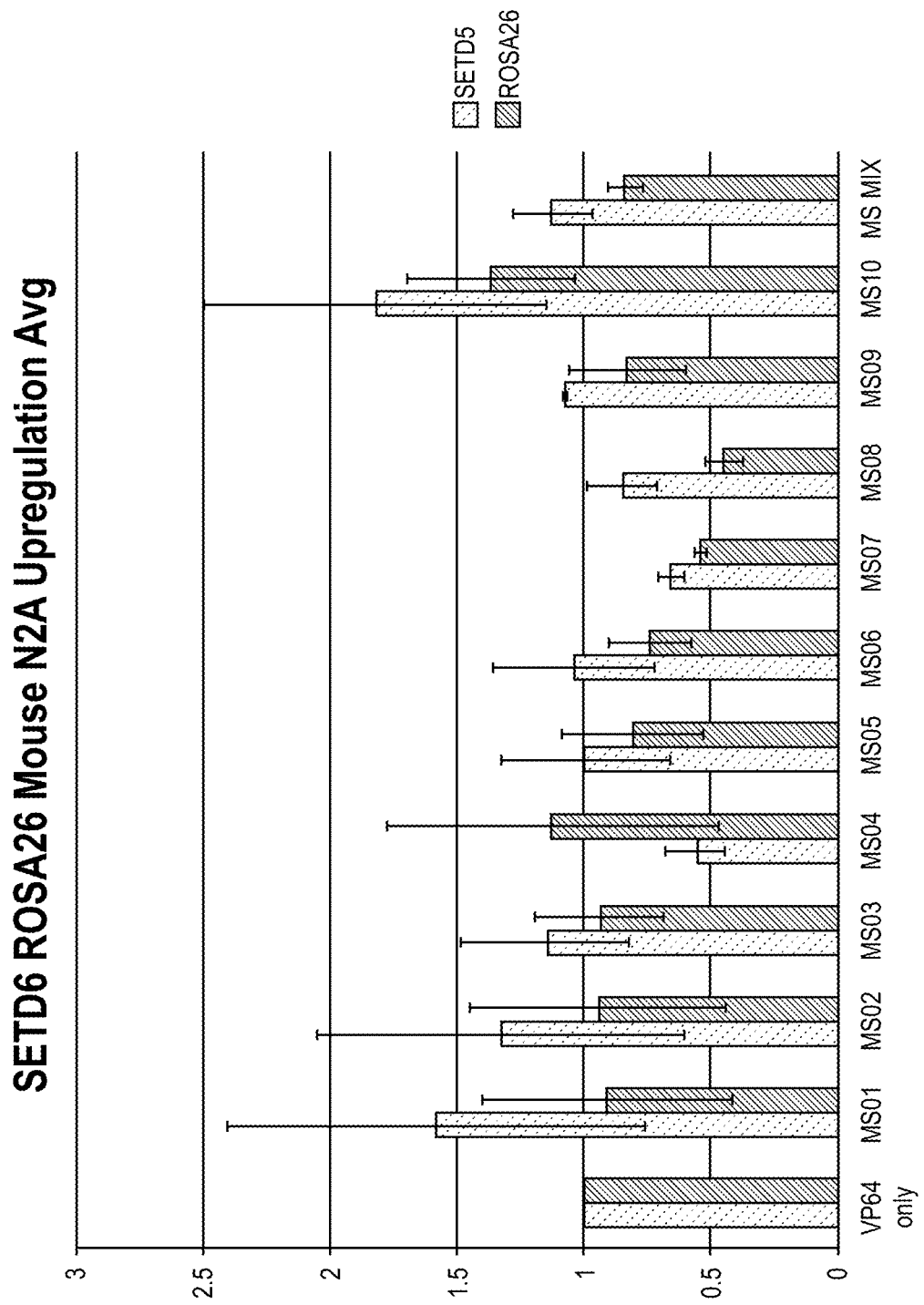

We designed sgRNAs for the Setd5 promoter (See, SEQ ID NOS:75-84). Using these guides we tested if dCas9 fused to VP64 (dCas9-VP64) can overexpress Setd5 in mouse neuroblastoma cells (Neuro-2a). Cells were transfected with dCas9-VP64 and the various guides and following 48 hours Setd5 mRNA levels were measured using quantitative PCR (qPCR). We identified two sgRNAs for the Setd5 promoter that were able to overexpress endogenous Setd5 by over 1.5-fold (FIG. 11B).

Next, we designed sgRNAs for the SETD5 promoter in humans (See, SEQ ID NOS:65-74). Using these guides we tested if dCas9 fused to VP64 (dCas9-VP64) can overexpress SETD5 in human HEK293T cells. Cells were transfected with dCas9-VP64 and the various guides and following 48 hours SETD5 mRNA levels were measured using quantitative PCR (qPCR). We identified at least one sgRNA for the SETD5 promoter that was able to overexpress endogenous SETD5 by over 2.5-fold (FIG. 11A).

K. Upregulation of PKD1 In Vitro

Mutations in PKD1 lead to autosomal dominant polycystic kidney disease (ADPKD; OMIM #173900) which is the most frequent hereditary kidney disorder affecting 1 to 400-1000 individuals. 85% of ADPKD is caused by mutations in PKD1, the majority of which are loss-of-function. PKD1 is 13 kb long and as such cannot be packaged in standard gene therapy vectors. Using the CRISPRa technology disclosed herein, we have shown that we can upregulate PKD1 by targeting its promoter. As such, PKD1 upregulation could be used as therapy for autosomal dominant polycystic kidney disease.

Figure 10:
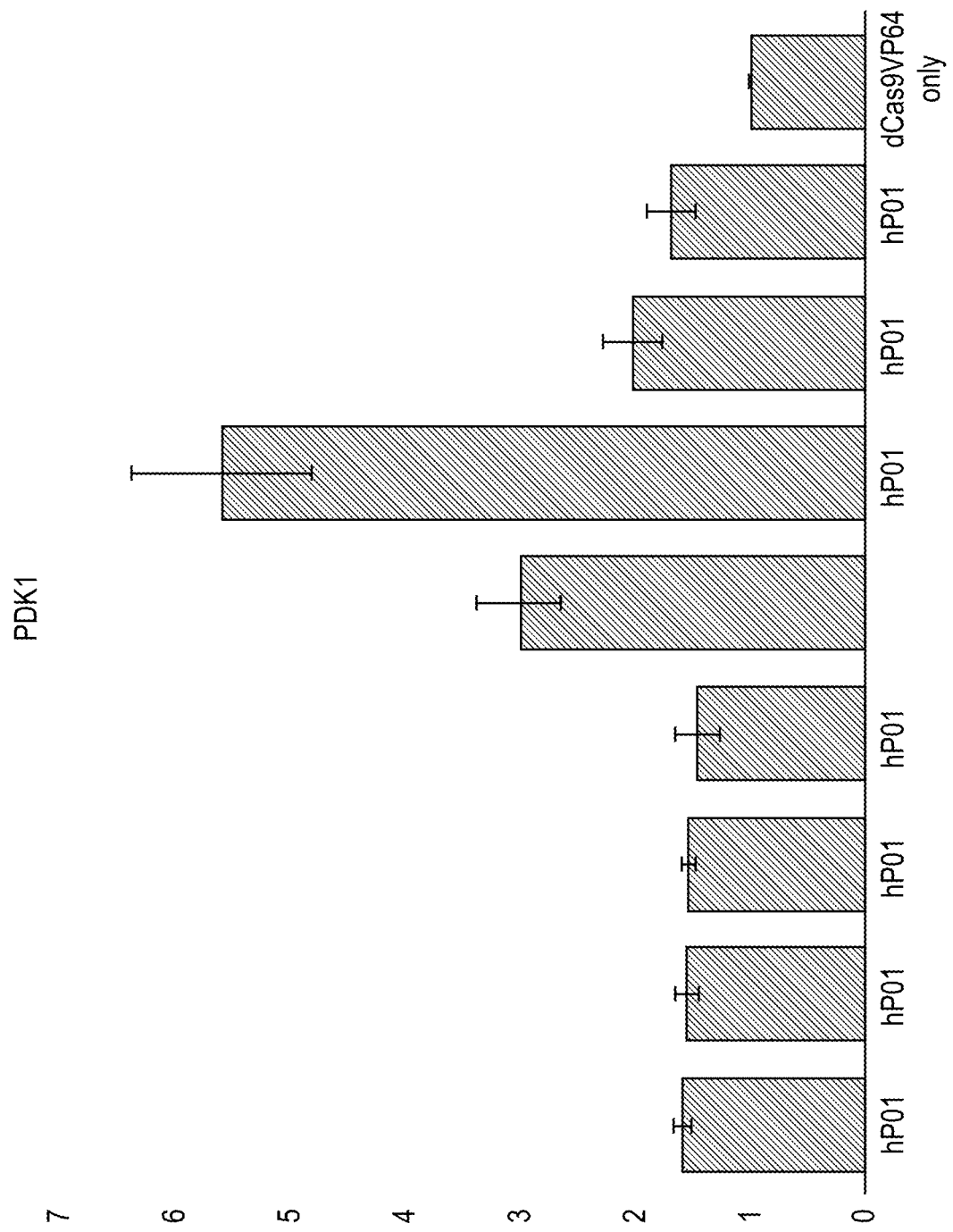
FIG. 10: CRISPRa PKD1 overexpression in vitro. An exemplary *S. aureus* CRISPRa system targeting the PKD1 promoter (Pr) by transfection of human promoter sgRNA's (SEQ ID NOS:55-64) into human HEK293T cells. Results are expressed as mRNA fold-increase normalized to dCas9-VP64. The mean values±s.d. were obtained from 3 independent experiments.

We designed sgRNAs for the PKD1 promoter in humans (See, SEQ ID NOS:55-64). Using these guides we tested if dCas9 fused to VP64 (dCas9-VP64) can overexpress PKD1 in human HEK293T cells. Cells were transfected with dCas9-VP64 and the various guides and following 48 hours PKD1 mRNA levels were measured using quantitative PCR (qPCR). We identified at least three sgRNAs for the PKD1 promoter that were able to overexpress endogenous PKD1 by over 2-fold (FIG. 10).

L. Upregulation of PAX6 In Vitro

Loss-of-function mutations in PAX6 lead to Aniridia 1 (OMIM #106210) due to haploinsufficiency. Here, we have shown that we can upregulate PAX6 by targeting its promoter. As such, PAX6 upregulation could be used as therapy for aniridia 1.

Figure 13:
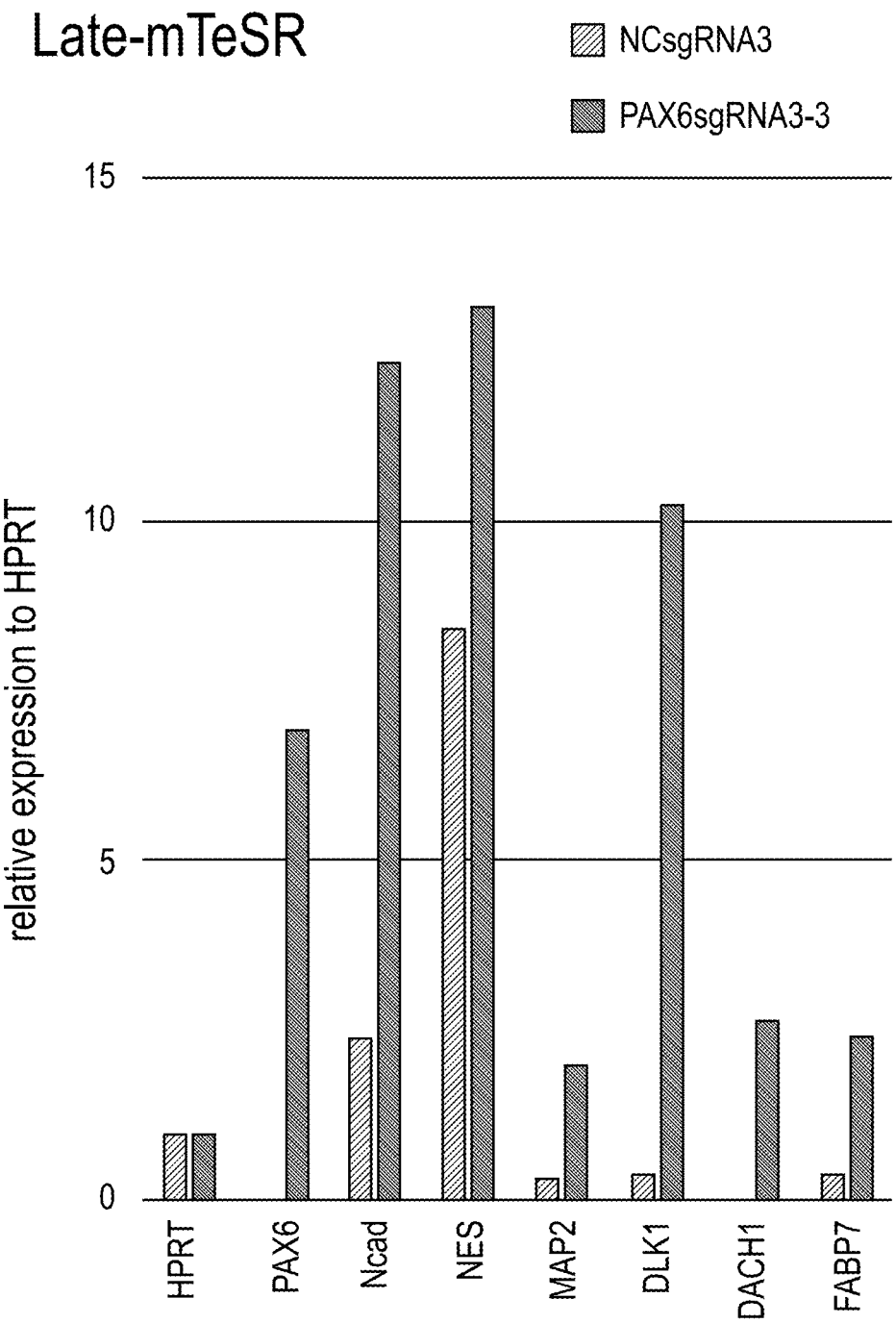
FIG. 13: CRISPRa PAX6 overexpression in vitro. shows an exemplary *S. pyogenes* (Sp) Cas9 CRISPRa system targeting the PAX6 promoter (Pr) by lentiviral delivery of human promoter sgRNA (SEQ ID NO:95) into human H1-ESC cells differentiated into neurons. Results are expressed as relative expression to HPRT. The mean values±s.d. were obtained from 3 independent experiments. Additional neuronal markers are shown to demonstrate that PAX6 CRISPRa leads to neural induction of H1-ESCs.

We designed one sgRNA for the PAX6 promoter in humans (SEQ ID NO:95). Using this guide we tested if dCas9 (*S. pyogenes*) fused to VP64 (dCas9-VP64) can overexpress PAX6 in Human H1-ESC cells differentiated into neurons. Cells were infected with lentivirus carrying the guide, and following 48 hours PAX6 mRNA levels were measured using quantitative PCR (qPCR). Our exemplary sgRNA for the PAX6 promoter was able to overexpress endogenous PAX6 by over 6-fold (FIG. 13). FIG. 13 also demonstrates that additional neuronal markers (e.g., NES) were also capable of neural induction of H1-ESCs.

III. Discussion

CRISPR-based gene editing is a promising therapeutic technology to correct genetic mutations. However, it currently is not a feasible technology for haploinsufficiency, limited by low non-homologous end joining (NHEJ) efficiencies (i.e. editing only a small portion of cells) and the need to custom tailor specific guides and donor sequences for each individual mutation. In addition, it is not a feasible therapeutic strategy for micro-deletions, over 200 of which are known to cause human disease (28), primarily due to haploinsufficiency. In this study, we used a novel approach to tackle these hurdles and show how a haploinsufficient disease could be corrected by increasing the transcriptional output from the existing functional allele via CRISPRa.

Figure 6:
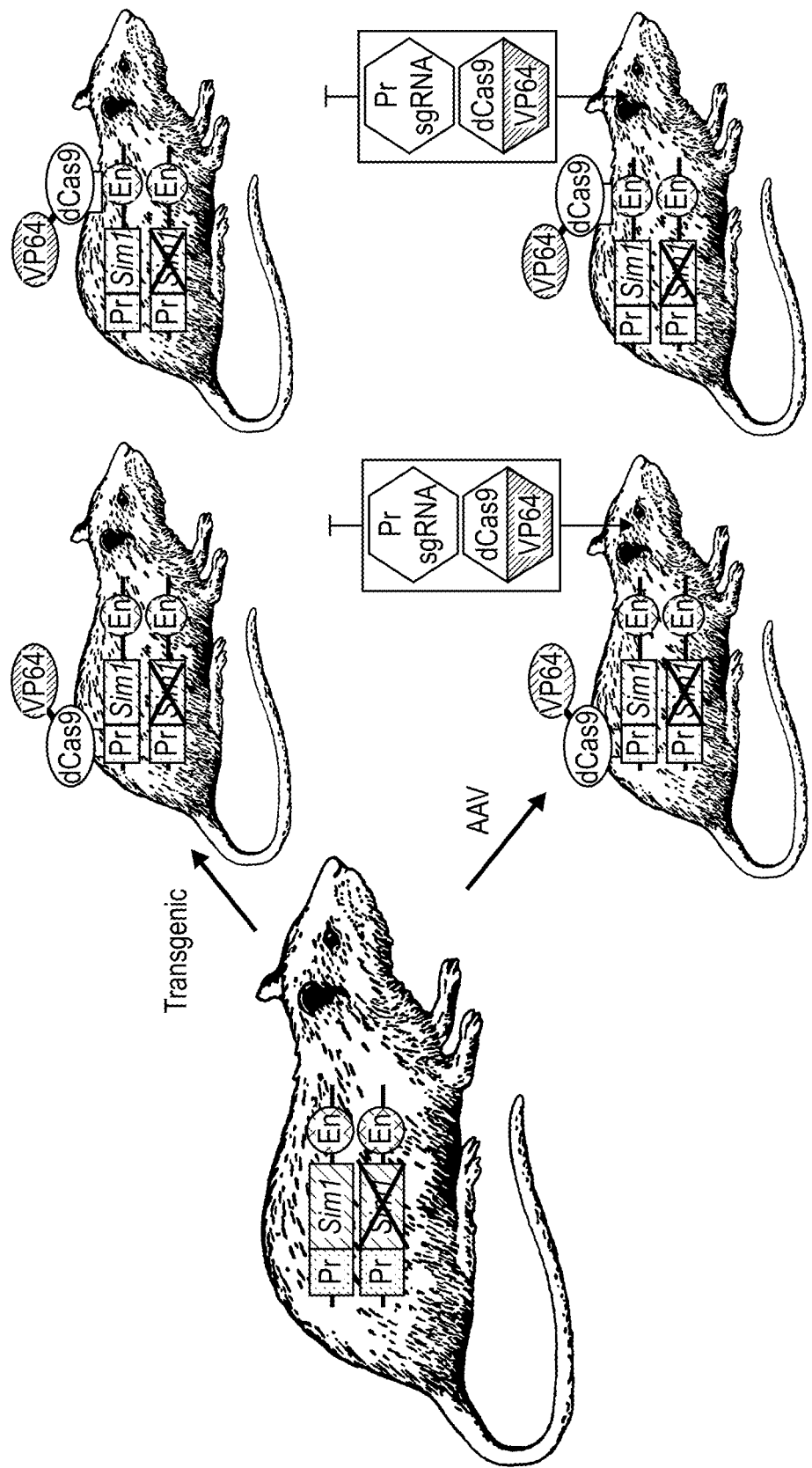
FIG. 6 Schema of CRISPRa haploinsufficiency rescue experiments. The obesity phenotype in Sim1$^{+/-}$ mice was rescued via CRISPRa by targeting either the Sim1 promoter or enhancer using both a transgenic and postnatal AAV approach.
Figure 7A:
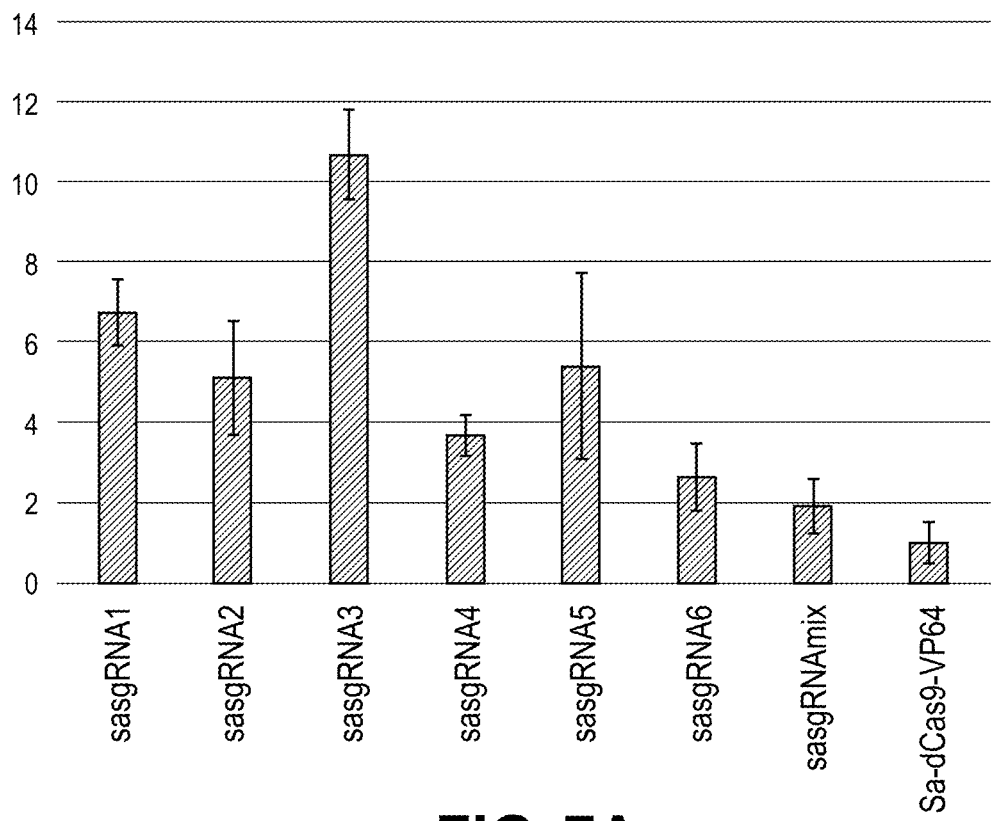
FIG. 7A-7B: CRISPRa Sim1 overexpression in vitro.
Figure 7B:
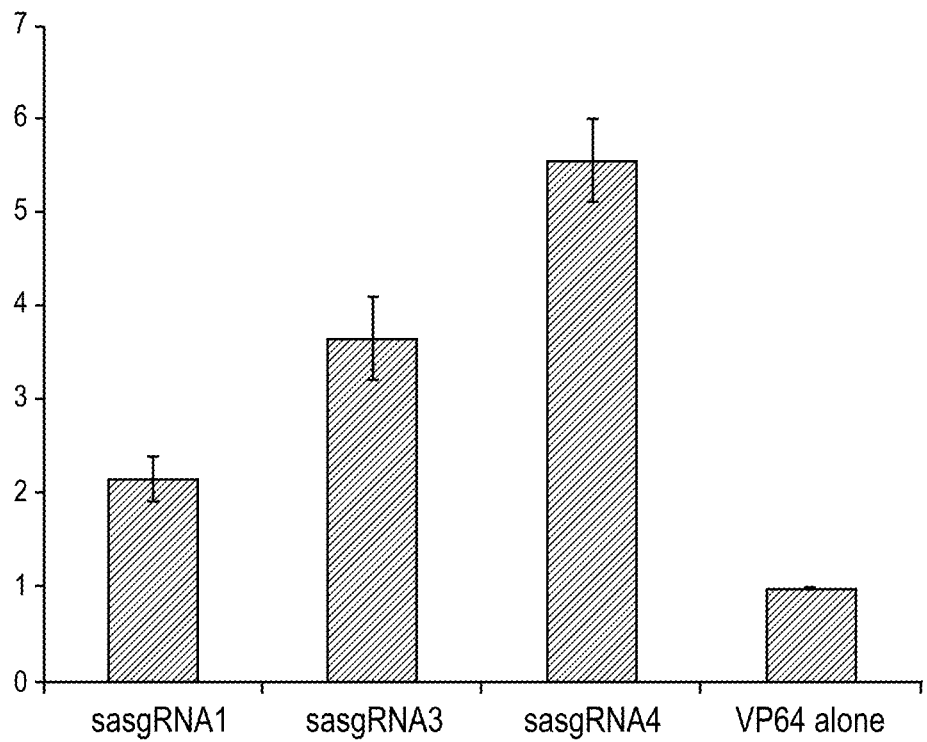

Using CRISPRa targeting for either the promoter or enhancer of Sim1, we were able to rescue the obesity phenotype in a tissue-specific manner in mice that are haploinsufficient for Sim1 (FIG. 6). As this therapeutic approach takes advantage of the existing functional allele, it has several benefits: 1) It overcomes the need to custom tailor CRISPR gene editing approaches for different haploinsufficient causing mutations in the same gene. 2) This approach could potentially be used to target two or more genes. As such, it could pose as a potential therapeutic strategy for micro-deletions related-diseases that are caused by the heterozygous LoF of more than one gene. 3) CRISPRa-AAV could be used to rescue haploinsufficient diseases caused by genes that are longer than its optimal packaging capability. 4) CRISPR-based therapies can take advantage of cis-regulatory elements to guide tissue-specificity. The availability of large-scale tissue-specific maps of gene regulatory elements could provide ample candidates to use for this therapeutic approach. We observed distinct difference in tissue specific activation of Sim1 in our study, which can be attributed to chromatin accessibility of the locus in various tissues. Previous large-scale Cas9 and dCas9 cell culture screens have shown a targeting preference for regions with low nucleosome occupancy (29). Active promoters or enhancers would have lower nucleosome occupancy, thus being more amenable to dCas9 targeting.

Our dCas9-VP64 mouse and AAV vectors can be a useful tool for targeted gene activation in vivo by delivering sgRNA/s targeted to a specific gene/s in certain tissues/cell types. This approach could be used to assess gene-gene interactions or for the identification of the target gene/s of a specific regulatory element in vivo by measuring its expression level following activation. Another potential area of study could be neuronal circuit manipulation. Discrepancies between acute and chronic neuronal circuit manipulations have been observed (30) which can be addressed by our AAV-CRISPRa and Transgenic-CRISPRa strategies respectively.

Haploinsufficiency of Sim1 causes obesity both in mice (17) and humans (13). Whether this is caused by the reduction in PVN size during development that is observed in $Sim1^{+/-}$ mice (17) or by disturbed energy homeostasis during adulthood was an area of major research. The obesity phenotype observed in the postnatal conditional knockout of hypothalamic Sim1 (18), reinforced the hypothesis that Sim1 does indeed have a role in energy homeostasis later during adulthood. Our ability to rescue the obesity phenotype via CRISPRa AAV injections into the hypothalamus of 4 week old mice, further corroborates this role. Abrogation of melanocortin 4 receptor (Mc4r) signaling is the hallmark of most polygenic and monogeneic obesity phenotypes. Conditional postnatal deficiency of Sim1 leads to reduced levels of Mc4r signaling. As Sim1 was shown to be an integral downstream component of the leptin-Mc4r pathway (18), Sim1 CRISPRa targeting could provide a potential therapy for conditions that disrupt the leptin signaling pathway.

Despite technological advances in CRISPR-based therapeutic intervention, our understanding of the long-term side effects of CRISPR expression and its off-targeting effects in-vivo still remains largely unknown, which also holds true for our current study. Anti-CRISPR genes (31) or conditional activation or silencing of our CRISPRa system could be able to address these concerns in future. Furthermore, there is also a need to develop CRISPRa/i tools to modulate gene dosage, so as to be able to optimize transcriptional output for certain diseases where higher or lower activation levels might be needed. In this study, we used VP64 as our activator, due to its known weak activation capacity (23)

which fit with our need to obtain levels of gene expression that are similar to having two normal alleles. CRISPRa based gene activation is dependent upon the nature of the fused activator (23), sgRNA target (29) and may require optimization of the CRISPR system and delivery method.

As demonstrated in this study, CRISPRa can be used to activate genes not only by targeting their promoters, but by also targeting distal cis-regulatory elements such as enhancers. Previous studies have shown that these elements can be viable therapeutic targets. For example, by targeting a globin enhancer with zinc finger nucleases fused to a chromatin looping factor, the LIM domain binding 1 (LDB1) gene, activation of fetal hemoglobin was achieved in vitro, providing a potential therapy for sickle cell disease (37). In another study, re-activation of fetal hemoglobin was achieved by deactivating the enhancer of its repressor B-cell CLL/lymphoma 11A (BCL11A) using CRISPR gene editing (38). Our study provides a novel approach that also takes advantage of cis-regulatory elements for therapeutic purposes. There are numerous diseases that are caused by lower gene dosage that could potentially be treated with CRISPRa therapy. In addition, several human diseases could potentially be rescued by the activation of another gene with a similar function. These could include for example Utrophin for Duchenne Muscular Dystrophy (39), survival of motor neuron 2 (SMA2) for Spinal Muscular Atrophy (SMA; (40)) or the aforementioned fetal globin for sickle cell disease. Further development of this technology could provide a viable therapy for patients inflicted with these diseases.

III. Materials and Methods

Plasmids

The pMSCV-LTR-dCas9-VP64-BFP vector, encoding a mammalian codon-optimized *Streptococcus pyogenes* dCas9 fused to two C-terminal SV40 NLSs and tagBFP along with a VP64 domain and the U6-sgRNA-CMV-mCherry-T2A-Puro plasmids were used for cell line transfections (both kind gifts from Dr. Stanley Qi). sgRNAs were cloned using the In-Fusion HD-cloning kit (Clontech) following the manufacturer's protocol into the BstXI and XhoI sites. Mouse knockin vectors were generated by cloning dCas9-VP64 and U6-sgRNA-CMV-mCherry expression cassettes from the aforementioned vectors into the TARGATT (CAG+Poly A) plasmid (Applied StemCell). pcDNA-dCas9-VP64 (Addgene 47107), and U6-sgRNA-CMV-mCherry-WPREpA were cloned replacing the Ef1a-FAS-hChR2(H134R)-mCherry-WPRE-pA with that of our U6-sgRNA-CMV-mCherry-WPREpA into the backbone of pAAV-Ef1a-FAS-hChR2(H134R)-mCherry-WPRE-pA (Addgene 37090).

AAV Production

AAV DJ serotype particles were produced using the Stanford Neuroscience viral vector core. The packaging load for pCMV-dCas9-VP64 was 5.4 kb and for pU6-Sim1Pr-CMV-mCherry and pU6-SCE2-CMV-mCherry 2.5 kb. Genomic titers were ascertained by WPRE and ITR probes to be $1.40E^{10}$ viral genome (vg)/ml for pCMV-dCas9-VP64 and around $3.30E^{13}$ vg/ml for pU6-Sim1Pr-CMV-mCherry and $2.20 E^{13}$ vg/ml for pU6-SCE2-CMV-mCherry.

Cell Culture

Neuroblastoma 2a cells (Neuro-2a; ATCC® CCL-131) were grown following ATCC guidelines. Plasmids were transfected into Neuro-2a cells using X-tremeGENE HP DNA transfection reagent (Roche) following the manufacturer's protocol. AAV particles were infected into Neuro2a cells at different MOIs. Neuro2a cells were harvested 48 hours post transfection and 5 days post infection to isolate RNA for qRT-PCR analysis.

Human HEK293T cells were grown following ATCC guidelines. Plasmids were transfected into these cells using X-tremeGENE HP DNA transfection reagent (Roche) following the manufacturer's protocol.

Quantitative Reverse-Transcription PCR

RNA was isolated from cells or tissues using RNeasy Mini Kit (Qiagen) following the manufacturer's protocol. For mice, animals were euthanized and tissues were harvested directly into the RNA lysis buffer of the RNeasy Mini Kit. The hypothalamus was dissected using a mouse Brain Matrix and slicers from Zivic Instruments. cDNA was prepared using SuperScript III First-Strand Synthesis System (Invitrogen) using the manufacturer's protocol along with DNaseI digestion. qPCR was performed using SsoFast EvaGreen Supermix (Biorad). The results were expressed as fold-increase mRNA expression of the gene of interest normalized to either beta-actin, Rp138 or Elf3 expression by the $\Delta\Delta CT$ method followed by ANOVA and Tukey test for statistical analysis. Reported values are the mean and standard error of the mean from three independent experiments performed on different days (N=3) with technical duplicates that were averaged for each experiment.

Mice $Sim1^{+/-}$ mice (17) on a mixed genetic background were obtained as a kind gift from Dr. Jacques Michaud lab. In these mice, a 1 kb fragment containing 750 bp of the 5' region, the initiation codon, and the sequence coding for the basic domain (the first 17 amino acids) was replaced by a Pgk-neo cassette, that was used for genotyping using KAPA mouse genotyping kit (KAPA Biosystems). To generate dCas9-VP64 and sgRNA mice we used TARGATT technology (24). DNA for injection was prepared and purified as mini-circles using the TARGATT Transgenic Kit, V6 (Applied StemCell). The injection mix contained 3 ng/µL DNA and 48 ng/µL of in vitro transcribed φC31o mRNA in microinjection TE buffer (0.1 mM EDTA, 10 mM Tris, pH 7.5) and injections were done using standard mouse transgenic protocols (41). dCas9-VP64 was inserted into the mouse Hipp11 locus and sgRNAs into the Rosa26 locus. Mice were genotyped using the using the KAPA mouse genotyping kit. F0 TARGATT knock-ins were assessed using PCR7+8, PCR1 described in (PMID: 21464299) along with vector insertion specific dCas9-VP64 primers as well as mCherry specific primers. All mice were fed ad libitum Picolab mouse diet 20, 5058 containing 20% protein, 9% fat, 4% fibre for whole study. Calories provided by: Protein, % 23.210 Fat (ether extract), % 21.559 Carbohydrates, % 55.231. All animal work was approved by the UCSF Institutional Animal Care and Use Committee.

Mouse Body Weight Measurements.

$H11P^{CAG-dCas9-VP64}$, $ROSA26^{Sim1Pr-sgRNA}$ and $ROSA26^{SCE2En-sgRNA}$ mice were mated with FVB mice for 3-5 generations to assess germline transmission. Three independent integrants were used from each line to set up matings. $H11P^{CAG-dCas9-VP64}$ were mated with $Sim1^{+/-}$ and subsequent $Sim1^{+/-} \times H11P^{CAG-dCas9-VP64}$ mice were rossed with either $ROSA26^{Sim1Pr-sgRNA}$ or $ROSA26^{SCE2En-sgRNA}$ to generate mice having all three unlinked alleles. Mice were maintained at Picodiet 5058 throughout the study and at least 6 females and 6 males from all genotypes (wild-type littermates, $Sim1^{+/-}$, $Sim1^{+/-} \times H11P^{CAG-dCas9-VP64}$, $Sim1^{+/-} \times H11P^{CAG-dCas9-VP64} \times ROSA26^{Sim1Pr-sgRNA}$, $Sim1^{+/-} \times H11P^{CAG-dCas9-VP64} \times ROSA26^{SCE2En-sgRNA}$) were measured for their body weights from 4-16 weeks of age on a weekly basis.

Mouse Metabolic Profiling

Metabolic rates from individual mice were measured using the Columbus Instruments Comprehensive Lab Animal Monitoring System (CLAMS; Columbus Instruments). Mice were single housed and acclimatized on powdered picodiet 5058 for 3-4 days before performing the metabolic monitoring. We individually housed mice in CLAMS units and measurements were carried out over 4-5 days. The temperature was maintained at 22° C. and oxygen and carbon dioxide were calibrated with 'Air reference' set at 20.901 and 0.0049. Three males and three females from each genotype: wild-type littermates, $Sim1^{+/-}$, $Sim1^{+/-} \times H11P^{CAG-dCas9-VP64} \times ROSA26^{Sim1Pr-sgRNA}$; $Sim1^{+/-} \times H11P^{CAG-dCas9-VP64} \times ROSA26^{SCE2En-sgRNA}$ were measured. with metabolic parameter (VCO2, V02, RER, food intake, and activity monitoring). Metabolic data was analyzed using CLAX support software (Columbus Instruments).

Body Composition Analysis

Body composition was measured using either Dual Energy X-ray Absorptiometry (DEXA) or Echo Magnetic Resonance Imaging (EchoMRI; Echo Medical System). For DEXA, mice anesthetized using isoflurane were measured for bone mineral density and tissue composition (fat mass and lean mass) using the Lunar PIXImus. EchoMRI (Echo Medical System) was used to measure whole body composition parameters such as total body fat, lean mass, body fluids, and total body water in live mice without the need for anesthesia or sedation.

Stereotaxic Injections

Four week-old $Sim1^{+/-}$ males or females, weighing between 22 and 26 g, were housed individually in cages for at least 2 days before surgical interventions. Mice were anesthetized with a 100 mg/kg Avertin intraperitoneal injection. The skull was immobilized in a stereotaxic apparatus (David Kopf Instruments). The stereotaxic coordinates for injection into the PVN were 0.80 mm caudal to bregma, 0 mm at the midline, and 5.2 mm below the surface of the skull. A 1.5 mm hole was created in the cranium by circular movements using hand-held Dumont 5-45 tweezers (Fine Science Tools). Using a 31 gauge 1 ul Hamilton microsyringe, we injected a dose of $0.5 \times 10^7$ vg/ml of sgRNA-AAV along with $2.5 \times 10^6$ vg/kg of dCas-VP64-AAV, in a total injection volume of 1 ul per animal into the PVN unilaterally over a 10 minute period. After AAV delivery, the needle was left in place for 20 minutes to prevent reflux and slowly withdrawn in several steps, over 10 minutes. Mice were administered two doses of buprenorphine (100 mg/kg) before and 24 hours post surgery. Immunostaining for mCherry, as described below, was used to validate PVN injection coordinates 2-12 weeks following injection in several mice. Mice were maintained on a picodiet 5058 and weighed on a weekly basis.

Immunostaining

For immunostaining, mice were anesthetized with pentobarbital (7.5 mg/0.15 ml, i.p.) and transcardially perfused with 10 ml of heparinized saline (10 U/ml, 2 ml/min) followed by 10 ml of phosphate-buffered 4% paraformaldehyde (PFA). Brains were removed, postfixed for 24 hours in 4% PFA, and then equilibrated in 30% sucrose in PBS for 72 hours. Brains were coronally sectioned (35 microns for immunostaining, 50 m for stereology) on a sliding microtome (Leica SM 2000R). Immunohistochemistry was performed as previously described (19, 42, 43). Coronal brain sections that had been stored in PBS at 4° C. were permeabilized and blocked in 3% normal goat serum/0.3% Triton X-100 for 1 hour and incubated at 4° C. overnight using an mCherry antibody at a dilution of 1:500 (Abcam ab167453). Sections were placed in 4,6-diamidino-2-phenylindole (DAPI) (0.2 g/ml; 236276; Roche) for 10 minutes and then mounted on plus coated slides and coverslipped using Vectashield (H-1000; Vector Laboratories). Images of sections containing PVN were captured on a Zeiss Apotome.

REFERENCES

1 Dang, V. T., Kassahn, K. S., Marcos, A. E. & Ragan, M. A. Identification of human haploinsufficient genes and their genomic proximity to segmental duplications. *Eur J Hum Genet.* 16, 1350-1357. doi: 1310.1038/ejhg.2008.1111. Epub 28 Jun. 1354. (2008).

2 Huang, N., Lee, I., Marcotte, E. M. & Hurles, M. E. Characterising and predicting haploinsufficiency in the human genome. *PLoS Genet.* 6, e1001154. doi: 1001110.1001371/journal.pgen.1001154. (2010).

3 Lek, M. et al. Analysis of protein-coding genetic variation in 60,706 humans. *Nature.* 536, 285-291. doi: 210.1038/nature19057. (2016).

4 Bender, E. Gene therapy: Industrial strength. *Nature.* 537, S57-59. doi: 10.1038/153751057a. (2016).

5 Kotterman, M. A. & Schaffer, D. V. Engineering adeno-associated viruses for clinical gene therapy. *Nat Rev Genet.* 15, 445-451. doi: 410.1038/nrg3742. Epub 2014 May 1020. (2014).

6 Gilbert, L. A. et al. CRISPR-mediated modular RNA-guided regulation of transcription in eukaryotes. *Cell.* 154, 442-451. doi: 410.1016/j.cell.2013.1006.1044. Epub 213 July 1011. (2013).

7 Perez-Pinera, P. et al. RNA-guided gene activation by CRISPR-Cas9-based transcription factors. *Nat Methods.* 10, 973-976. doi: 910.1038/nmeth.2600. Epub 213 July 1025. (2013).

8 Konermann, S. et al. Genome-scale transcriptional activation by an engineered CRISPR-Cas9 complex. *Nature* (2014).

9 Hilton, I. B. et al. Epigenome editing by a CRISPR-Cas9-based acetyltransferase activates genes from promoters and enhancers. *Nat Biotechnol.* 33, 510-517. doi: 510.1038/nbt.3199. Epub 215 April 1036. (2015).

10 Chavez, A. et al. Highly efficient Cas9-mediated transcriptional programming. *Nat Methods.* 12, 326-328. doi: 310.1038/nmeth.3312. Epub 215 March 1032. (2015).

11 Michaud, J. L., Rosenquist, T., May, N. R. & Fan, C. M. Development of neuroendocrine lineages requires the bHLH-PAS transcription factor SIM1. *Genes Dev* 12, 3264-3275 (1998).

12 Beckers, S., Zegers, D., Van Gaal, L. F. & Van Hul, W. The role of the leptin-melanocortin signalling pathway in the control of food intake. *Crit Rev Eukaryot Gene Expr.* 19, 267-287. (2009).

13 Holder, J. L., Jr., Butte, N. F. & Zinn, A. R. Profound obesity associated with a balanced translocation that disrupts the SIM1 gene. *Hum Mol Genet* 9, 101-108 (2000).

14 Ahituv, N. et al. Medical sequencing at the extremes of human body mass. *Am J Hum Genet.* 80, 779-791. (2007).

15 Ramachandrappa, S. et al. Rare variants in single-minded 1 (SIM1) are associated with severe obesity. *J Clin Invest.* 123, 3042-3050. doi: 3010.1172/JCI68016. Epub 6213 June 68017. (2013).

16 Bonnefond, A. et al. Loss-of-function mutations in SIM1 contribute to obesity and Prader-Willi-like features. *J Clin Invest.* 123, 3037-3041. doi: 3010.1172/JCI68035. Epub 6213 June 68017. (2013).

17 Michaud, J. L. et al. Sim1 haploinsufficiency causes hyperphagia, obesity and reduction of the paraventricular nucleus of the hypothalamus. *Hum Mol Genet* 10, 1465-1473 (2001).

18 Tolson, K. P. et al. Postnatal Sim1 deficiency causes hyperphagic obesity and reduced Mc4r and oxytocin expression. *J* 30, 3803-3812. (2010).

19 Kublaoui, B. M., Holder, J. L., Jr., Tolson, K. P., Gemelli, T. & Zinn, A. R. SIM1 overexpression partially rescues agouti yellow and diet-induced obesity by normalizing food intake. *Endocrinology*. 147, 4542-4549. Epub 2006 May 4518. (2006).

20 Yang, C., Boucher, F., Tremblay, A. & Michaud, J. L. Regulatory interaction between arylhydrocarbon receptor and SIM1, two basic helix-loop-helix PAS proteins involved in the control of food intake. *J Biol Chem*. 279, 9306-9312. Epub 23 December 9301. (2004).

21 Kim, M. J., Oksenberg, N., Hoffmann, T. J., Vaisse, C. & Ahituv, N. Functional characterization of SIM1-associated enhancers. *Hum Mol Genet* (2013).

22 Flint, J. & Shenk, T. Viral transactivating proteins. *Annu Rev Genet*. 31, 177-212. (1997).

23 Chavez, A. et al. Comparison of Cas9 activators in multiple species. *Nat Methods*. 13, 563-567. doi: 510.1038/nmeth.3871. Epub 2016 May 1023. (2016).

24 Tasic, B. et al. Site-specific integrase-mediated transgenesis in mice via pronuclear injection. *Proc Natl Acad Sci USA*. 108, 7902-7907. doi: 7910.1073/pnas.1019507108. Epub 101950211 April 1019507104. (2011).

25 Su, A. I. et al. A gene atlas of the mouse and human protein-encoding transcriptomes. *Proc Natl Acad Sci USA*. 101, 6062-6067. Epub 24 April 6069. (2004).

26 Wu, Z., Yang, H. & Colosi, P. Effect of genome size on AAV vector packaging. *Mol Ther*. 18, 80-86. doi: 10.1038/mt.2009.1255. Epub 29 Nov. 1010. (2010).

27 Zincarelli, C., Soltys, S., Rengo, G. & Rabinowitz, J. E. Analysis of AAV serotypes 1-9 mediated gene expression and tropism in mice after systemic injection. *Mol Ther*. 16, 1073-1080. doi: 1010.1038/mt.2008.1076. Epub 28 Apr. 1015. (2008).

28 Weise, A. et al. Microdeletion and microduplication syndromes. *J Histochem Cytochem*. 60, 346-358. doi: 310.1369/0022155412440001. Epub 002215541244212 March 0022155412440006. (2012).

29 Horlbeck, M. A. et al. Nucleosomes impede Cas9 access to DNA and. *Elife*. 5., e12677. doi: 12610.17554/eLife.12677. (2016).

30 Otchy, T. M. et al. Acute off-target effects of neural circuit manipulations. *Nature*. 528, 358-363. doi: 310.1038/nature16442. Epub 1215 December 16449. (2015).

31 Bondy-Denomy, J., Pawluk, A., Maxwell, K. L. & Davidson, A. R. Bacteriophage genes that inactivate the CRISPR/Cas bacterial immune system. *Nature*. 493, 429-432. doi: 410.1038/nature11723. Epub 1212 December 11716. (2013).

32 Wang, D. et al. Adenovirus-Mediated Somatic Genome Editing of Pten by CRISPR/Cas9 in Mouse Liver in Spite of Cas9-Specific Immune Responses. *Hum Gene Ther*. 26, 432-442. doi: 410.1089/hum.2015.1087. (2015).

33 Chew, W. L. et al. A multifunctional AAV-CRISPR-Cas9 and its host response. *Nat Methods*. 13, 868-874. doi: 810.1038/nmeth.3993. Epub 216 September 1035. (2016).

34 Donsante, A. et al. AAV vector integration sites in mouse hepatocellular carcinoma. *Science*. 317, 477. (2007).

35 Chandler, R. J. et al. Vector design influences hepatic genotoxicity after adeno-associated virus gene therapy. *J Clin Invest*. 125, 870-880. doi: 810.1172/JCI79213. Epub 7215 January 79220. (2015).

36 Nault, J. C. et al. Recurrent AAV2-related insertional mutagenesis in human hepatocellular carcinomas. *Nat Genet*. 47, 1187-1193. doi: 1110.1038/ng.3389. Epub 215 August 1124. (2015).

37 Deng, W. et al. Reactivation of developmentally silenced globin genes by forced chromatin looping. *Cell*. 158, 849-860. doi: 810.1016/j.cell.2014.1005.1050. (2014).

38 Canver, M. C. et al. BCL11A enhancer dissection by Cas9-mediated in situ saturating mutagenesis. *Nature*. 527, 192-197. doi: 110.1038/nature15521. Epub 1215 September 15516. (2015).

39 Hirst, R. C., McCullagh, K. J. & Davies, K. E. Utrophin upregulation in Duchenne muscular dystrophy. *Acta Myol*. 24, 209-216. (2005).

40 Sproule, D. M. & Kaufmann, P. Therapeutic developments in spinal muscular atrophy. *Ther Adv Neurol Disord*. 3, 173-185. doi: 110.1177/1756285610369026. (2010).

41 Nagy, A., Gertsenstein, M., Vintersten, K. & Behringer, R. *Manipulating the mouse embryo: A laboratory manual.* 3rd edition edn, (Cold Spring Harbor, 2002).

42 Beuckmann, C. T. et al. Expression of a poly-glutamine-ataxin-3 transgene in orexin neurons induces narcolepsy-cataplexy in the rat. *J Neurosci*. 24, 4469-4477. (2004).

43 Kublaoui, B. M., Gemelli, T., Tolson, K. P., Wang, Y. & Zinn, A. R. Oxytocin deficiency mediates hyperphagic obesity of Sim1 haploinsufficient mice. *Mol Endocrinol*. 22, 1723-1734. doi: 1710.1210/me.2008-0067. Epub 2008 May 1721. (2008).

Although the foregoing invention has been described in some detail by way of illustration and example for purposes of clarity of understanding, one of skill in the art will appreciate that certain changes and modifications may be practiced within the scope of the appended claims. All patents, patent applications, and other publications, including GenBank Accession Numbers, Entrez Gene IDs, and publications referred to by pubmed ID (PMID), cited in this application are incorporated by reference in the entirety for all purposes.

What is claimed is:

1. A composition comprising an adeno-associated viral vector comprising a nucleic acid encoding a guide RNA, wherein the guide RNA comprises:
   a) a targeting region that, under conditions present in a nucleus of a cell, specifically hybridizes to a promoter region or an enhancer region operably linked to a wild-type copy of a haploinsufficient gene; and
   b) a binding region that specifically binds a catalytically inactive CRISPR nuclease under conditions present in the nucleus of the cell, wherein the haploinsufficient gene is SCN2A, SIM1, or MC4R.

2. The composition of claim 1, wherein the catalytically inactive CRISPR nuclease comprises (i) a nuclease domain that has been modified to eliminate nuclease and nicking activity and (ii) a transcriptional activation domain, and/or a D10A, H840A *S. pyogenes* dCas9.

3. The composition of claim 1, wherein the catalytically inactive CRISPR nuclease is a catalytically inactive CRISPR nuclease-VP64 fusion polypeptide.

4. The composition of claim 1, wherein the cell is a non-dividing cell, a neuron, or a hypothalamus cell.

5. The composition of claim 1, further comprising one or more plasmids encoding AAV rep and cap genes.

6. The composition of claim 1, further comprising one or more plasmids encoding adenovirus helper factors E1A, E1B, E2A, E4ORF6, and/or VA.

* * * * *

SEQUENCE LISTING

```
Sequence total quantity: 95
SEQ ID NO: 1          moltype = DNA   length = 20
FEATURE               Location/Qualifiers
misc_feature          1..20
                      note = Synthetic construct
source                1..20
                      mol_type = other DNA
                      organism = synthetic construct
```

```
SEQUENCE: 1
gacacggaat tcattgccag                                                    20

SEQ ID NO: 2            moltype = DNA  length = 20
FEATURE                 Location/Qualifiers
misc_feature            1..20
                        note = Synthetic construct
source                  1..20
                        mol_type = other DNA
                        organism = synthetic construct
SEQUENCE: 2
ctgcgggtta ggtctaccgg                                                    20

SEQ ID NO: 3            moltype = DNA  length = 20
FEATURE                 Location/Qualifiers
misc_feature            1..20
                        note = Synthetic construct
source                  1..20
                        mol_type = other DNA
                        organism = synthetic construct
SEQUENCE: 3
gttgagcgct cagtccagcg                                                    20

SEQ ID NO: 4            moltype = DNA  length = 20
FEATURE                 Location/Qualifiers
misc_feature            1..20
                        note = Synthetic construct
source                  1..20
                        mol_type = other DNA
                        organism = synthetic construct
SEQUENCE: 4
tcccgacgtc gtgcgcgacc                                                    20

SEQ ID NO: 5            moltype = DNA  length = 20
FEATURE                 Location/Qualifiers
misc_feature            1..20
                        note = Synthetic construct
source                  1..20
                        mol_type = other DNA
                        organism = synthetic construct
SEQUENCE: 5
gctctgaatc ttactacccg                                                    20

SEQ ID NO: 6            moltype = DNA  length = 20
FEATURE                 Location/Qualifiers
misc_feature            1..20
                        note = Synthetic construct
source                  1..20
                        mol_type = other DNA
                        organism = synthetic construct
SEQUENCE: 6
gctgttaact aaagacaggg                                                    20

SEQ ID NO: 7            moltype = DNA  length = 20
FEATURE                 Location/Qualifiers
misc_feature            1..20
                        note = Synthetic construct
source                  1..20
                        mol_type = other DNA
                        organism = synthetic construct
SEQUENCE: 7
gtggtctggg tgatctcatg                                                    20

SEQ ID NO: 8            moltype = DNA  length = 21
FEATURE                 Location/Qualifiers
misc_feature            1..21
                        note = Synthetic construct
source                  1..21
                        mol_type = other DNA
                        organism = synthetic construct
SEQUENCE: 8
gacaaaggaa catctgagag g                                                  21

SEQ ID NO: 9            moltype = DNA  length = 20
FEATURE                 Location/Qualifiers
misc_feature            1..20
                        note = Synthetic construct
source                  1..20
                        mol_type = other DNA
```

```
                            -continued organism = synthetic construct
SEQUENCE: 9
gtgatctcat ggggaagagg                                              20

SEQ ID NO: 11            moltype = DNA  length = 20
FEATURE                  Location/Qualifiers
misc_feature             1..20
                         note = Synthetic construct
source                   1..20
                         mol_type = other DNA
                         organism = synthetic construct
SEQUENCE: 10
ggctttgatc gtggtctggg                                              20

SEQ ID NO: 11            moltype = DNA  length = 20
FEATURE                  Location/Qualifiers
misc_feature             1..20
                         note = Synthetic construct
source                   1..20
                         mol_type = other DNA
                         organism = synthetic construct
SEQUENCE: 11
gcgagcccag tcgcgtgggg                                              20

SEQ ID NO: 12            moltype = DNA  length = 20
FEATURE                  Location/Qualifiers
misc_feature             1..20
                         note = Synthetic construct
source                   1..20
                         mol_type = other DNA
                         organism = synthetic construct
SEQUENCE: 12
gccaagaatt ggccaaaggg                                              20

SEQ ID NO: 13            moltype = AA  length = 159
FEATURE                  Location/Qualifiers
source                   1..159
                         mol_type = protein
                         organism = Homo sapiens
SEQUENCE: 13
EKCLSVACLD KNELSDHLDA MDSNLDNLQT MLSSHGFSVD TSALLDLFSP SVTVPDMSLP    60
DLDSSLASIQ ELLSPQEPPR PPEAENSSPD SGKQLVHYTA QPLFLLDPGS VDTGSNDLPV   120
LFELGEGSYF SEGDGFAEDP TISLLTGSEP PKAKDPTVS                          159

SEQ ID NO: 14            moltype = AA  length = 11
FEATURE                  Location/Qualifiers
REGION                   1..11
                         note = Herpes simplex virus
source                   1..11
                         mol_type = protein
                         organism = unidentified
SEQUENCE: 14
DALDDFDLDM L                                                        11

SEQ ID NO: 15            moltype = AA  length = 50
FEATURE                  Location/Qualifiers
REGION                   1..50
                         note = Synthetic construct
source                   1..50
                         mol_type = protein
                         organism = synthetic construct
SEQUENCE: 15
DALDDFDLDM LGSDALDDFD LDMLGSDALD DFDLDMLGSD ALDDFDLDML              50

SEQ ID NO: 16            moltype = AA  length = 261
FEATURE                  Location/Qualifiers
source                   1..261
                         mol_type = protein
                         organism = Homo sapiens
SEQUENCE: 16
SQYLPDTDDR HRIEEKRKRT YETFKSIMKK SPFSGPTDPR PPPRRIAVPS RSSASVPKPA    60
PQPYPFTSSL STINYDEFPT MVFPSGQISQ ASALAPAPPQ VLPQAPAPAP APAMVSALAQ   120
APAPVPVLAP GPPQAVAPPA PKPTQAGEGT LSEALLQLQF DDEDLGALLG NSTDPAVFTD   180
LASVDNSEFQ QLLNQGIPVA PHTTEPMLME YPEAITRLVT GAQRPPDPAP APLGAPGLPN   240
GLLSGDEDFS SIADMDFSAL L                                             261

SEQ ID NO: 17            moltype = AA  length = 318
FEATURE                  Location/Qualifiers
source                   1..318
```

```
                        mol_type = protein
                        organism = Mus musculus
SEQUENCE: 17
MELLSPPLRD IDLTGPDGSL CSFETADDFY DDPCFDSPDL RFFEDLDPRL VHMGALLKPE    60
EHAHFPTAVH PGPGAREDEH VRAPSGHHQA GRCLLWACKA CKRKTTNADR RKAATMRERR   120
RLSKVNEAFE TLKRCTSSNP NQRLPKVEIL RNAIRYIEGL QALLRDQDAA PPGAAAFYAP   180
GPLPPGRGSE HYSGDSDASS PRSNCSDGMM DYSGPPSGPR RQNGYDTAYY SEAARESRPG   240
KSAAVSSLDC LSSIVERIST DSPAAPALLL ADAPPESPPG PPEGASLSDT EQGTQTPSPD   300
AAPQCPAGSN PNAIYQVL                                                 318

SEQ ID NO: 18           moltype = AA  length = 190
FEATURE                 Location/Qualifiers
REGION                  1..190
                        note = Epstein-Barr virus
source                  1..190
                        mol_type = protein
                        organism = unidentified
SEQUENCE: 18
RDSREGMFLP KPEAGSAISD VFEGREVCQP KRIRPFHPPG SPWANRPLPA SLAPTPTGPV    60
HEPVGSLTPA PVPQPLDPAP AVTPEASHLL EDPDEETSQA VKALREMADT VIPQKEEAAI   120
CGQMDLSHPP PRGHLDELTT TLESMTEDLN LDSPLTPELN EILDTFLNDE CLLHAMHIST   180
GLSIFDTSLF                                                          190

SEQ ID NO: 19           moltype = AA  length = 366
FEATURE                 Location/Qualifiers
source                  1..366
                        mol_type = protein
                        organism = Homo sapiens
SEQUENCE: 19
MDSDDEMVEE AVEGHLDDDG LPHGFCTVTY SSTDRFEGNF VHGEKNGRGK FFFFDGSTLE    60
GYYVDDALQG QGVYTYEDGG VLQGTYVDGE LNGPAQEYDT DGRLIFKGQY KDNIRHGVCW   120
IYYPDGGSLV GEVNEDGEMT GEKIAYVYPD ERTALYGKPI DGEMIEGKLA TLMSTEEGRP   180
HFELMPGNSV YHFDKSTSSC ISTNALLPDP YESERVYVAE SLISSAGEGL FSKVAVGPNT   240
VMSFYNGVRI THQEVDSRDW ALNGNTLSLD EETVIDVPEP YNHVSKYCAS LGHKANHSFT   300
PNCIYDMFVH PRFGPIKCIR TLRAVEADEE LTVAYGYDHS PPGKSGPEAP EWYQVELKAF   360
QATQQK                                                              366

SEQ ID NO: 20           moltype = AA  length = 531
FEATURE                 Location/Qualifiers
REGION                  1..531
                        note = Synthetic construct
source                  1..531
                        mol_type = protein
                        organism = synthetic construct
SEQUENCE: 20
EASGSGRADA LDDFDLDMLG SDALDDFDLD MLGSDALDDF DLDMLGSDAL DDFDLDMLIN    60
SRSSGSPKKK RKVGSQYLPD TDDRHRIEEK RKRTYETFKS IMKKSPFSGP TDPRPPPRRI   120
AVPSRSSASV PKPAPQPYPF TSSLSTINYD EFPTMVFPSG QISQASALAP APPQVLPQAP   180
APAPAPAMVS ALAQAPAPVP VLAPGPPQAV APPAPKPTQA GEGTLSEALL QLQFDDEDLG   240
ALLGNSTDPA VFTDLASVDN SEFQQLLNQG IPVAPHTTEP MLMEYPEAIT RLVTGAQRPP   300
DPAPAPLGAP GLPNGLLSGD EDFSSIADMD FSALLGSGSG SRDSREGMFL PKPEAGSAIS   360
DVFEGREVCQ PKRIRPFHPP GSPWANRPLP ASLAPTPTGP VHEPVGSLTP APVPQPLDPA   420
PAVTPEASHL LEDPDEETSQ AVKALREMAD TVIPQKEEAA ICGQMDLSHP PPRGHLDELT   480
TTLESMTEDL NLDSPLTPEL NEILDTFLND ECLLHAMHIS TGLSIFDTSL F            531

SEQ ID NO: 21           moltype = AA  length = 377
FEATURE                 Location/Qualifiers
source                  1..377
                        mol_type = protein
                        organism = Homo sapiens
SEQUENCE: 21
KFSAKRLPST RLGTFLENRV NDFLRRQNHP ESGEVTVRVV HASDKTVEVK PGMKARFVDS    60
GEMAESFPYR TKALFAFEEI DGVDLCFFGM HVQEYGSDCP PPNQRRVYIS YLDSVHFFRP   120
KCLRTAVYHE ILIGYLEYVK KLGYTTGHIW ACPPSEGDDY IFHCHPPDQK IPKPKRLQEW   180
YKKMLDKAVS ERIVHDYKDI FKQATEDRLT SAKELPYFEG DFWPNVLEES IKELEQEEEE   240
RKREENTSNE STDVTKGDSK NAKKKNNKKT SKNKSSLSRG NKKKPGMPNV SNDLSQKLYA   300
TMEKHKEVFF VIRLIAGPAA NSLPPIVDPD PLIPCDLMDG RDAFLTLARD KHLEFSSLRR   360
AQWSTMCMLV ELHTQSQ                                                  377

SEQ ID NO: 22           moltype = AA  length = 2136
FEATURE                 Location/Qualifiers
source                  1..2136
                        mol_type = protein
                        organism = Homo sapiens
SEQUENCE: 22
MSRSRHARPS RLVRKEDVNK KKNSQLRKT TKGANKNVAS VKTLSPGKLK QLIQERDVKK     60
KTEPKPPVPV RSLLTRAGAA RMNLDRTEVL FQNPESLTCN GFTMALRSTS LSRRLSQPPL   120
VVAKSKKVPL SKGLEKQHDC DYKILPALGV KHSENDSVPM QDTQVLPDIE TLIGVQNPSL   180
LKGKSQETTQ FWSQRVEDSK INIPTHSGPA AEILPGPLEG TRCGEGLFSE ETLNDTSGSP   240
```

```
KMFAQDTVCA PFPQRATPKV TSQGNPSIQL EELGSRVESL KLSDSYLDPI KSEHDCYPTS   300
SLNKVIPDLN LRNCLALGGS TSPTSVIKFL LAGSKQATLG AKPDHQEAFE ATANQQEVSD   360
TTSFLGQAFG AIPHQWELPG ADPVHGEALG ETPDLPEIPG AIPVQGEVFG TILDQQETLG   420
MSGSVVPDLP VFLPVPPNPI ATFNAPSKWP EPQSTVSYGL AVQGAIQILP LGSGHTPQSS   480
SNSEKNSLPP VMAISNVENE KQVHISFLPA NTQGFPLAPE RGLFHASLGI AQLSQAGPSK   540
SDRGSSQVSV TSTVHVVNTT VVTMPVPMVS TSSSSYTTLL PTLEKKKRKR CGVCEPCQQK   600
TNCGECTYCK NRKNSHQICK KRKCEELKKK PSVVVPLEVI KENKRPQREK KPKVLKADFD   660
NKPVNGPKSE SMDYSRCGHG EEQKLELNPH TVENVTKNED SMTGIEVEKW TQNKKSQLTD   720
HVKGDFSANV PEAEKSKNSE VDKKRTKSPK LFVQTVRNGI KHVHCLPAET NVSFKKFNIE   780
EFGKTLENNS YKFLKDTANH KNAMSSVATD MSCDHLKGRS NVLVFQQPGF NCSSIPHSSH   840
SIINHHASIH NEGDQPKTPE NIPSKEPKDG SPVQPSLLSL MKDRRLTEQ VVAIEALTQL    900
SEAPSENSSP SKSEKDEESE QRTASLLNSC KAILYTVRKD LQDPNLQGEP PKLNHCPSLE   960
KQSSCNTVVF NGQTTTLSNS HINSATNQAS TKSHEYSKVT NSLSLFIPKS NSSKIDTNKS  1020
IAQGIITLDN CSNDLHQLPP RNNEVEYCNQ LLDSSKKLDS DDLSCQDATH TQIEEDVATQ  1080
LTQLASIIKI NYIKPEDKKV ESTPTSLVTC NVQQKYNQEK GTIQQKPPSS VHNNHGSSLT  1140
KQKNPTQKKT KSTPSRDRRK KKPTVVSYQE NDRQKWEKLS YMYGTICDIW IASKFQNFGQ  1200
FCPHDFPTVF GKISSSTKIW KPLAQTRSIM QPKTVFPPLT QIKLQRYPES AEEKVKVEPL  1260
DSLSLFHLKT ESNGKAFTDK AYNSQVQLTV NANQKAHPLT QPSSPPNQCA NVMAGDDQIR  1320
FQQVVKEQLM HQRLPTLPGI SHETPLPESA LTLRNVNVVC SGGITVVSTK SEEEVCSSSF  1380
GTSEFSTVDS AQKNFNDYAM NFFTNPTKNL VSITKDSELP TCSCLDRVIQ KDKGPYYTHL  1440
GAGPSVAAVR EIMENRYGQK GNAIRIEIVV YTGKEGKSSH GCPIAKWVLR RSSDEEKVLC  1500
LVRQRTGHHC PTAVMVVLIM VWDGIPLPMA DRLYTELTEN LKSYNGHPTD RRCTLNENRT  1560
CTCQGIDPET CGASFSFGCS WSMYFNGCKF GRSPSPRRFR IDPSSPLHEK NLEDNLQSLA  1620
TRLAPIYKQY APVAYQNQVE YENVARECRL GSKEGRPFSG VTACLDFCAH PHRDIHNMNN  1680
GSTVVCTLTR EDNRSLGVIP QDEQLHVLPL YKLSDTDEFG SKEGMEAKIK SGAIEVLAPR  1740
RKKRTCFTQP VPRSGKKRAA MMTEVLAHKI RAVEKKPIPR IKRKNNSTTT NNSKPSSLPT  1800
LGSNTETVQP EVKSETEPHF ILKSSDNTKT YSLMPSAPHP VKEASPGFSW SPKTASATPA  1860
PLKNDATASC GFSERSSTPH CTMPSGRLSG ANAAAADGPG ISQLGEVAPL PTLSAPVMEP  1920
LINSEPSTGV TEPLTPHQPN HQPSFLTSPQ DLASSPMEED EQHSEADEPP SDEPLSDDPL  1980
SPAEEKLPHI DEYWSDSEHI FLDANIGGVA IAPAHGSVLI ECARRELHAT TPVEHPNRNH  2040
PTRLSLVFYQ HKNLNKPQHG FELNKIKFEA KEAKNKKMKA SEQKDQAANE GPEQSSEVNE  2100
LNQIPSHKAL TLTHDNVVTV SPYALTHVAG PYNHWV                           2136

SEQ ID NO: 23          moltype = AA  length = 552
FEATURE                Location/Qualifiers
source                 1..552
                       mol_type = protein
                       organism = Mus musculus
SEQUENCE: 23
GMDVTLLEAR DRVGGRVATF RKGNYVADLG AMVVTGLGGN PMAVVSKQVN MELAKIKQKC    60
PLYEANGQAV PKEKDEMVEQ EFNRLLEATS YLSHQLDFNV LNNKPVSLGQ ALEVVIQLQE   120
KHVKDEQIEH WKKIVKTQEE LKELLNKMVN LKEKIKELHQ QYKEASEVKP PRDITAEFLV   180
KSKHRDLTAL CKEYDELAET QGKLEEKLQE LEANPPSDVY LSSRDRQILD WHFANLEFAN   240
ATPLSTLSLK HWDQDDDFEF TGSHLTVRNG YSCVPVALAE GLDIKLNTAV RQVRYTASGC   300
EVIAVNTRST SQTFIYKCDA VLCTLPLGVL KQQPPAVQFV PPLPEWKTSA VQRMGFGNLN   360
KVVLCFDRVF WDPSVNLFGH VGSTTASRGE LFLFWNLYKA PILLALVAGE AAGIMENISD   420
DVIVGRCLAI LKGIFGSSAV PQPKETVVSR WRADPWARGS YSYVAAGSSG NDYDLMAQPI   480
TPGPSIPGAP QPIPRLFFAG EHTIRNYPAT VHGALLSGLR EAGRIADQFL GAMYTLPRQA   540
TPGVPAQQSP SM                                                       552

SEQ ID NO: 24          moltype = AA  length = 191
FEATURE                Location/Qualifiers
source                 1..191
                       mol_type = protein
                       organism = Homo sapiens
SEQUENCE: 24
MGGSGSRLSK ELLAEYQDLT FLTKQEILLA HRRFCELLPQ EQRSVESSLR AQVPFEQILS    60
LPELKANPFK ERICRVFSTS PAKDSLSFED FLDLLSVFSD TATPDIKSHY AFRIFDFDDD   120
GTLNREDLSR LVNCLTGEGE DTRLSASEMK QLIDNILEES DIDRDGTINL SEFQHVISRS   180
PDFASSFKIV L                                                        191

SEQ ID NO: 25          moltype = AA  length = 654
FEATURE                Location/Qualifiers
source                 1..654
                       mol_type = protein
                       organism = Homo sapiens
SEQUENCE: 25
MNQPQRMAPV GTDKELSDLL DFSMMFPLPV TNGKGRPASL AGAQFGGSGL EDRPSSGSWG    60
SGDQSSSSFD PSRTFSEGTH FTESHSSLSS STFLGPGLGG KSGERGAYAS FGRDAGVGGL   120
TQAGFLSGEL ALNSPGPLSP SGMKGTSQYY PSYSGSSRRR AADGSLDTQP KKVRKVPPGL   180
PSSVYPPSSG EDYGRDATAY PSAKTPSSTY PAPFYVADGS LHPSAELWSP PGQAGFGPML   240
GGGSSPLPLP PGSGPVGSSG SSSTFGGLHQ HERMGYQLHG AEVNGGLPSA SSFSSAPGAT   300
YGGVSSHTPP VSGADSLLGS RGTTAGSSGD ALGKALASIY SPDHSSNNFS SSPSTPVGSP   360
QGLAGTSQWP RAGAPGALSP SYDGGLHGLQ SKIEDHLDEA IHVLRSHAVG TAGDMHTLLP   420
GHGALASGFT GPMSLGGRHA GLVGGSHPED GLAGSTSLMH NHAALPSQPG TLPDLSRPPD   480
SYSGLGRAGA TAAASEIKRE EKEDEENTSA ADHSEEEKKE LKAPRARTSP DEDEDDLLPP   540
EQKAERERER RVANNARERL RVRDINEAFK ELGRMCQLHL NSEKPQTKLL ILHQAVSVIL   600
NLEQQVRERN LNPKAACLKR REEEKVSGVV GDPQMVLSAP HPGLSEAHNP AGHM          654
```

```
SEQ ID NO: 26            moltype = AA  length = 1663
FEATURE                  Location/Qualifiers
source                   1..1663
                         mol_type = protein
                         organism = Homo sapiens
SEQUENCE: 26
MGPTSGPSLL LLLLTHLPLA LGSPMYSIIT PNILRLESEE TMVLEAHDAQ GDVPVTVTVH   60
DFPGKKLVLS SEKTVLTPAT NHMGNVTFTI PANREFKSEK GRNKFVTVQA TFGTQVVEKV  120
VLVSLQSGYL FIQTDKTIYT PGSTVLYRIF TVNHKLLPVG RTVMVNIENP EGIPVKQDSL  180
SSQNQLGVLP LSWDIPELVN MGQWKIRAYY ENSPQQVFST EFEVKEYVLP SFEVIVEPTE  240
KFYYIYNEKG LEVTITARFL YGKKVEGTAF VIFGIQDGEQ RISLPESLKR IPIEDGSGEV  300
VLSRKVLLDG VQNPRAEDLV GKSLYVSATV ILHSGSDMVQ AERSGIPIVT SPYQIHFTKT  360
PKYFKPGMPF DLMVFVTNPD GSPAYRVPVA VQGEDTVQSL TQGDGVAKLS INTHPSQKPL  420
SITVRTKKQE LSEAEQATRT MQALPYSTVG NSNNYLHLSV LRTELRPGET LNVNFLLRMD  480
RAHEAKIRYY TYLIMNKGRL LKAGRQVREP GQDLVVLPLS ITTDFIPSFR LVAYYTLIGA  540
SGQREVVADS VWVDVKDSCV GSLVVKSGQS EDRQPVPGQQ MTLKIEGDHG ARVVLVAVDK  600
GVFVLNKKNK LTQSKIWDVV EKADIGCTPG SGKDYAGVFS DAGLTFTSSS GQQTAQRAEL  660
QCPQPAARRR RSVQLTEKRM DKVGKYPKEL RKCCEDGMRE NPMRFSCQRR TRFISLGEAC  720
KKVFLDCCNY ITELRRQHAR ASHLGLARSN LDEDIIAEEN IVSRSEFPES WLWNVEDLKE  780
PPKNGISTKL MNIFLKDSIT TWEILAVSMS DKKGICVADP FEVTVMQDFF IDLRLPYSVV  840
RNEQVEIRAV LYNYRQNEL KVRVELLHNP AFCSLATTKR RHQQTVTIPP KSSLSVPYVI   900
VPLKTGLQEV EVKAAVYHHF ISDGVRKSLK VVPEGIRMNK TVAVRTLDPE RLGREGVQKE  960
DIPPADLSDQ VPDTESETRI LLQGTPVAQM TEDAVDAERL KHLIVTPSGC GEQNMIGMTP 1020
TVIAVHYLDE TEQWEKFGLE KRQGALELIK KGYTQQLAFR QPSSAFAAFV KRAPSTWLTA 1080
YVVKVFSLAV NLIAIDSQVL CGAVKWLILE KQKPDGVFQE DAPVIHQEMI GGLRNNEKD  1140
MALTAFVLIS LQEAKDICEE QVNSLPGSIT KAGDFLEANY MNLQRSYTVA IAGYALAQMG 1200
RLKGPLLNKF LTTAKDKNRW EDPGKQLYNV EATSYALLAL LQLKDFDFVP PVVRWLNEQR 1260
YYGGGYGSTQ ATFMVFQALA QYQKDAPDHQ ELNLDVSLQL PSRSSKITHR IHWESASLLR 1320
SEETKENEGF TVTAEGKGQG TLSVVTMYHA KAKDQLTCNK FDLKVTIKPA PETEKRPQDA 1380
KNTMILEICT RYRGDQDATM SILDISMMTG FAPDTDDLKQ LANGVDRYIS KYELDKAFSD 1440
RNTLIIYLDK VSHSEDDCLA FKVHQYFNVE LIQPGAVKVY AYYNLEESCT RFYHPEKEDG 1500
KLNKLCRDEL CRCAEENCFI QKSDDKVTLE ERLDKACEPG VDYVYKTRLV KVQLSNDFDE 1560
YIMAIEQTIK SGSDEVQVGQ QRTFISPIKC REALKLEEKK HYLMWGLSSD FWGEKPNLSY 1620
IIGKDTWVEH WPEEDECQDE ENQKQCQDLG AFTESMVVFG CPN                  1663

SEQ ID NO: 27            moltype = AA  length = 442
FEATURE                  Location/Qualifiers
source                   1..442
                         mol_type = protein
                         organism = Homo sapiens
SEQUENCE: 27
MYQSLAMAAN HGPPPGAYEA GGPGAFMHGA GAASSPVYVP TPRVPSSVLG LSYLQGGGAG   60
SASGGASGGS SGGAASGAGP GTQQGSPGWS QAGADGAAYT PPPVSPRFSF PGTTGSLAAA  120
AAAAAAREAA AYSSGGGAAG AGLAGREQYG RAGFAGSYSS PYPAYMADVG ASWAAAAAAS  180
AGPFDSPVLH SLPGRANPAA RHPNLDMFDD FSEGRECVNC GAMSTPLWRR DGTGHYLCNA  240
CGLYHKMNGI NRPLIKPQRR LSASRRVGLS CANCQTTTTT LWRRNAEGEP VCNACGLYMK  300
LHGVPRPLAM RKEGIQTRKR KPKNLNKSKT PAAPSGSESL PPASGASSNS SNATTSSSEE  360
MRPIKTEPGL SSHYGHSSSV SQTFSVSAMS GHPSIHPVL SALKLSPQGY ASPVSQSPQT   420
SSKQDSWNSL VLADSHGDII TA                                         442

SEQ ID NO: 28            moltype = AA  length = 393
FEATURE                  Location/Qualifiers
source                   1..393
                         mol_type = protein
                         organism = Homo sapiens
SEQUENCE: 28
MEEPQSDPSV EPPLSQETFS DLWKLLPENN VLSPLPSQAM DDLMLSPDDI EQWFTEDPGP   60
DEAPRMPEAA PPVAPAPAAP TPAAPAPAPS WPLSSSVPSQ KTYQGSYGFR LGFLHSGTAK  120
SVTCTYSPAL NKMFCQLAKT CPVQLWVDST PPPGTRVRAM AIYKQSQHMT EVVRRCPHHE  180
RCSDSDGLAP PQHLIRVEGN LRVEYLDDRN TFRHSVVVPY EPPEVGSDCT TIHYNMCNS   240
SCMGGMNRRP ILTIITLEDS SGNLLGRNSF EVRVCACPGR DRRTEEENLR KKGEPHHELP  300
PGSTKRALPN NTSSSPQPKK KPLDGEYFTL QIRGRERFEM FRELNEALEL KDAQAGKEPG  360
GSRAHSSHLK SKKGQSTSRH KKLMFKTEGP DSD                              393

SEQ ID NO: 29            moltype = AA  length = 785
FEATURE                  Location/Qualifiers
source                   1..785
                         mol_type = protein
                         organism = Homo sapiens
SEQUENCE: 29
MSDQDHSMDE MTAVVKIEKG VGGNNGGNGN GGGAFSQARS SSTGSSSSTG GGGQESQPSP   60
LALLAATCSR IESPNENSNN SQGPSQSGGT GELDLTATQL SQGANGWQII SSSSGATPTS  120
KEQSGSSTNG SNGSESSKNR TVSGGQYVVA AAPNLQNQQV LTGLPGVMPN IQYQVIPQFQ  180
TVDGQQLQFA ATGAQVQQDG SGQIQIIPGA NQQIITNRGS GGNIIAAMPN LQQQAVPLQQ  240
LANNVLSGQT QYVTNVPVAL NGNITLLPVN SVSAATLTPS SQAVTISSSG SQESGSQPVT  300
SGTTISSASL VSSQASSSSF FTNANSYSTT TTTSNMGIMN FTTSGSSGTN SQGQTPQRVS  360
GLQGSDALNI QQNQTSGGSL QAGQQKEGEQ NQQTQQQQIL IQPQLVQGGQ ALQALQAAPL  420
SGQTFTTQAI SQETLQNLQL QAVPNSGPII IRTPTVGPNG QVSWQTLQLQ NLQVQNPQAQ  480
TITLAPMQGV SLGQTSSSNT TLTPIASAAS IPAGTVTVNA AQLSSMPGLQ TINLSALGTS  540
```

```
GIQVHPIQGL PLAIANAPGD HGAQLGLHGA GGDIHDDTA GGEEGENSPD AQPQAGRRTR    600
REACTCPYCK DSEGRGSGDP GKKKQHICHI QGCGKVYGKT SHLRAHLRWH TGERPFMCTW    660
SYCGKRFTRS DELQRHKRTH TGEKKFACPE CPKRFMRSDH LSKHIKTHQN KKGGPGVALS    720
VGTLPLDSGA GSEGSGTATP SALITTNMVA MEAICPEGIA RLANSGINVM QVADLQSINI    780
SGNGF                                                                785

SEQ ID NO: 30           moltype = AA  length = 473
FEATURE                 Location/Qualifiers
source                  1..473
                        mol_type = protein
                        organism = Homo sapiens
SEQUENCE: 30
MGRKKIQITR IMDERNRQVT FTKRKFGLMK KAYELSVLCD CEIALIIFNS TNKLFQYAST     60
DMDKVLLKYT EYNEPHESRT NSDIVETLRK KGLNGCDSPD PDADDSVGHS PESEDKYRKI    120
NEDIDLMISR QRLCAVPPPN FEMPVSIPVS SHNSLVYSNP VSSLGNPNLL PLAHPSLQRN    180
SMSPGVTHRP PSAGNTGGLM GGDLTSGAGT SAGNGYGNPR NSPGLLVSPG NLNKNMQAKS    240
PPPMNLGMNN RKPDLRVLIP PGSKNTMPSV SEDVDLLLNQ RINNSQSAQS LATPVVSVAT    300
PTLPGQGMGG YPSAISTTYG TEYSLSSADL SSLSGFNTAS ALHLGSVTGW QQQHLHNMPP    360
SALSQLGACT STHLSQSSNL SLPSTQSLNI KSEPVSPPRD RTTTPSRYPQ HTRHEAGRSP    420
VDSLSSCSSS YDGSDREDHR NEFHSPIGLT RPSPDERESP SVKRMRLSEG WAT           473
```

```
SEQ ID NO: 31           moltype = AA  length = 353
FEATURE                 Location/Qualifiers
REGION                  1..353
                        note = Human T-lymphotrophic virus
source                  1..353
                        mol_type = protein
                        organism = unidentified
SEQUENCE: 31
MAHFPGFGQS LLFGYPVYVF GDCVQGDWCP ISGGLCSARL HRHALLATCP EHQITWDPID     60
GRVIGSALQF LIPRLPSFPT QRTSKTLKVL TPPITHTTPN IPPSFLQAMR KYSPFRNGYM    120
EPTLGQHLPT LSFPDDGLRP QNLYTLWGGS VVCMYLYQLS PPITWPLLPH VIFCHPGQLG    180
AFLTNVPYKR IEELLYKISL TTGALIILPE DCLPTTLFQP ARAPVTLTAW QNGLLPFHST    240
LTTPGLIWTF TDGTPMISGP CPKDGQPSLV LQSSSFIPHK FQTKAYHPSF LLSHGLIQYS    300
SFHSLHLLFE EYTNIPISLL FNEKEADDND HEPQISPGGL EPPSEKHFRE TEV           353
```

```
SEQ ID NO: 32           moltype = AA  length = 505
FEATURE                 Location/Qualifiers
source                  1..505
                        mol_type = protein
                        organism = Homo sapiens
SEQUENCE: 32
MGETLGDSPI DPESDSFTDT LSANISQEMT MVDTEMPFWP TNFGISSVDL SVMEDHSHSF     60
DIKPFTTVDF SSISTPHYED IPFTRTDPVV ADYKYDLKLQ EYQSAIKVEP ASPPYYSEKT    120
QLYNKPHEEP SNSLMAIECR VCGDKASGFH YGVHACEGCK GFFRRTIRLK LIYDRCDLNC    180
RIHKKSRNKC QYCRFQKCLA VGMSHNAIRF GRMPQAEKEK LLAEISSDID QLNPESADLR    240
ALAKHLYDSY IKSFPLTKAK ARAILTGKTT DKSPFVIYDM NSLMMGEDKI KFKHITPLQE    300
QSKEVAIRIF QGCQFRSVEA VQEITEYAKS IPGFVNLDLN DQVTLLKYGV HEIIYTMLAS    360
LMNKDGVLIS EGQGFMTREF LKSLRKPFGD FMEPKFEFAV KFNALELDDS DLAIFIAVII    420
LSGDRPGLLN VKPIEDIQDN LLQALELQLK LNHPESSQLF AKLLQKMTDL RQIVTEHVQL    480
LQVIKKTETD MSLHPLLQEI YKDLY                                          505
```

```
SEQ ID NO: 33           moltype = AA  length = 366
FEATURE                 Location/Qualifiers
source                  1..366
                        mol_type = protein
                        organism = Homo sapiens
SEQUENCE: 33
MDSDDEMVEE AVEGHLDDDG LPHGFCTVTY SSTDRFEGNF VHGEKNGRGK FFFFDGSTLE     60
GYYVDDALQG QGVYTYEDGG VLQGTYVDGE LNGPAQEYDT DGRLIFKGQY KDNIRHGVCW    120
IYYPDGGSLV GEVNEDGEMT GEKIAYVYPD ERTALYGKFI DGEMIEGKLA TLMSTEEGRP    180
HFELMPGNSV YHFDKSTSSC ISTNALLPDP YESERVYVAE SLISSAGEGL FSKVAVGPNT    240
VMSFYNGVRI THQEVDSRDW ALNGNTLSLD EETVIDVPEP YNHVSKYCAS LGHKANHSFT    300
PNCIYDMFVH PRFGPIKCIR TLRAVEADEE LTVAYGYDHS PPGKSGPEAP EWYQVELKAF    360
QATQQK                                                               366
```

```
SEQ ID NO: 34           moltype = DNA  length = 21
FEATURE                 Location/Qualifiers
misc_feature            1..21
                        note = Synthetic construct
source                  1..21
                        mol_type = other DNA
                        organism = synthetic construct
SEQUENCE: 34
gtcaaagggg catatggaag g                                               21

SEQ ID NO: 35           moltype = DNA  length = 20
FEATURE                 Location/Qualifiers
misc_feature            1..20
```

```
                        note = Synthetic construct
source                  1..20
                        mol_type = other DNA
                        organism = synthetic construct
SEQUENCE: 35
gggaagaaag ccccacttgg                                                    20

SEQ ID NO: 36           moltype = DNA  length = 20
FEATURE                 Location/Qualifiers
misc_feature            1..20
                        note = Synthetic construct
source                  1..20
                        mol_type = other DNA
                        organism = synthetic construct
SEQUENCE: 36
gcccagtcgc gtgggggggg                                                    20

SEQ ID NO: 37           moltype = DNA  length = 20
FEATURE                 Location/Qualifiers
misc_feature            1..20
                        note = Synthetic construct
source                  1..20
                        mol_type = other DNA
                        organism = synthetic construct
SEQUENCE: 37
ggagcgcgag tgtcactcgg                                                    20

SEQ ID NO: 38           moltype = DNA  length = 21
FEATURE                 Location/Qualifiers
source                  1..21
                        mol_type = unassigned DNA
                        organism = Mus musculus
SEQUENCE: 38
gctcactgta ggacccgagc c                                                  21

SEQ ID NO: 39           moltype = DNA  length = 21
FEATURE                 Location/Qualifiers
source                  1..21
                        mol_type = unassigned DNA
                        organism = Mus musculus
SEQUENCE: 39
gacgcggcgc tcattggcca a                                                  21

SEQ ID NO: 40           moltype = DNA  length = 21
FEATURE                 Location/Qualifiers
source                  1..21
                        mol_type = unassigned DNA
                        organism = Mus musculus
SEQUENCE: 40
cgagccgcga gcccagtcgc g                                                  21

SEQ ID NO: 41           moltype = DNA  length = 21
FEATURE                 Location/Qualifiers
source                  1..21
                        mol_type = unassigned DNA
                        organism = Mus musculus
SEQUENCE: 41
tccccccccc cccccacgcg a                                                  21

SEQ ID NO: 42           moltype = DNA  length = 21
FEATURE                 Location/Qualifiers
source                  1..21
                        mol_type = unassigned DNA
                        organism = Mus musculus
SEQUENCE: 42
gtcactcacc ccgattggcc a                                                  21

SEQ ID NO: 43           moltype = DNA  length = 21
FEATURE                 Location/Qualifiers
source                  1..21
                        mol_type = unassigned DNA
                        organism = Mus musculus
SEQUENCE: 43
cgcgagccca gtcgcgtggg g                                                  21

SEQ ID NO: 44           moltype = DNA  length = 21
FEATURE                 Location/Qualifiers
source                  1..21
                        mol_type = unassigned DNA
```

```
                              organism = Mus musculus
SEQUENCE: 44
gttggcttat ccaaacatct c                                              21

SEQ ID NO: 45           moltype = DNA  length = 21
FEATURE                 Location/Qualifiers
source                  1..21
                        mol_type = unassigned DNA
                        organism = Mus musculus
SEQUENCE: 45
atgttaagca agggtaatag a                                              21

SEQ ID NO: 46           moltype = DNA  length = 21
FEATURE                 Location/Qualifiers
source                  1..21
                        mol_type = unassigned DNA
                        organism = Mus musculus
SEQUENCE: 46
ctgtgaaagg aatacaattc a                                              21

SEQ ID NO: 47           moltype = DNA  length = 21
FEATURE                 Location/Qualifiers
source                  1..21
                        mol_type = unassigned DNA
                        organism = Mus musculus
SEQUENCE: 47
gccaattctt ggcaaccgag c                                              21

SEQ ID NO: 48           moltype = DNA  length = 21
FEATURE                 Location/Qualifiers
source                  1..21
                        mol_type = unassigned DNA
                        organism = Mus musculus
SEQUENCE: 48
gaattggcca aagggagggg t                                              21

SEQ ID NO: 49           moltype = DNA  length = 21
FEATURE                 Location/Qualifiers
source                  1..21
                        mol_type = unassigned DNA
                        organism = Mus musculus
SEQUENCE: 49
aattagcaga cagcttggta c                                              21

SEQ ID NO: 50           moltype = DNA  length = 21
FEATURE                 Location/Qualifiers
source                  1..21
                        mol_type = unassigned DNA
                        organism = Mus musculus
SEQUENCE: 50
ctggctgatt cccgaggatt t                                              21

SEQ ID NO: 51           moltype = DNA  length = 21
FEATURE                 Location/Qualifiers
source                  1..21
                        mol_type = unassigned DNA
                        organism = Mus musculus
SEQUENCE: 51
cactgaatac ggattggtca g                                              21

SEQ ID NO: 52           moltype = DNA  length = 21
FEATURE                 Location/Qualifiers
source                  1..21
                        mol_type = unassigned DNA
                        organism = Mus musculus
SEQUENCE: 52
gatgtctcag aaccactgaa t                                              21

SEQ ID NO: 53           moltype = DNA  length = 21
FEATURE                 Location/Qualifiers
source                  1..21
                        mol_type = unassigned DNA
                        organism = Mus musculus
SEQUENCE: 53
aaccactgaa tacggattgg t                                              21

SEQ ID NO: 54           moltype = DNA  length = 21
FEATURE                 Location/Qualifiers
source                  1..21
```

```
                        mol_type = unassigned DNA
                        organism = Mus musculus
SEQUENCE: 54
accaatccgt attcagtggt t                                              21

SEQ ID NO: 55           moltype = DNA  length = 21
FEATURE                 Location/Qualifiers
source                  1..21
                        mol_type = unassigned DNA
                        organism = Homo sapiens
SEQUENCE: 55
ggcgcggggc ggacggggcg a                                              21

SEQ ID NO: 56           moltype = DNA  length = 21
FEATURE                 Location/Qualifiers
source                  1..21
                        mol_type = unassigned DNA
                        organism = Homo sapiens
SEQUENCE: 56
gcgccccggg aacgcgtggg g                                              21

SEQ ID NO: 57           moltype = DNA  length = 21
FEATURE                 Location/Qualifiers
source                  1..21
                        mol_type = unassigned DNA
                        organism = Homo sapiens
SEQUENCE: 57
cgccccgcgc cgcgcgggga g                                              21

SEQ ID NO: 58           moltype = DNA  length = 21
FEATURE                 Location/Qualifiers
source                  1..21
                        mol_type = unassigned DNA
                        organism = Homo sapiens
SEQUENCE: 58
tccgccccgc gccgcgcggg g                                              21

SEQ ID NO: 59           moltype = DNA  length = 21
FEATURE                 Location/Qualifiers
source                  1..21
                        mol_type = unassigned DNA
                        organism = Homo sapiens
SEQUENCE: 59
ggaacgcgtg gggcggagct t                                              21

SEQ ID NO: 60           moltype = DNA  length = 21
FEATURE                 Location/Qualifiers
source                  1..21
                        mol_type = unassigned DNA
                        organism = Homo sapiens
SEQUENCE: 60
gccccgcgcc gcgcggggag g                                              21

SEQ ID NO: 61           moltype = DNA  length = 21
FEATURE                 Location/Qualifiers
source                  1..21
                        mol_type = unassigned DNA
                        organism = Homo sapiens
SEQUENCE: 61
tgcgccccgg gaacgcgtgg g                                              21

SEQ ID NO: 62           moltype = DNA  length = 21
FEATURE                 Location/Qualifiers
source                  1..21
                        mol_type = unassigned DNA
                        organism = Homo sapiens
SEQUENCE: 62
gaacgcgtgg ggcggagctt c                                              21

SEQ ID NO: 63           moltype = DNA  length = 21
FEATURE                 Location/Qualifiers
source                  1..21
                        mol_type = unassigned DNA
                        organism = Homo sapiens
SEQUENCE: 63
gcggcgcggg gcggacgggg c                                              21

SEQ ID NO: 64           moltype = DNA  length = 21
FEATURE                 Location/Qualifiers
```

-continued

```
source                    1..21
                          mol_type = unassigned DNA
                          organism = Homo sapiens
SEQUENCE: 64
cccgtccgcc ccgcgccgcg c                                              21

SEQ ID NO: 65             moltype = DNA   length = 21
FEATURE                   Location/Qualifiers
source                    1..21
                          mol_type = unassigned DNA
                          organism = Homo sapiens
SEQUENCE: 65
ggcccactcg ccgccaatca g                                              21

SEQ ID NO: 66             moltype = DNA   length = 21
FEATURE                   Location/Qualifiers
source                    1..21
                          mol_type = unassigned DNA
                          organism = Homo sapiens
SEQUENCE: 66
ggaagccgcc ggggccgcct a                                              21

SEQ ID NO: 67             moltype = DNA   length = 21
FEATURE                   Location/Qualifiers
source                    1..21
                          mol_type = unassigned DNA
                          organism = Homo sapiens
SEQUENCE: 67
tgattggcgg cgagtgggcc a                                              21

SEQ ID NO: 68             moltype = DNA   length = 21
FEATURE                   Location/Qualifiers
source                    1..21
                          mol_type = unassigned DNA
                          organism = Homo sapiens
SEQUENCE: 68
gccgccaatc agcggaagcc g                                              21

SEQ ID NO: 69             moltype = DNA   length = 21
FEATURE                   Location/Qualifiers
source                    1..21
                          mol_type = unassigned DNA
                          organism = Homo sapiens
SEQUENCE: 69
ggcggcttcc gctgattggc g                                              21

SEQ ID NO: 70             moltype = DNA   length = 21
FEATURE                   Location/Qualifiers
source                    1..21
                          mol_type = unassigned DNA
                          organism = Homo sapiens
SEQUENCE: 70
ccgccaatca gcggaagccg c                                              21

SEQ ID NO: 71             moltype = DNA   length = 21
FEATURE                   Location/Qualifiers
source                    1..21
                          mol_type = unassigned DNA
                          organism = Homo sapiens
SEQUENCE: 71
agccgccggg gccgcctaga g                                              21

SEQ ID NO: 72             moltype = DNA   length = 21
FEATURE                   Location/Qualifiers
source                    1..21
                          mol_type = unassigned DNA
                          organism = Homo sapiens
SEQUENCE: 72
gcttccgctg attggcggcg a                                              21

SEQ ID NO: 73             moltype = DNA   length = 21
FEATURE                   Location/Qualifiers
source                    1..21
                          mol_type = unassigned DNA
                          organism = Homo sapiens
SEQUENCE: 73
cggcgagtgg gccaatgggt g                                              21

SEQ ID NO: 74             moltype = DNA   length = 21
```

-continued

```
FEATURE                 Location/Qualifiers
source                  1..21
                        mol_type = unassigned DNA
                        organism = Homo sapiens
SEQUENCE: 74
ccaatgggtg cggggcggtg g                                              21

SEQ ID NO: 75           moltype = DNA   length = 21
FEATURE                 Location/Qualifiers
source                  1..21
                        mol_type = unassigned DNA
                        organism = Mus musculus
SEQUENCE: 75
ggctgccggg gccgcctaaa g                                              21

SEQ ID NO: 76           moltype = DNA   length = 21
FEATURE                 Location/Qualifiers
source                  1..21
                        mol_type = unassigned DNA
                        organism = Mus musculus
SEQUENCE: 76
ggaggctgcc ggggccgcct a                                              21

SEQ ID NO: 77           moltype = DNA   length = 21
FEATURE                 Location/Qualifiers
source                  1..21
                        mol_type = unassigned DNA
                        organism = Mus musculus
SEQUENCE: 77
gccgccaatc agcggaggct g                                              21

SEQ ID NO: 78           moltype = DNA   length = 21
FEATURE                 Location/Qualifiers
source                  1..21
                        mol_type = unassigned DNA
                        organism = Mus musculus
SEQUENCE: 78
ccgccaatca gcggaggctg c                                              21

SEQ ID NO: 79           moltype = DNA   length = 21
FEATURE                 Location/Qualifiers
source                  1..21
                        mol_type = unassigned DNA
                        organism = Mus musculus
SEQUENCE: 79
tggccggtgc gccgccaatc a                                              21

SEQ ID NO: 80           moltype = DNA   length = 21
FEATURE                 Location/Qualifiers
source                  1..21
                        mol_type = unassigned DNA
                        organism = Mus musculus
SEQUENCE: 80
ggccggtgcg ccgccaatca g                                              21

SEQ ID NO: 81           moltype = DNA   length = 21
FEATURE                 Location/Qualifiers
source                  1..21
                        mol_type = unassigned DNA
                        organism = Mus musculus
SEQUENCE: 81
cggcgcaccg gccaataagt g                                              21

SEQ ID NO: 82           moltype = DNA   length = 21
FEATURE                 Location/Qualifiers
source                  1..21
                        mol_type = unassigned DNA
                        organism = Mus musculus
SEQUENCE: 82
ataagtgtgg ggcggtgggc g                                              21

SEQ ID NO: 83           moltype = DNA   length = 21
FEATURE                 Location/Qualifiers
source                  1..21
                        mol_type = unassigned DNA
                        organism = Mus musculus
SEQUENCE: 83
ccaataagtg tggggcggtg g                                              21
```

-continued

```
SEQ ID NO: 84              moltype = DNA  length = 21
FEATURE                    Location/Qualifiers
source                     1..21
                           mol_type = unassigned DNA
                           organism = Mus musculus
SEQUENCE: 84
caataagtgt ggggcggtgg g                                                   21

SEQ ID NO: 85              moltype = DNA  length = 20
FEATURE                    Location/Qualifiers
source                     1..20
                           mol_type = unassigned DNA
                           organism = Mus musculus
SEQUENCE: 85
cctttctatg acctagtcgg                                                     20

SEQ ID NO: 86              moltype = DNA  length = 20
FEATURE                    Location/Qualifiers
source                     1..20
                           mol_type = unassigned DNA
                           organism = Mus musculus
SEQUENCE: 86
cagaatcagt aacgcactgt                                                     20

SEQ ID NO: 87              moltype = DNA  length = 20
FEATURE                    Location/Qualifiers
source                     1..20
                           mol_type = unassigned DNA
                           organism = Mus musculus
SEQUENCE: 87
gaaaccagga gagataaccc                                                     20

SEQ ID NO: 88              moltype = DNA  length = 20
FEATURE                    Location/Qualifiers
source                     1..20
                           mol_type = unassigned DNA
                           organism = Mus musculus
SEQUENCE: 88
ggaccccaga tattctggaa                                                     20

SEQ ID NO: 89              moltype = DNA  length = 20
FEATURE                    Location/Qualifiers
source                     1..20
                           mol_type = unassigned DNA
                           organism = Mus musculus
SEQUENCE: 89
ttattgttga cttaacgaag                                                     20

SEQ ID NO: 90              moltype = DNA  length = 20
FEATURE                    Location/Qualifiers
source                     1..20
                           mol_type = unassigned DNA
                           organism = Mus musculus
SEQUENCE: 90
aaaaagaagc aaatagctaa                                                     20

SEQ ID NO: 91              moltype = DNA  length = 20
FEATURE                    Location/Qualifiers
source                     1..20
                           mol_type = unassigned DNA
                           organism = Mus musculus
SEQUENCE: 91
agaatcagta acgcactgta                                                     20

SEQ ID NO: 92              moltype = DNA  length = 27
FEATURE                    Location/Qualifiers
source                     1..27
                           mol_type = unassigned DNA
                           organism = Mus musculus
SEQUENCE: 92
tgttggttta ttggaccccca gatattc                                            27

SEQ ID NO: 93              moltype = DNA  length = 27
FEATURE                    Location/Qualifiers
source                     1..27
                           mol_type = unassigned DNA
                           organism = Mus musculus
SEQUENCE: 93
tgttggagaa aattaactta gtgcata                                             27
```

```
SEQ ID NO: 94           moltype = DNA  length = 27
FEATURE                 Location/Qualifiers
source                  1..27
                        mol_type = unassigned DNA
                        organism = Mus musculus
SEQUENCE: 94
tgttggtata actgccacta gagggct                                                27

SEQ ID NO: 95           moltype = DNA  length = 19
FEATURE                 Location/Qualifiers
source                  1..19
                        mol_type = unassigned DNA
                        organism = Homo sapiens
SEQUENCE: 95
aggagccggg acccaccgg                                                         19
```